(12) United States Patent
Lee et al.

(10) Patent No.: US 10,709,467 B2
(45) Date of Patent: Jul. 14, 2020

(54) SURGICAL INSTRUMENT

(71) Applicant: LIVSMED INC., Seongnam-si, Gyeonggi-do (KR)

(72) Inventors: Jung Joo Lee, Seoul (KR); Hee Jin Kim, Seoul (KR); Du Jin Bach, Seoul (KR)

(73) Assignee: LIVSMED INC., Seongnam-si (KR)

( * ) Notice: Subject to any disclaimer, the term of this patent is extended or adjusted under 35 U.S.C. 154(b) by 456 days.

(21) Appl. No.: 15/516,603

(22) PCT Filed: Oct. 2, 2014

(86) PCT No.: PCT/KR2014/009319
§ 371 (c)(1),
(2) Date: Apr. 3, 2017

(87) PCT Pub. No.: WO2016/052784
PCT Pub. Date: Apr. 7, 2016

(65) Prior Publication Data
US 2018/0228506 A1 Aug. 16, 2018

(51) Int. Cl.
*A61B 17/29* (2006.01)
*A61B 34/00* (2016.01)
*A61B 17/00* (2006.01)

(52) U.S. Cl.
CPC .......... *A61B 17/2909* (2013.01); *A61B 34/71* (2016.02); *A61B 2017/00314* (2013.01);
(Continued)

(58) Field of Classification Search
CPC ................... H04J 1/00; A61B 17/2909; A61B 2017/0042; A61B 2017/00424;
(Continued)

(56) References Cited

U.S. PATENT DOCUMENTS 3,273,408 A 9/1966 Nagel et al.
3,529,481 A 9/1970 Boleslaw
(Continued)

FOREIGN PATENT DOCUMENTS

CN 102131469 A 7/2011
JP S59102587 A 6/1984
(Continued)

*Primary Examiner* — Kathleen S Holwerda
*Assistant Examiner* — Kankindi Rwego
(74) *Attorney, Agent, or Firm* — Novick, Kim & Lee, PLLC; Sang Ho Lee

(57) ABSTRACT

Provided is a surgical instrument, in more detail, a surgical instrument that may be manually operated to be used in laparoscopic surgery or various other kinds of surgery. To this end, the present invention provides a surgical instrument including an end tool configured to be rotatable in at least two directions; a manipulator including a pitch operator controlling a pitch movement of the end tool, a yaw operator controlling a yaw movement of the end tool, and an actuation operator controlling an actuation movement of the end tool; a power transfer unit configured to transfer an operation of the manipulator to the end tool; and a connection unit extending in a first direction (X-axis), and connecting the manipulator to the end tool when the end tool is coupled to an end portion of the connection unit and the manipulator is coupled to the other end portion of the connection unit, wherein at least a part of the manipulator extends towards the end tool.

36 Claims, 66 Drawing Sheets

(52) U.S. Cl.
CPC .............. *A61B 2017/00323* (2013.01); *A61B 2017/00424* (2013.01); *A61B 2017/00438* (2013.01); *A61B 2017/291* (2013.01); *A61B 2017/2911* (2013.01); *A61B 2017/2912* (2013.01); *A61B 2017/2917* (2013.01); *A61B 2017/2927* (2013.01); *A61B 2017/2929* (2013.01); *A61B 2017/2947* (2013.01)

(58) Field of Classification Search
CPC .... A61B 2017/2927; A61B 2017/2929; A61B 2017/291; A61B 34/74; A61B 34/76
See application file for complete search history.

(56) References Cited

U.S. PATENT DOCUMENTS

| | | | |
|---|---|---|---|
| 5,478,347 A * | 12/1995 | Aranyi | A61B 17/29 606/167 |
| 5,539,987 A | 7/1996 | Zennyoji | |
| 5,792,165 A | 8/1998 | Klieman et al. | |
| 5,797,900 A | 8/1998 | Madhani et al. | |
| 5,908,436 A * | 6/1999 | Cuschieri | A61B 17/2909 606/1 |
| 5,954,731 A | 9/1999 | Yoon | |
| 6,191,017 B1 | 2/2001 | Chittipeddi et al. | |
| 6,394,998 B1 | 5/2002 | Wallace et al. | |
| 6,432,112 B2 | 8/2002 | Brock et al. | |
| 6,554,844 B2 | 4/2003 | Lee et al. | |
| 6,676,684 B1 | 1/2004 | Morley et al. | |
| 6,692,485 B1 | 2/2004 | Brock et al. | |
| 6,889,116 B2 | 5/2005 | Jinno | |
| 6,936,042 B2 | 8/2005 | Wallace et al. | |
| 6,969,385 B2 | 11/2005 | Moreyra | |
| 6,994,716 B2 | 2/2006 | Jinno et al. | |
| 7,101,363 B2 | 9/2006 | Nishizawa et al. | |
| 7,338,513 B2 | 3/2008 | Lee et al. | |
| 7,364,582 B2 | 4/2008 | Lee | |
| 7,540,867 B2 | 6/2009 | Jinno et al. | |
| 7,648,519 B2 | 1/2010 | Lee et al. | |
| 7,686,826 B2 | 3/2010 | Lee et al. | |
| 7,914,522 B2 | 3/2011 | Morley et al. | |
| 7,942,895 B2 | 5/2011 | Jinno et al. | |
| 8,100,824 B2 | 1/2012 | Hegeman et al. | |
| 8,465,475 B2 | 6/2013 | Isbell, Jr. | |
| 8,801,731 B2 | 8/2014 | Jeong | |
| 8,821,480 B2 | 9/2014 | Burbank | |
| 9,033,998 B1 | 5/2015 | Schaible et al. | |
| 9,179,927 B2 | 11/2015 | Stefanchik et al. | |
| 9,695,916 B2 | 7/2017 | Lee | |
| 9,737,302 B2 | 8/2017 | Shelton, IV et al. | |
| 10,105,128 B2 | 10/2018 | Cooper et al. | |
| 10,166,082 B1 | 1/2019 | Hariri et al. | |
| 10,405,936 B2 | 9/2019 | Awtar et al. | |
| 2003/0036748 A1 | 2/2003 | Cooper et al. | |
| 2004/0199147 A1 | 10/2004 | Nishizawa et al. | |
| 2005/0096694 A1 * | 5/2005 | Lee | A61B 17/00234 606/205 |
| 2006/0020287 A1 | 1/2006 | Lee | |
| 2006/0190034 A1 | 8/2006 | Nishizawa | |
| 2006/0219065 A1 * | 10/2006 | Jinno | A61B 34/70 81/383 |
| 2007/0208375 A1 | 9/2007 | Nishizawa | |
| 2007/0265502 A1 * | 11/2007 | Minosawa | A61B 1/00177 600/173 |
| 2008/0000317 A1 | 1/2008 | Patton | |
| 2008/0039255 A1 | 2/2008 | Jinno | |
| 2008/0065116 A1 | 3/2008 | Lee et al. | |
| 2008/0245175 A1 | 10/2008 | Jinno | |
| 2009/0112230 A1 | 4/2009 | Jinno | |
| 2010/0198253 A1 | 8/2010 | Jinno | |
| 2010/0249818 A1 | 9/2010 | Jinno | |
| 2010/0286480 A1 | 11/2010 | Peine et al. | |
| 2011/0106145 A1 | 5/2011 | Jeong | |
| 2011/0112517 A1 | 5/2011 | Peine | |
| 2012/0004648 A1 | 1/2012 | Choi et al. | |
| 2012/0330287 A1 | 12/2012 | Yim | |
| 2013/0012958 A1 | 1/2013 | Marczyk et al. | |
| 2013/0012959 A1 | 1/2013 | Jinno | |
| 2013/0144274 A1 | 6/2013 | Stefanchik et al. | |
| 2014/0114293 A1 | 4/2014 | Jeong et al. | |
| 2014/0194893 A1 | 7/2014 | Jeong et al. | |
| 2014/0318288 A1 | 10/2014 | Lee | |
| 2014/0350570 A1 | 11/2014 | Lee | |
| 2015/0032125 A1 | 1/2015 | Jeong et al. | |
| 2015/0150635 A1 | 6/2015 | Kilroy et al. | |
| 2016/0008068 A1 | 1/2016 | Hyodo et al. | |
| 2016/0256232 A1 | 9/2016 | Awtar et al. | |
| 2017/0042560 A1 | 2/2017 | Lee et al. | |
| 2018/0110577 A1 | 4/2018 | Lee et al. | |
| 2018/0228506 A1 | 8/2018 | Lee et al. | |
| 2019/0336230 A1 | 11/2019 | Awtar et al. | |

FOREIGN PATENT DOCUMENTS

| | | |
|---|---|---|
| JP | 6449739 A | 2/1989 |
| JP | H06-311984 A | 11/1994 |
| JP | H08173442 A | 7/1996 |
| JP | 2004-122286 A | 4/2004 |
| JP | 2006-34978 A | 2/2006 |
| JP | 2006-061364 A | 3/2006 |
| JP | 2006-116194 A | 5/2006 |
| JP | 2008-521485 A | 6/2008 |
| JP | 2010-220786 A | 10/2010 |
| JP | 4701433 B2 | 3/2011 |
| JP | 2011-521703 A | 7/2011 |
| JP | 2011-200666 A | 10/2011 |
| KR | 10-0695471 B1 | 3/2007 |
| KR | 10-2009-0119366 A | 11/2009 |
| KR | 10-2009-0124828 A | 12/2009 |
| KR | 10-0956760 B1 | 5/2010 |
| KR | 10-2010-0099818 A | 9/2010 |
| KR | 10-2010-0118573 A | 11/2010 |
| KR | 10-2011-0005671 A | 1/2011 |
| KR | 10-2011-0014534 A | 2/2011 |
| KR | 10-2011-0028613 A | 3/2011 |
| KR | 101064825 B1 | 9/2011 |
| KR | 10-1075294 B1 | 10/2011 |
| KR | 10-2013-0023311 A | 3/2013 |
| KR | 10-2013-0023755 A | 3/2013 |
| KR | 10-2013-0057250 A | 5/2013 |
| KR | 10-1301783 B1 | 8/2013 |
| KR | 10-1364970 B1 | 2/2014 |
| KR | 10-2014-0113893 A | 9/2014 |
| WO | 2009/100366 A2 | 8/2009 |
| WO | 2009158115 A1 | 12/2009 |
| WO | 2010/030114 A2 | 3/2010 |
| WO | 2011/115311 A1 | 9/2011 |
| WO | 2012074564 A1 | 6/2012 |
| WO | 2013/077571 A1 | 5/2013 |
| WO | 2013082220 A2 | 6/2013 |
| WO | 2014/123390 A1 | 8/2014 |
| WO | 2014/156219 A1 | 10/2014 |

* cited by examiner

FIG. 11A
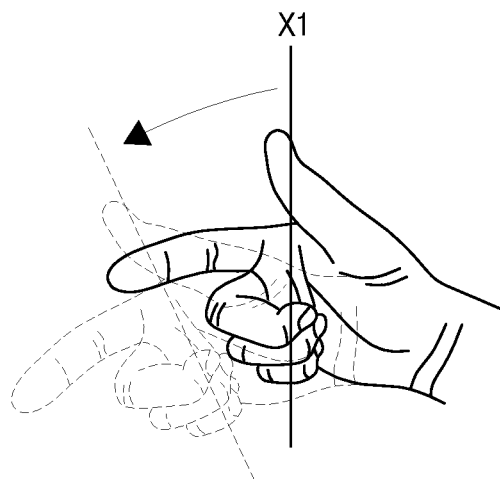
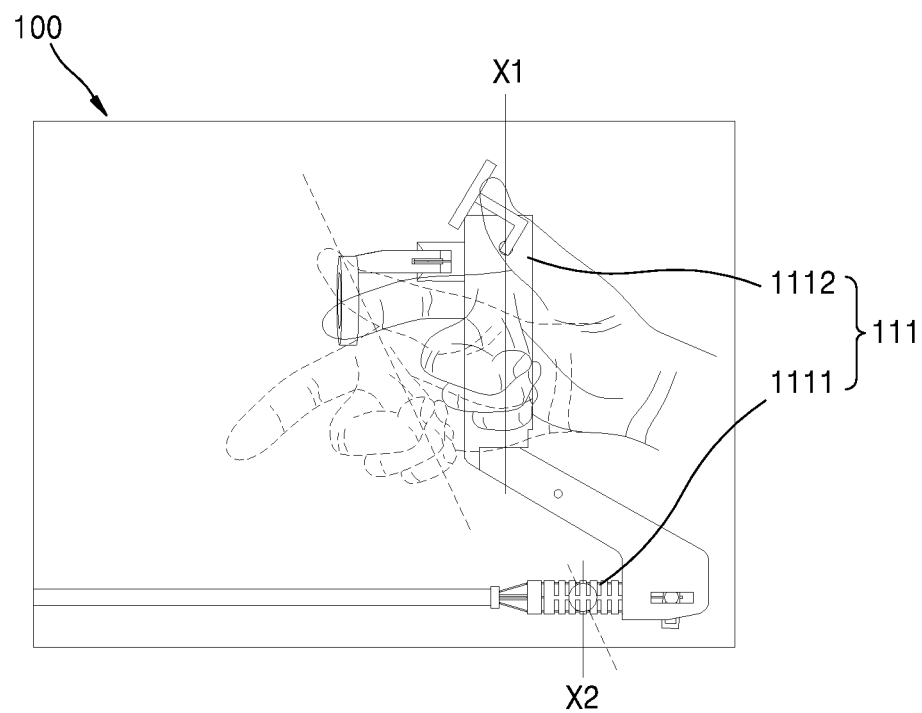

FIG. 11B
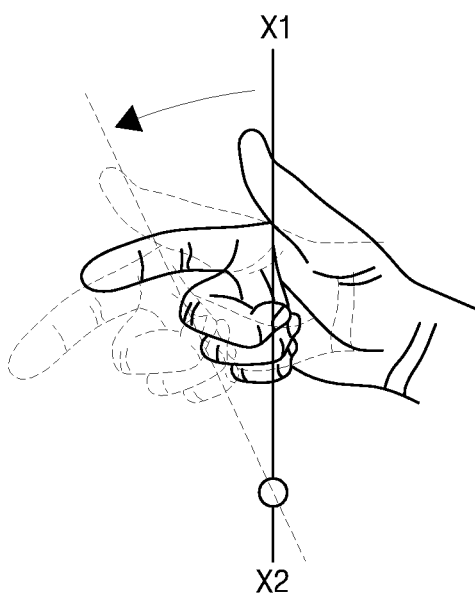
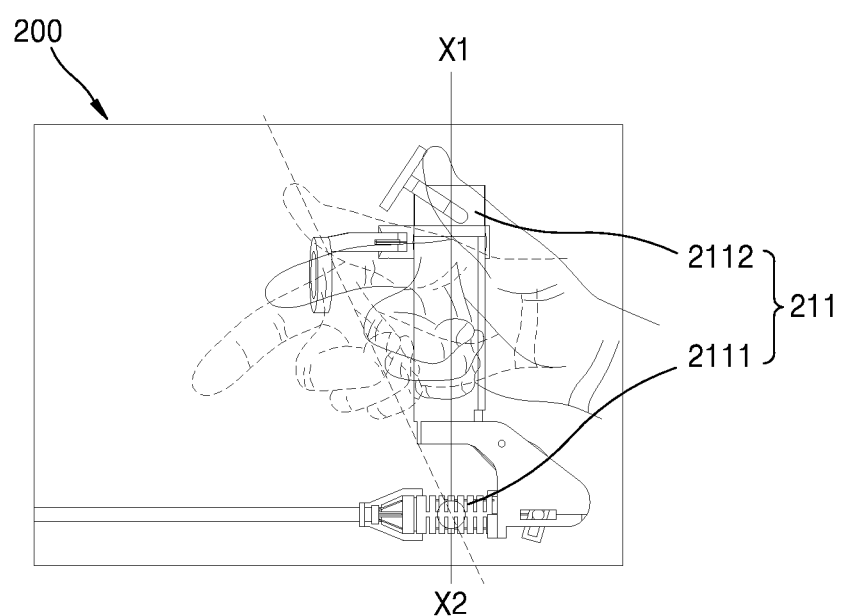

FIG. 11C
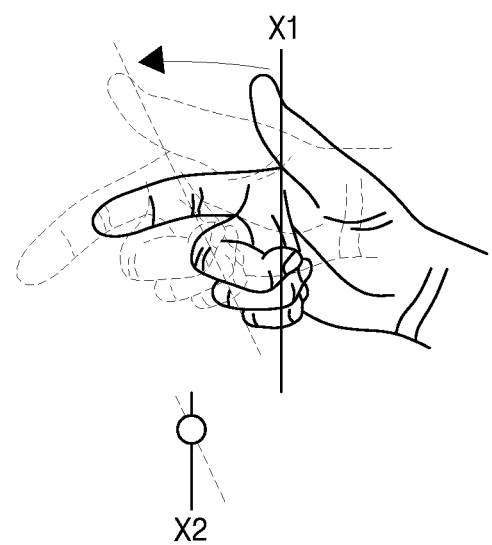
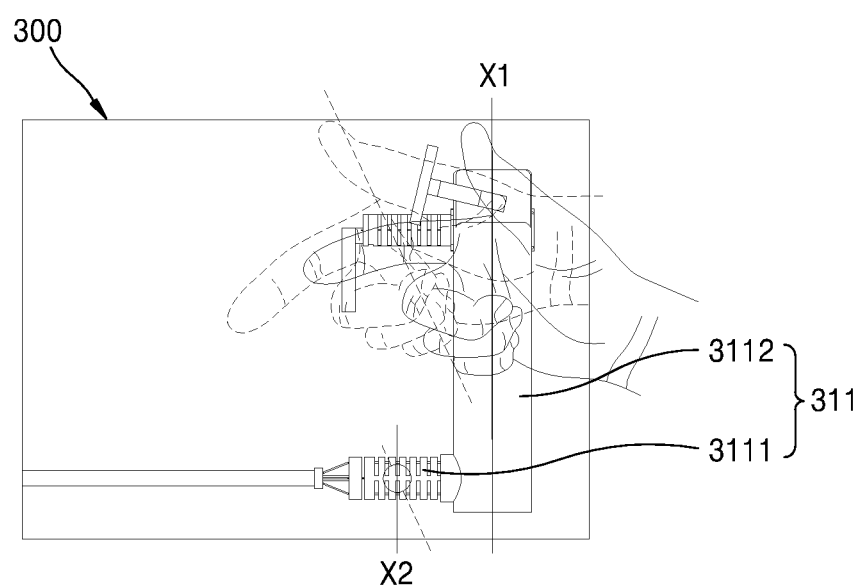

FIG. 18A
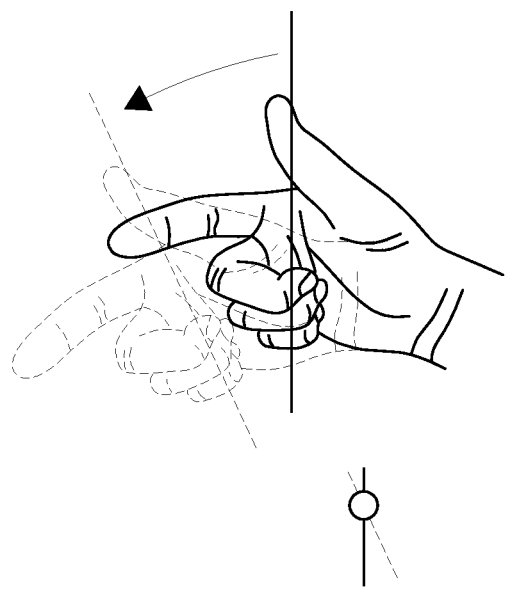
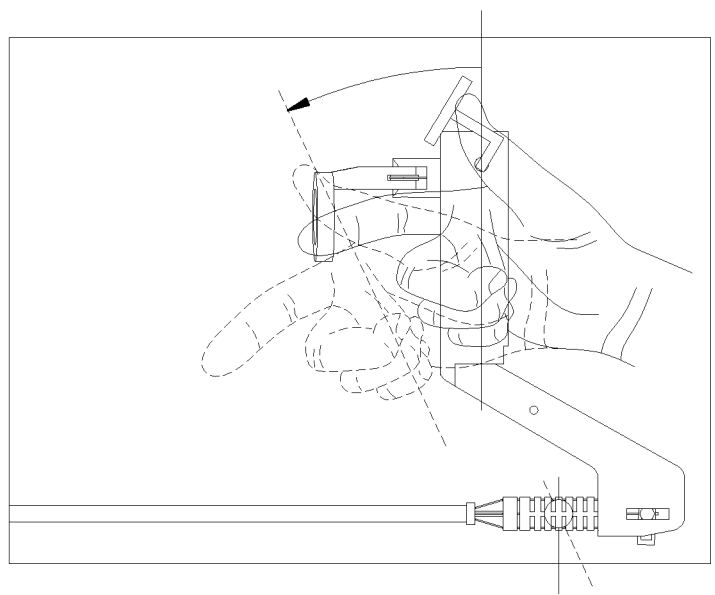

FIG. 18C
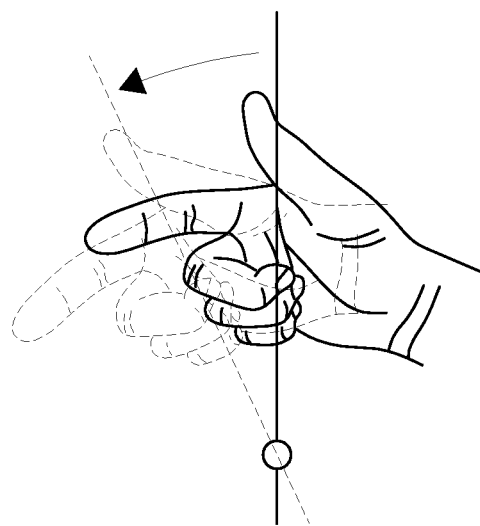
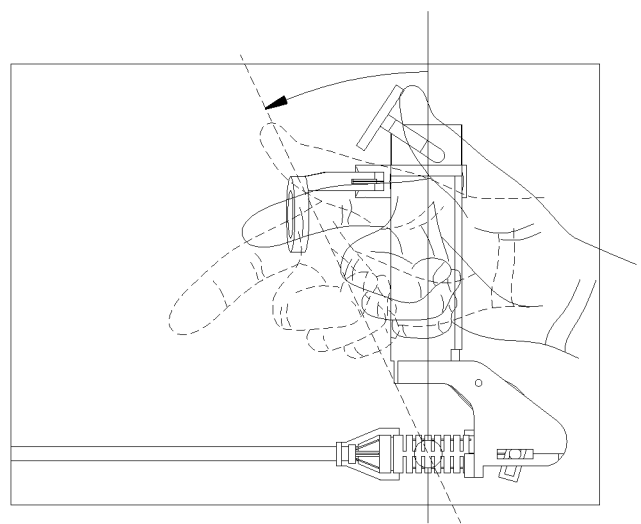

FIG. 18E
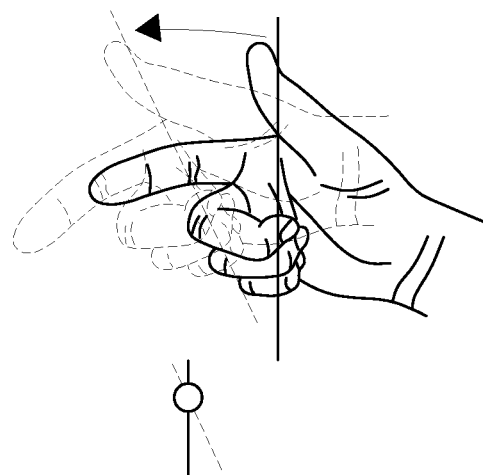
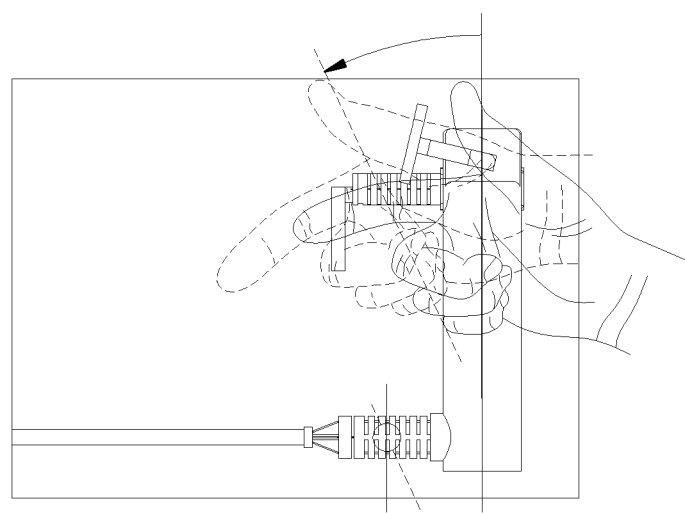

SURGICAL INSTRUMENT

TECHNICAL FIELD

The present invention relates to a surgical instrument, and more particularly, to a surgical instrument that may be manually operated to be used in laparoscopic surgery or various other kinds of surgery.

BACKGROUND ART

Surgery denotes an operation of curing a disease by cutting, incising, or processing skin, membranes, and other tissues by using a medical instrument. In addition, laparotomy that cures, shapes, or removes an organ by cutting and opening the skin of a surgical site may cause bleeding, side effects, pain of a patient, scars, etc. Therefore, surgery performed by inserting only a medical instrument, e.g., a laparoscope, a surgical instrument, a microscope for microsurgery, etc. into the skin after forming a predetermined hole through the skin, or surgery using a robot has been recently considered as an alternative.

A surgical instrument is an instrument having an end tool provided at an end of a shaft that passes through a hole in the skin, so that a doctor directly manipulates the end tool with his/her own hands via a predetermined driver or manipulates the end tool by using a robot arm to carry out an operation on a surgical site. The end tool provided at the surgical instrument performs a pivoting operation, a gripping operation, a cutting operation, etc. via a predetermined structure.

However, the surgical instrument according to the related art has the end tool that is not bent, and thus, it is not easy for the surgical instrument to access the surgical site and to perform surgical operations. Surgical instruments having an end tool that may be curved have been developed to address the above problem; however, operations of a manipulator for curving the end tool or performing surgical operations are not intuitively identical with actual bending of the end tool or actual surgical operations of the end tool, and thus, it may not be easy for an operator to intuitively manipulate the surgical instrument and it takes the operator a long time period to be skilled to use the surgical instrument.

The information in the background art described above was obtained by the inventors for the purpose of developing the present disclosure or was obtained during the process of developing the present disclosure. As such, it is to be appreciated that this information did not necessarily belong to the public domain before the patent filing date of the present disclosure.

DETAILED DESCRIPTION OF THE INVENTIVE CONCEPT

Technical Problem

One or more embodiments of the present invention include a surgical instrument capable of making an actual operation of curving an end tool or performing of a surgical operation intuitively match with a corresponding operation of a manipulator. One or more embodiments provides an end tool having various degrees of freedom, a manipulator having a structure capable of intuitively manipulating an operation of the end tool, and a power transfer unit for transferring a driving power of the manipulator to the end tool so that the end tool may be operated according to the manipulation of the manipulator.

Technical Solution

According to an embodiment of the present invention, there is provided a surgical instrument including: an end tool configured to be rotatable in at least two directions; a manipulator including a pitch operator configured to control a pitch movement of the end tool, a yaw operator configured to control a yaw movement of the end tool, and an actuation operator configured to control an actuation movement of the end tool, wherein at least one of the pitch operator and the yaw operator includes a joint member that is curved in one or more directions; a power transfer unit configured to transfer an operation of the manipulator to the end tool; and a connection unit configured to extend in a first direction (X-axis), and to connect the manipulator to the end tool when the end tool is coupled to an end portion of the connection unit and the manipulator is coupled to the other end portion of the connection unit, wherein at least a part of the manipulator extends towards the end tool.

Advantageous Effects

According to embodiments of the present invention, since an operation direction of a manipulator by a surgical operator and an operation direction of an end tool are intuitively identical to each other, convenience of the surgical operator may be improved, and accuracy, reliability, and quickness of surgery may be improved.

DESCRIPTION OF THE DRAWINGS

FIGS. 11A, 11B, and 11C are schematic diagrams of pitch operations of the surgical instrument according to the first, second, and third embodiments of the present invention;

FIG. 18A is a conceptual diagram of a pitch operation of a surgical instrument according to a fifth embodiment of the present invention.

FIG. 18C is a conceptual diagram of a pitch operation of a surgical instrument according to a sixth embodiment of the present invention.

FIG. 18E is a conceptual diagram of a pitch operation of a surgical instrument according to a seventh embodiment of the present invention.

MODE OF THE INVENTION

Figure 1A:
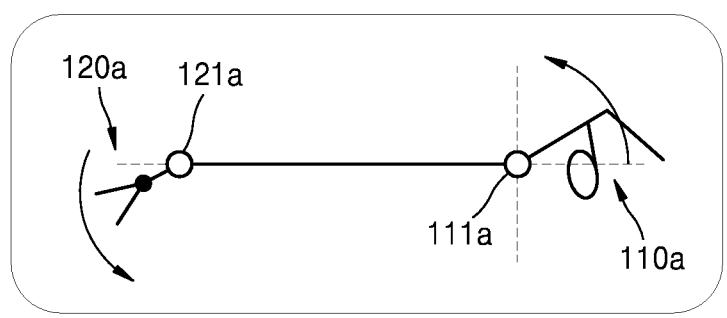
FIG. 1A is a conceptual diagram of a pitch operation in a surgical instrument according to the related art.

As the inventive concept allows for various changes and numerous embodiments, particular embodiments will be illustrated in the drawings and described in detail in the written description. However, this is not intended to limit the present disclosure to particular modes of practice, and it is to be appreciated that all modifications, equivalents, and/or alternatives that do not depart from the spirit and technical scope are encompassed in the inventive concept. In the description, certain detailed explanations of the related art are omitted when it is deemed that they may unnecessarily obscure the essence of the present disclosure.

It will be understood that although the terms "first," "second," etc. may be used herein to describe various components, these components should not be limited by these terms. These components are only used to distinguish one component from another. These components are only used to distinguish one component from another.

The terms used in the present specification are merely used to describe particular embodiments, and are not intended to limit the present disclosure. An expression used in the singular encompasses the expression of the plural, unless it has a clearly different meaning in the context. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, the exemplary embodiments will be described in detail with reference to the accompanying drawings. In the drawings, like reference numerals denote like or corresponding elements, and repeated descriptions thereof will be omitted.

Also, it will be understood that various embodiments of the present invention may be interpreted or implemented in combination, and technical features of each embodiment may be interpreted or implemented in combination with technical features of other embodiments.

First Embodiment of a Surgical Instrument (E1+H1a)

The surgical instrument according to the present invention is characterized in that, when a manipulator is rotated in a direction with respect to at least one operation among a pitch operation, a yaw operation, and an actuation operation, an end tool is intuitively rotated in a direction that is the same as the manipulation direction of the manipulator.

Figure 1B:
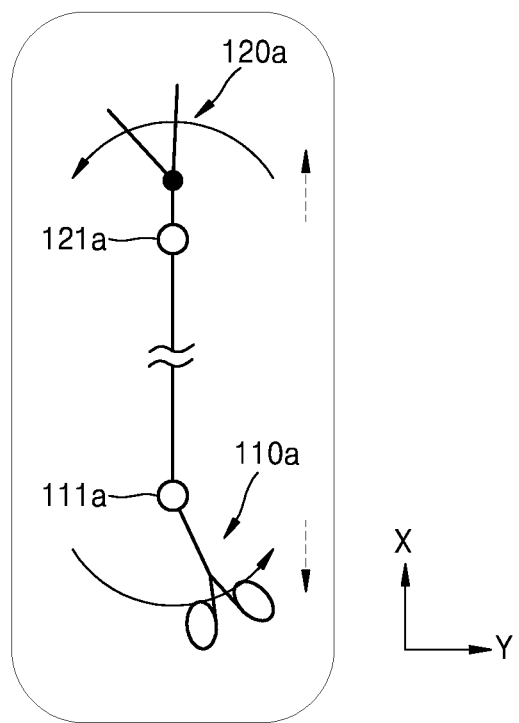
FIG. 1B is a conceptual diagram of a yaw operation.

FIG. 1A is a conceptual diagram of a pitch operation in a surgical instrument according to the related art, and FIG. 1B is a conceptual diagram of a yaw operation.

Referring to FIG. 1A, in performing a pitch operation of a surgical instrument according to the related art, in a state where an end tool 120a is formed in front of a rotating center 121a of the end tool and a manipulator 110a is formed behind a rotating center 111a of the manipulator, when the manipulator 110a is rotated in a clockwise direction, the end tool 120a is also rotated in the clockwise direction, and when the manipulator 120a is rotated in a counter-clockwise direction, the end tool 120a is also rotated in the counter-clockwise direction. In addition, referring to FIG. 1B, in performing a yaw operation of the surgical instrument according to the related art, in a state where the end tool 120a is formed in front of the rotating center 121a of the end tool and the manipulator 110a is formed behind the rotating center 111a of the manipulator, when the manipulator 110a is rotated in the clockwise direction, the end tool 120a is also rotated in the clockwise direction and when the manipulator 120a is rotated in the counter-clockwise direction, the end tool 120a is also rotated in the counter-clockwise direction. In this case, when it comes to left and right sides of a user, when the user moves the manipulator 110a to the left side, the end tool 120a is moved to the right side, and when the user moves the manipulator 110a to the right side, the end tool 120a is moved to the left side. Consequently, the manipulation direction of the user and the operating direction of the end tool are opposite to each other, and thus, it may not be easy for the user to manipulate the surgical instrument.

Figure 1C:
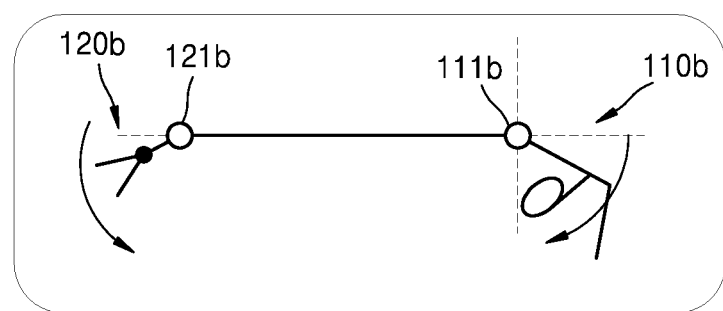
FIG. 1C is a conceptual diagram of a pitch operation in a surgical instrument according to another related art.
Figure 1D:
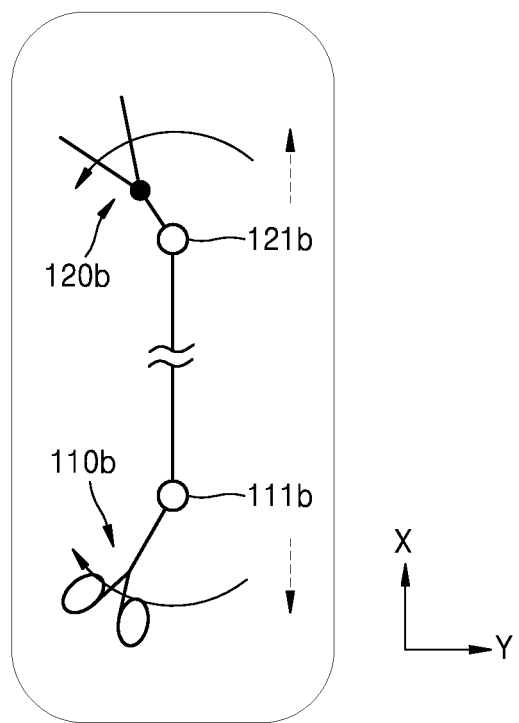
FIG. 1D is a conceptual diagram of a yaw operation.

FIG. 1C is a conceptual diagram of a pitch operation in a surgical instrument according to another related art, and FIG. 1D is a conceptual diagram of a yaw operation.

Referring to FIG. 1C, since a part of the surgical instrument according to the related art is formed as a mirror symmetry type, in a state where the end tool 120b is formed in front of the rotating center 121b of the end tool and the manipulator 110b is formed behind the rotating center 111b of the manipulator when performing a pitch operation, when the manipulator 110b is rotated in the clockwise direction, the end tool 120b is rotated in the counter-clockwise direction, and when the manipulator 110b is rotated in the counter-clockwise direction, the end tool 120b is rotated in the clockwise direction. In this case, when it comes to rotating directions of the manipulator and the end tool, the direction in which the user rotates the manipulator 110b and the rotating direction of the end tool 120b are opposite to each other. Consequently, the user may feel confusion in manipulation, operations of a joint are not intuitive, and a mistake may occur in manipulation. In addition, referring to FIG. 1D, during the yaw operation, in a state where the end tool 120b is formed in front of the rotating center 121b of the end tool and the manipulator 110b is formed behind the rotating center 111b of the manipulator, when the manipulator 110b is rotated in the clockwise direction, the end tool 120b is rotated in the counter-clockwise direction, and when the manipulator 110b is rotated in the counter-clockwise direction, the end tool 120b is rotated in the clockwise direction. In this case, when it comes to rotating directions of the manipulator and the end tool, the direction in which the user rotates the manipulator 110b and the rotating direction of the end tool 120b are opposite to each other. Consequently, the user may feel confusion in manipulation, operations of a joint are not intuitive, and a mistake may occur in manipulation.

Figure 1E:
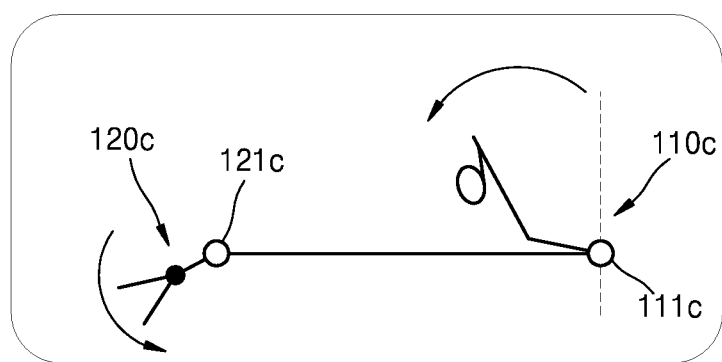
FIG. 1E is a conceptual diagram of a pitch operation in a surgical instrument according to the present invention.
Figure 1F:
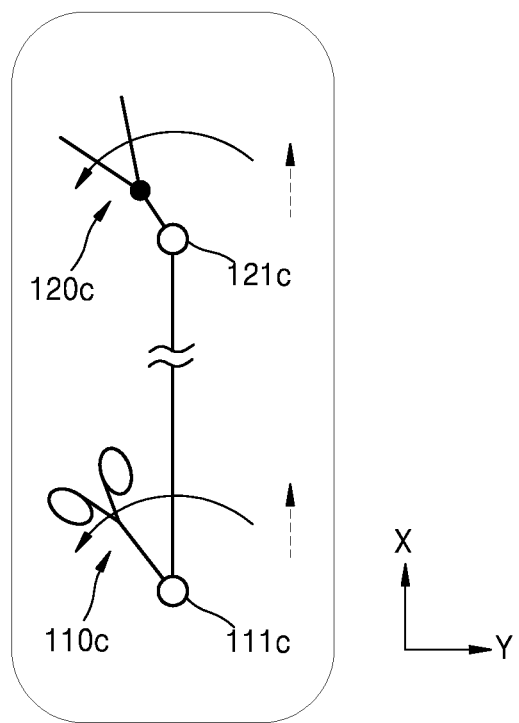
FIG. 1F is a conceptual diagram of a yaw operation.

To address the above problem, in a surgical instrument illustrated with reference to FIGS. 1E and 1F according to an embodiment of the present invention, an end tool 120c is formed in front of a rotating center 121c of the end tool and a manipulator 110c is also formed in front of a rotating center 111c of the manipulator, operations of the manipulator 110c and the end tool 120c intuitively coincide with each other.

In other words, in the surgical instrument according to the related art as shown in FIGS. 1A, 1B, 1C, and 1D, the end tool is located in front of the rotating center thereof, whereas the manipulator is located behind the rotating center thereof, and thus, the end tool, a front portion of which is moved in a state where a rear portion of which is fixed, is moved via the operation of the manipulator, a rear portion of which is moved in a state where a front portion of which is fixed, and structures do not intuitively match with each other. As such, inconsistency occurs between the manipulation of the manipulator and the operation of the end tool in view of the left-and-right direction or the rotating direction, the user may be confused, and the manipulator may not be manipulated intuitively and rapidly and mistakes of the user may occur. On the other hand, in the surgical instrument according to the embodiment of the present invention, the end tool and the manipulator are moved based on the rotating centers located at rear portions thereof, and thus, operations of the end tool and the manipulator may intuitively match with each other. Accordingly, the user may adjust intuitively and rapidly the direction of the end tool, and a possibility of generating mistakes is greatly reduced. Hereinafter, the present invention will be described below in more detail.

Figure 2:
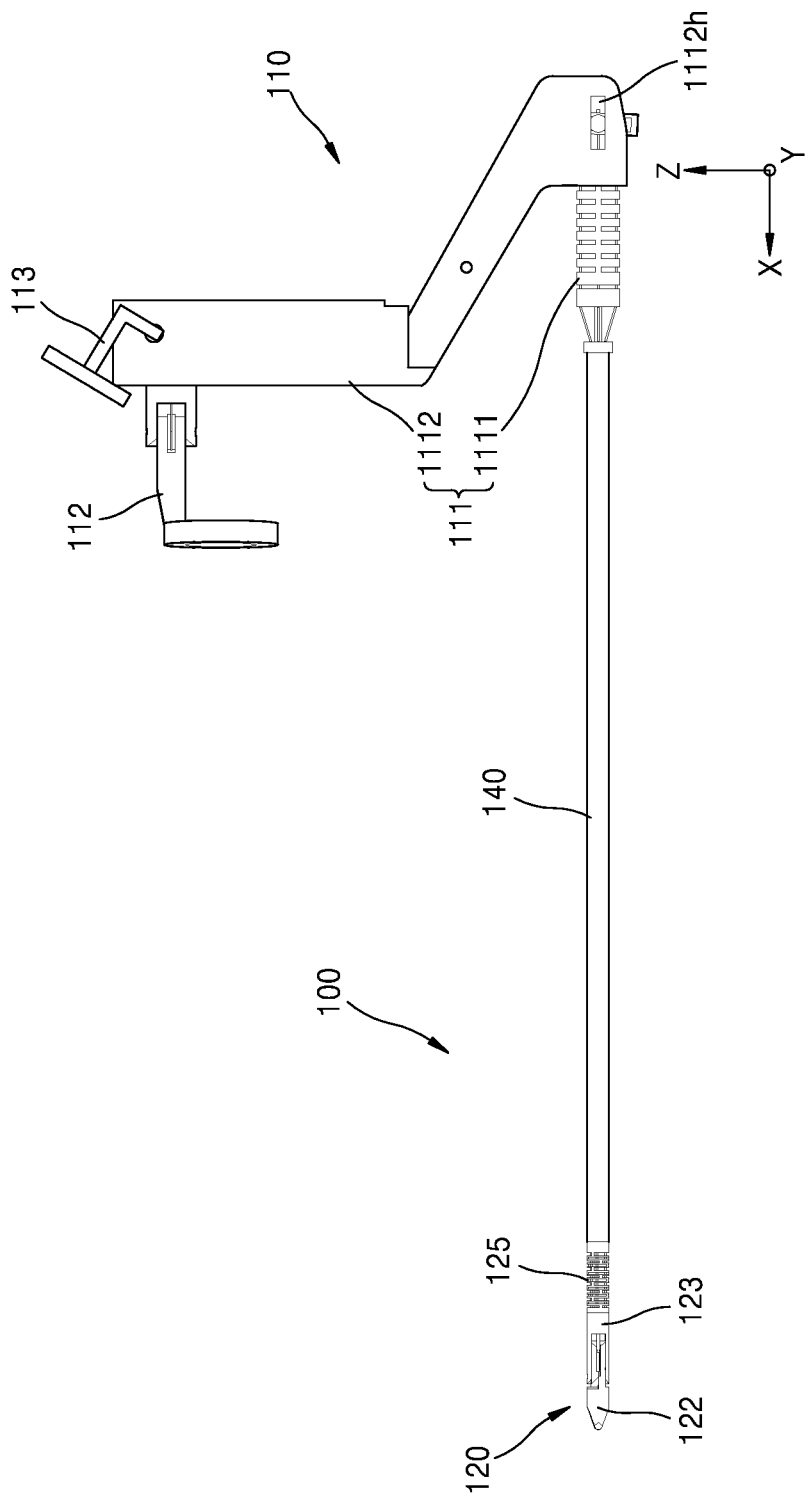
FIG. 2 is a side view of a surgical instrument (100) according to a first embodiment of the present invention.
Figure 3:
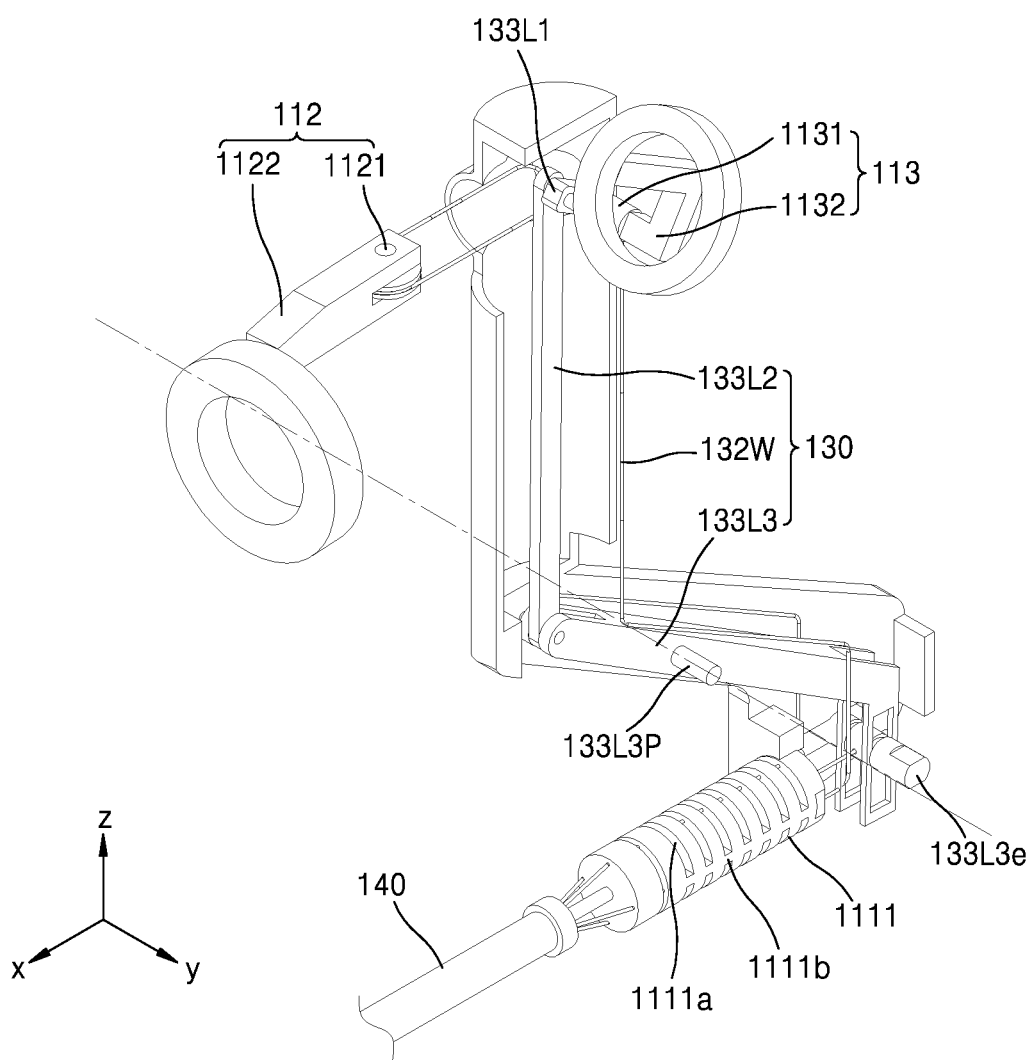
FIG. 3 is a detailed diagram showing an inner portion of the surgical instrument of FIG. 2.
Figure 4:
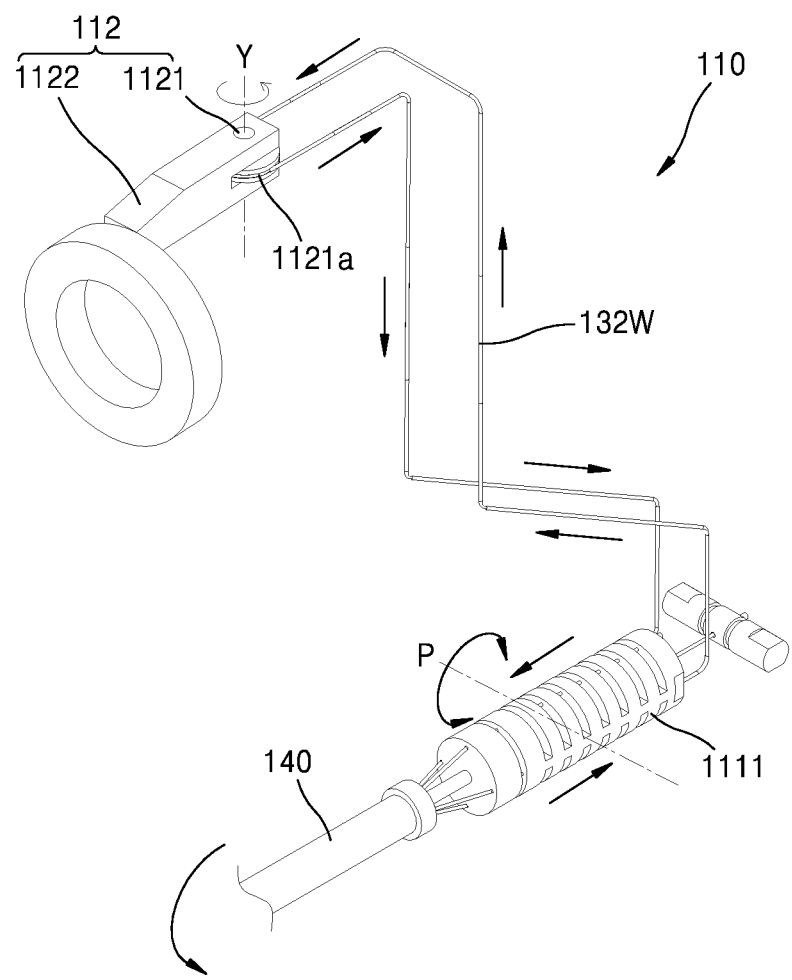
FIG. 4 is an internal detailed diagram of a yaw operator (112) of the surgical instrument (100) of FIG. 3.
Figure 5:
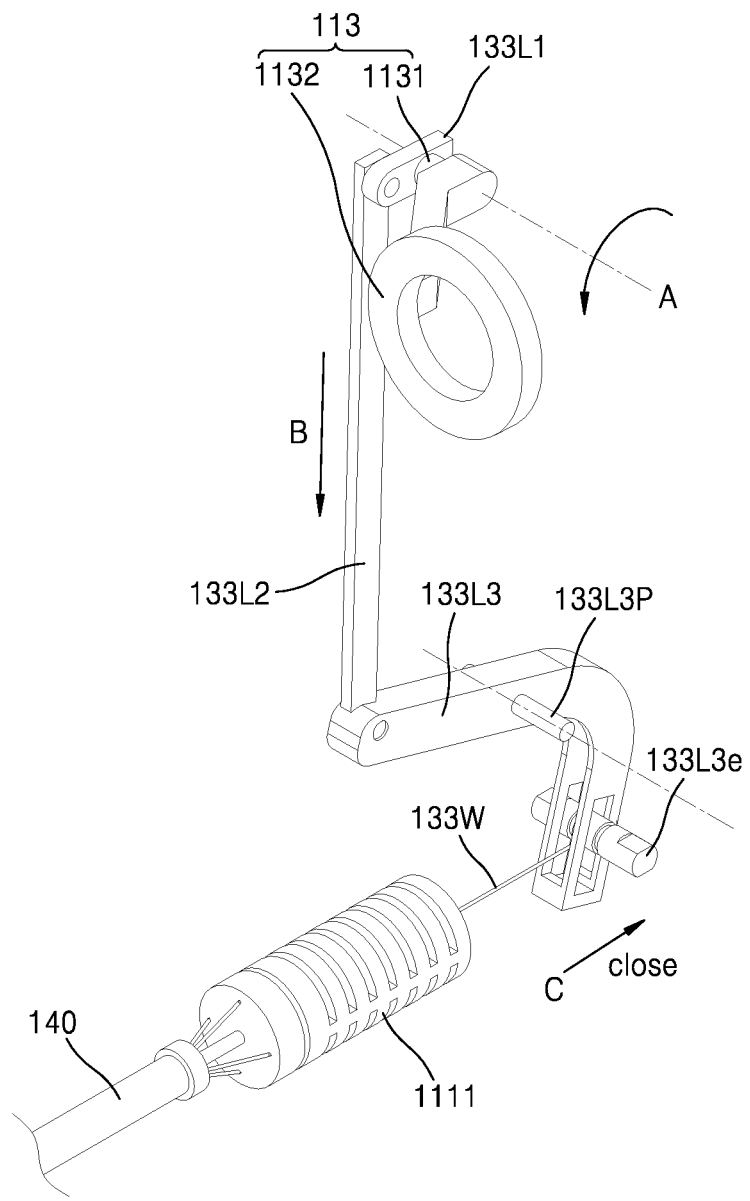
FIG. 5 is an internal detailed diagram of an actuation operator (112) of the surgical instrument (100) of FIG. 3.

FIG. 2 is a side view of a surgical instrument 100 according to a first embodiment, FIG. 3 is an internal detailed diagram of the surgical instrument 100 of FIG. 2, FIG. 4 is an internal detailed diagram of a yaw operator 112 of the surgical instrument 100 of FIG. 3, and FIG. 5 is an internal detailed diagram of an actuation operator 113 of the surgical instrument 100 of FIG. 3.

Referring to FIGS. 2 to 5, the surgical instrument 100 according to the first embodiment includes a manipulator 110, an end tool 120, a power transfer unit 130, and a connection unit 140. Here, the connection unit 140 is formed as a hollow shaft shape, in which one or more wires (will be described later) may be accommodated. In addition, the manipulator 110 is coupled to an end portion of the connection unit 140 and the end tool 120 is coupled to the other end portion so that the connection unit 140 connects the manipulator 110 to the end tool 120.

In detail, the manipulator 110 is provided at one end portion of the connection unit 140, and includes an interface that a doctor may directly manipulate, for example, an interface provided as forceps, a stick shape, a lever shape, etc. Thus, when the doctor manipulates the interface, the end tool 120 that is inserted into the body of a patient who is getting surgery operates to perform the surgery. Here, in FIG. 2, the manipulator 110 is formed as forceps, but the present invention is not limited thereto, that is, manipulators of various types that may be connected to the end tool 120 to manipulate the end tool 120 may be provided.

The end tool 120 is provided at the other end portion of the connection unit 140, and is inserted to a surgical site and performs necessary operations. As an example of the end tool 120, a pair of jaws (see 121 and 122 of FIG. 7A) for performing a grip operation may be used as shown in FIG. 2. However, the present invention is not limited thereto, but various devices for performing the surgery may be used as the end tool 120. For example, a one-armed cautery may be used as the end tool. The end tool 120 is connected to the manipulator 110 via the power transfer unit 130 to receive a driving power of the manipulator 110 through the power transfer unit 130, and then, performs operations required in surgery, e.g., grip, cutting, suturing, and etc.

Here, the end tool 120 of the surgical instrument 100 according to the first embodiment of the present invention is provided to be capable of rotating in at least two directions, for example, the end tool 120 may be formed to perform a pitch operation about a Y-axis of FIG. 2, and at the same time, to perform a yaw operation and an actuation operation about a Z-axis of FIG. 2. This will be described in detail later.

The power transfer unit 130 connects the manipulator 110 and the end tool 120 to each other to transfer the driving power of the manipulator 110 to the end tool 120, and may include a plurality of wires, pulleys, links, joints, gears, etc.

Hereinafter, the manipulator 110, the end tool 120, the power transfer unit 130, etc. of the surgical instrument 100 of FIG. 2 will be described in detail below.

(Manipulator)

Referring to FIGS. 2 to 5, the manipulator 110 of the surgical instrument 100 according to the first embodiment of the present invention includes a pitch operator 111 controlling a pitch movement of the end tool 120, a yaw operator 112 controlling a yaw movement of the end tool 120, and an actuation operation 130 controlling an actuation movement of the end tool 120.

As an exemplary utilization of the surgical instrument 100 of FIG. 2, a user may rotate a pitch operation grip 1112 in a state of gripping the pitch operation grip 1112 of the pitch operator 111 with his/her palm to perform the pitch movement, may rotate the yaw operator 112 in a state where the index finger is inserted to the yaw operator 112 to perform the yaw movement, and may rotate the actuation operator 113 in a state where the thumb finger is inserted to the actuation operator 113 to perform the actuation movement.

Here, the pitch operation, the yaw operation, and the actuation operation used in the present invention may be defined as follows:

First, the pitch operation denotes a vertical movement with respect to an extension direction of the connection unit 140 (X-axis direction in FIG. 2), that is, an operation of rotating about the Y-axis of FIG. 2. In other words, the pitch operation denotes a vertical rotation of the end tool 120 extending in the extension direction of the connection unit 140 (X-axis direction of FIG. 2) about the Y-axis. Next, the yaw operation denotes a movement in the left-and-right direction with respect to the extension direction of the connection unit 140 (X-axis direction of FIG. 2), that is, a rotating movement about the Z-axis of FIG. 2. That is, the yaw operation denotes a rotating movement of the end tool 120 extending in the extension direction (X-axis direction of FIG. 2) of the connection unit 140 in the left-and-right direction based on the Z-axis. In addition, the actuation operation denotes a folding or unfolding operation of two jaws (see 121 and 122 of FIG. 7A), when the two jaws rotate in opposite directions about the same rotating axis as that of the yaw operation. That is, the actuation operation denotes the rotation of the two jaws (see 121 and 122 of FIG. 7A) formed at the end tool 120 in opposite directions about the Z-axis.

Here, when the manipulator 110 of the surgical instrument 100 according to the first embodiment of the present invention is rotated in one direction, the end tool 120 rotates in a direction that is intuitively identical to the manipulation direction of the manipulator 110. In other words, when the pitch operator 111 of the manipulator 110 is rotated in one direction, the end tool 120 also rotates in a direction intuitively identical to the above direction to perform a pitch movement, and when the yaw operator 112 of the manipulator 110 is rotated in one direction, the end tool 120 also rotates in a direction that is intuitively identical to the above direction to perform the yaw movement. Here, the intuitively identical direction denotes that a movement direction of an index finger of the user gripping the manipulator 110 is substantially the same as a movement direction of the end portion of the end tool 120. The identical direction may not be an exactly identical direction on a three-dimensional (3D) coordinate system, for example, it may be appreciated that when the index finger of the user moves to the left, the end portion of the end tool 120 also moves to the left, and when the index finger of the user moves to the right, the end portion of the end tool 120 also moves to the right.

In addition, to this end, the surgical instrument 100 according to the first embodiment of the present invention is characterized in that the manipulator 110 and the end tool 120 are formed in the same direction with respect to a plane that is perpendicular to an extension axis (X-axis) of the connection unit 140. That is, in view of a YZ plane of FIG. 2, the manipulator 110 extends in a +X-axis direction, and at the same time, the end tool 120 also extends in the +X-axis direction. In other words, a direction in which the end tool 120 is formed at one end portion of the connection unit 140 and a direction in which the manipulator 110 is formed at the other end portion of the connection unit 140 may be the same as each other based on the YZ plane. In other words, it may be understood that the manipulator 110 is formed away from a body of the user gripping the manipulator 110, that is, in a direction in which the end tool 120 is formed.

In detail, in the surgical instrument according to the related art, since the manipulation direction of the manipulator by the user is different from and is not intuitively identical to an actual operation direction of the end tool, a surgical operator has difficulty in performing an intuitive operation and it takes the surgical operator a long time to skillfully move the end tool in a desired direction, and in some cases, a wrong operation occurs, and thus damaging a patient.

To address the above problem, the surgical instrument 100 according to the first embodiment of the present invention is configured so that the manipulation direction of the manipulator 110 and the operation direction of the end tool 120 are intuitively identical to each other, and to do this, the manipulator 110 and the end tool 120 are formed at the same side based on the YZ plane including a pitch operating joint 1111. This will be described below in more detail.

Referring to FIGS. 2 to 5, the manipulator 110 of the surgical instrument 100 according to the first embodiment of the present invention includes a pitch operator 111 controlling a pitch movement of the end tool 120, a yaw operator 112 controlling a yaw movement of the end tool 120, and an actuation operation 130 controlling an actuation movement of the end tool 120.

The pitch operator 111 includes a pitch operating joint 1111 and a pitch operating grip 1112. Here, the pitch operating joint 1111 may be formed to be rotatable about the Y-axis, and the pitch operating grip 1112 is connected to the pitch operating joint 1111 to be rotatable with the pitch operating joint 1111. Here, since the pitch operating joint is a curved type joint, when the pitch operating grip is rotated about the Y-axis, the pitch operating joint is curved or bent accordingly. However, bending of the pitch operating joint will be expressed as rotating of the pitch operating joint for convenience of description.

For example, when the user grips and rotates the pitch operating grip 1112, the pitch operating joint 1111 connected to the pitch operating grip 1112 rotates along with the pitch operating grip 1112, and then, the rotating force is transmitted to the end tool 120 via the power transfer unit 130 to make the end tool 120 rotate in the same direction as the rotating direction of the pitch operating joint 1111. That is, when the pitch operator 111 rotates in the clockwise direction around the pitch operating joint 1111, the end tool 120 also rotates in the clockwise direction around an axis parallel to that of the pitch operating joint 1111, and when the pitch operator 111 rotates in the counter-clockwise direction around the pitch operating joint 1111, the end tool 120 also rotates in the counter-clockwise direction around the axis parallel to that of the pitch operating joint 1111.

Here, the pitch operating joint 1111 may be a curved type joint member. In detail, the pitch operating joint 1111 is formed as a hollow cylinder shape, and a plurality of recesses 1111a are formed in an outer circumferential surface thereof in a direction (X-axis direction of FIG. 2) so that the pitch operating joint 1111 may be curved. Here, a rib 1111b is formed at a center portion of each of the recesses 1111a for determining a curvature direction of the pitch operating joint 1111. That is, at a portion where the rib 1111b is formed, the curvature is not performed, and the curvature of the pitch operating joint 1111 is performed at the portion where the rib 1111b is not formed. That is, as shown in FIG. 2, since the ribs 1111b are formed along opposite side surfaces of the pitch operating joint 1111, the pitch operating joint 1111 may be curved upward or downward where the ribs 1111b are not formed. Therefore, although an actual rotating axis does not exist in the pitch operating joint 1111, it may be assumed that the pitch operating joint 1111 rotates in an up-and-down direction about a P-axis of FIG. 4. Therefore, the pitch operating joint 1111 is formed as a curved type joint member, and becomes a rotating center of the pitch movement.

In addition, the yaw operator 112 and the actuation operator 113 are formed at one end portion of the pitch operating grip 1112 of the pitch operator 111. Therefore, when the pitch operator 111 rotates about the pitch operating joint 1111, the yaw operator 112 and the actuation operator 113 also rotate along with the pitch operator 111.

As such, a coordinate system of the yaw operator 112 and the actuation operator 113 is not fixed, but relatively changes according to the rotation of the pitch operator 111. That is, in FIG. 2, a yaw operating axis 1121 of the yaw operator 112 is in parallel to the Z-axis, and an actuation operating axis 1131 of the actuation operator 113 is in parallel with the Y-axis. However, when the pitch operator 111 rotates, the yaw operating axis 1121 of the yaw operator 112 and the actuation operating axis 1131 of the actuation operator 113 are not parallel with the Z-axis and the Y-axis. That is, the coordinate system of the yaw operator 112 and the actuation operator 113 has changed according to the rotation of the pitch operator 111. However, in the present specification, the coordinate system of the yaw operator 112 and the actuation operator 113 will be described on the assumption that the pitch operating grip 1112 is perpendicular to the connection unit 140 as shown in FIG. 2, for the convenience of the description.

The yaw operator 112 includes the yaw rotating axis 1121 and a yaw rotating member 1122. Here, the yaw rotating axis 1121 may be formed to be at a predetermined angle with respect to an XY plane where the connection unit 140 is formed. For example, the yaw rotating axis 1121 may be formed in a direction parallel to the Z-axis as shown in FIG. 2, and in this state, when the pitch operator 111 rotates, the coordinate system of the yaw operator 112 may be relatively changed as described above. However, the present invention is not limited thereto, and the yaw rotating axis 1121 may be formed in various directions by ergonomic design according to the structure of a hand of the user gripping the yaw operator 112.

The yaw rotating member 1122 is connected to the yaw rotating axis 1121 to rotate along with the yaw rotating axis 1121. For example, when the user holds and rotates the yaw rotating member 1122 with the index finger, the yaw rotating axis 1121 connected to the yaw rotating member 1122 rotates along with the yaw rotating member 1122, and the rotating force is transmitted to the end tool 120 via the power transfer unit 130 so that two jaws (see 121 and 122 of FIG. 7A) of the end tool 120 rotate in the left-and-right direction, e.g., the same direction as the rotating direction of the yaw rotating axis 1121. To do this, a pulley 1121a may be formed at the yaw rotating axis 1121. In addition, a yaw wire 132W may be connected to the pulley 1121a. The yaw wire 132W is connected to a joint member 125 of the end tool 120, wherein the joint member 125 will be described later with reference to FIG. 7A, to rotate the joint member 125.

The actuation operator 113 includes an actuation rotating axis 1131 and an actuation rotating member 1132. Here, the actuation rotating axis 1131 may be formed to be at a predetermined angle with respect to an XY plane where the connection unit 140 is formed. For example, the actuation rotating axis 1131 may be formed in a direction parallel to the Y-axis as shown in FIG. 2, and in this state, when the pitch operator 111 rotates, the coordinate system of the actuation yaw operator 113 may be relatively changed as described above. However, the present invention is not limited thereto, and the actuation rotating axis 1131 may be formed in various directions by ergonomic design according to the structure of a hand of the user gripping the actuation operator 113.

In addition, the actuation rotating member 1132 is connected to the actuation rotating axis 1131 to rotate with the actuation rotating axis 1131. For example, when the user holds and rotates the actuation rotating member 1132 with the thumb finger, the actuation rotating axis 1131, to which the actuation rotating member 1132 is connected, rotates, and the rotating force is transmitted to the end tool 120 via the power transfer unit 130 so that two jaws (see 121 and 122 of FIG. 7A) of the end tool 120 perform the actuation movement. Here, the actuation movement denotes an operation of folding or unfolding the two jaws (see 121 and 122 of FIG. 7A) by rotating the two jaws (see 121 and 122 of FIG. 7A) in opposite directions, as described above. That is, when the actuation operator 113 is rotated in one direction, as a first jaw (see 121 of FIG. 7A) rotates in the counter-clockwise direction and a second jaw (see 122 of FIG. 7A)

rotates in the clockwise direction, the end tool 120 is closed. On the other hand, when the actuation operator 113 is rotated in the opposite direction, as the first jaw (see 121 of FIG. 7A) rotates in the clockwise direction and the second jaw (see 122 of FIG. 7A) rotates in the counter-clockwise direction, the end tool 120 is open.

In addition, a first actuation link 133L1 may be connected to an end portion of the actuation rotating axis 1131, a second actuation link 133L2 may be connected to an end portion of the first actuation link 133L1, and a third actuation link 133L3 may be connected to an end portion of the second actuation link 133L2. Here, a pivot point 133L3P is formed at the third actuation link 133L3 so as to perform as a central point of the movement of the third actuation link 133L3. In addition, a guide protrusion 133L3e is formed at an end portion of the third actuation link 133L3, and a guide recess 1112h may be formed in the pitch operating grip 1112.

Therefore, when the actuation rotating axis 1131 rotates, the first actuation link 133L1 connected to the actuation rotating axis 1131 rotates, and when the first actuation link 133L1 rotates, the second actuation link 133L2 connected to the first actuation link 133L1 moves up and down in the Z-axis direction. In addition, when the second actuation link 133L2 moves up and down in the Z-axis direction, the third actuation link 133L3 connected to the second actuation link 133L2 rotates about the pivot point 133L3P, and thus, the guide protrusion 133L3e of the third actuation link 133L3 linearly moves along the guide recess 1112h of the pitch operating grip 1112 in the X-axis direction. In addition, an actuation wire 133W is connected to the guide protrusion 133L3e of the third actuation link 133L3, and thus, when the guide protrusion 133L3e linearly moves in the X-axis direction, the actuation wire 133W also linearly moves in the X-axis direction. In addition, the actuation wire 133W is connected to an actuation guide pin 133WG of the end tool 120, which will be described later with reference to FIGS. 7A to 7C, to control the actuation movement of the jaws 121 and 122.

Referring to FIGS. 2 to 5, in the surgical instrument 100 according to the first embodiment of the present invention, the pitch operator 111 and the end tool 120 are formed coaxially or on axes parallel with each other (X-axis). That is, the pitch operating joint 1111 of the pitch operator 111 is formed at an end portion of the connection unit 140, and the end tool 120 is formed at the other end portion of the connection unit 140. Here, although the connection unit 140 is formed straight in the drawings, but the present invention is not limited thereto. That is, the connection unit 140 may be curved to have a predetermined curvature rate or bent once or more if necessary, and in this case, it may be understood that the pitch operator 111 and the end tool 120 are formed substantially on the same or parallel axis. In addition, although the pitch operator 111 and the end tool 120 are shown to be formed at the same axis (X-axis) in FIG. 2, but the present invention is not limited thereto, and the pitch operator 111 and the end tool 120 may be formed on different axes from each other. This will be described later.

FIGS. 6A to 6D are diagrams of various modified examples of the manipulator 110 of the surgical instrument 100 according to the first embodiment of the present invention.

Figure 6A:
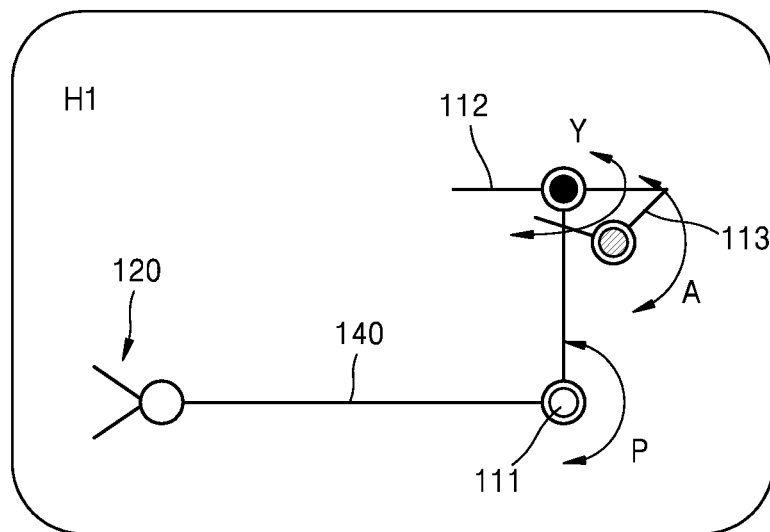
FIG. 6A is a conceptual diagram of a manipulator of the surgical instrument (100) of FIG. 1.

As for H1 of FIG. 6A, as described above with reference to FIG. 2, etc., the pitch operator 111 and the yaw operator 112 of the manipulator 110 are formed independently from each other, and thus, the pitch operator 111 and the yaw operator 112 are functionally distinguished from each other. H1 may be seen in the first, second, and third embodiments of the present invention.

Figure 6B:
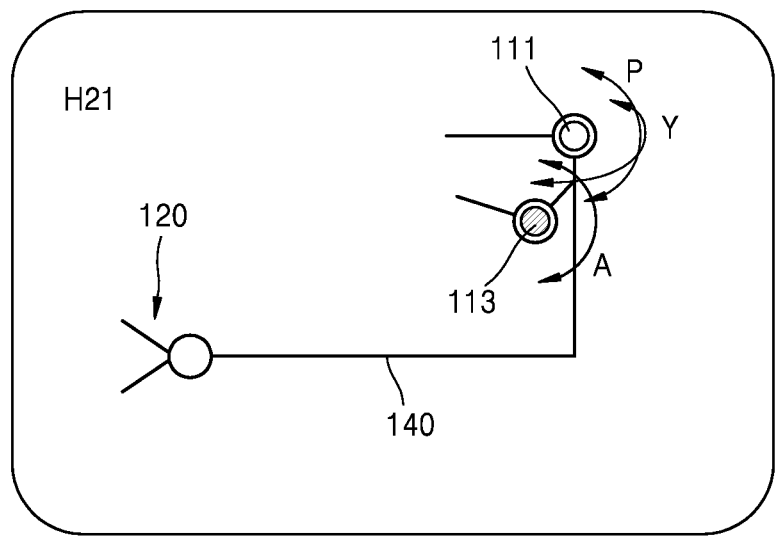
FIGS. 6B, 6C, and 6D are diagrams of various modified examples of a manipulator (110) of the surgical instrument (100) according to the first embodiment of the present invention.

As for H21 of FIG. 6B, 1) a pitch/yaw operator 411 in which a pitch operator and a yaw operator are integrally formed is provided in a manipulator 410 in order to perform functions of both the pitch operator and the yaw operator. 2) Here, the pitch/yaw operator 411 is formed above an extension line of an end tool 420. 3) In addition, an actuation operator 413 is formed on the pitch/yaw operator 411 so as to independently rotate on the pitch/yaw operator 411. H21 may be seen in the fourth embodiment of the present invention.

Figure 6C:
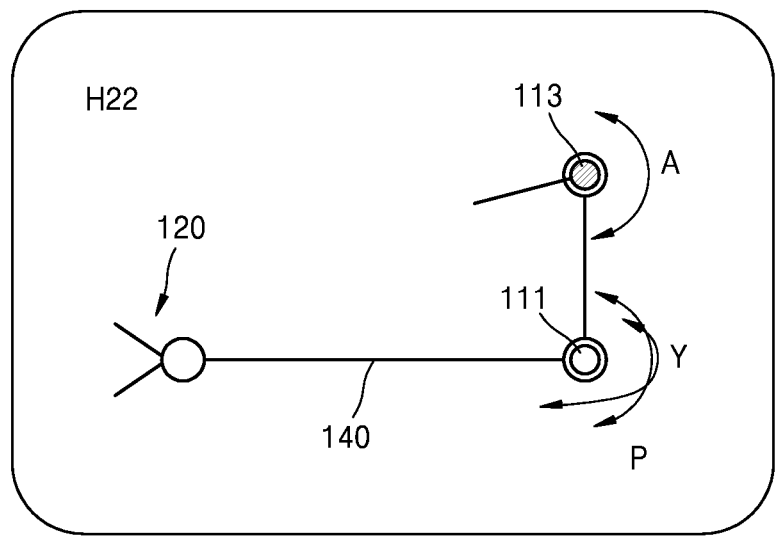

As for H22 of FIG. 6C, 1) a pitch/yaw operator 511 in which a pitch operator and a yaw operator are integrally formed is provided in a manipulator 510 in order to perform functions of both the pitch operator and the yaw operator. 2) Here, the pitch/yaw operator 511 is formed on an extension line of an end tool 520. 3) In addition, an actuation operator 513 is formed on the pitch/yaw operator 511 to rotate with the pitch/yaw operator 511 when the pitch/yaw operator 511 rotates, and is provided to independently rotate on the pitch/yaw operator 511. H22 may be seen in the fifth, sixth, and seventh embodiments of the present invention.

Figure 6D:
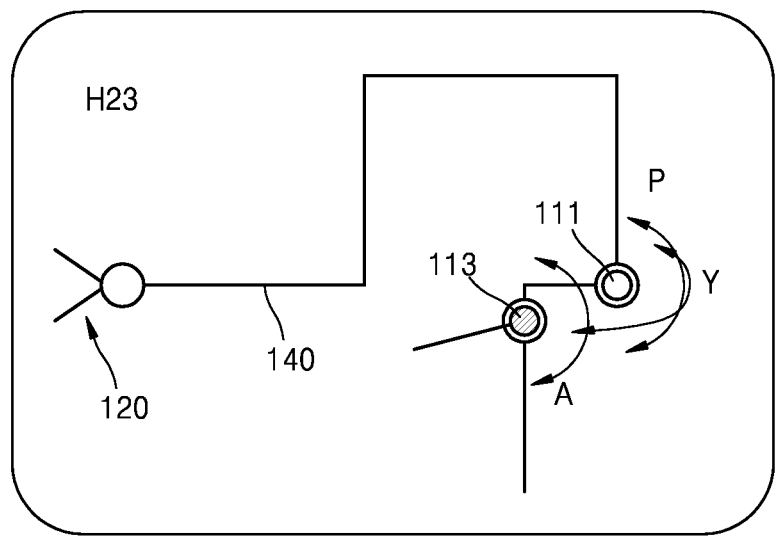

As for H23 of FIG. 6D, 1) a pitch/yaw operator 811 in which a pitch operator and a yaw operator are integrally formed is provided in a manipulator 810 in order to perform functions of both the pitch operator and the yaw operator. 2) In addition, the pitch/yaw operator 811 is formed on an extension line of an end tool 820, and a connection unit 840 is not straight, but is bent at least once. 3) In addition, an actuation operator 813 is formed on the pitch/yaw operator 811 to rotate with the pitch/yaw operator 811 when the pitch/yaw operator 811 rotates, and is provided to independently rotate on the pitch/yaw operator 811. H23 may be seen in the eighth, ninth, and tenth embodiments of the present invention.

Also, various modified examples of the manipulator including the above modified examples may be applied to the surgical instrument according to the present invention.

(End Tool)—Curved Type

Figure 7A:
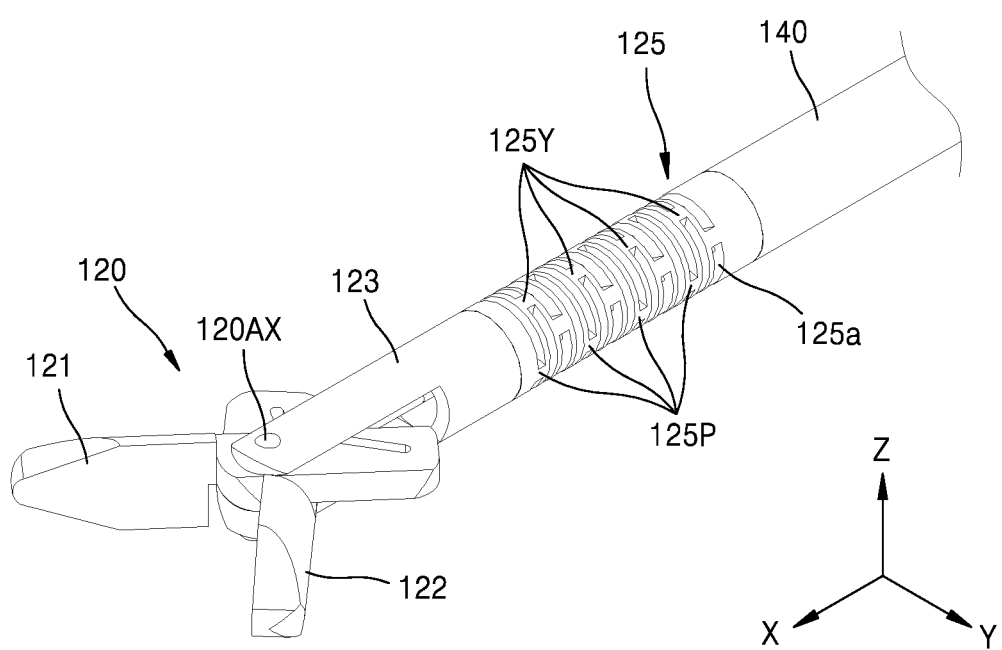
FIG. 7A is a coupling perspective view of an end tool applied to the surgical instrument (100) of FIG. 2.
Figure 7B:
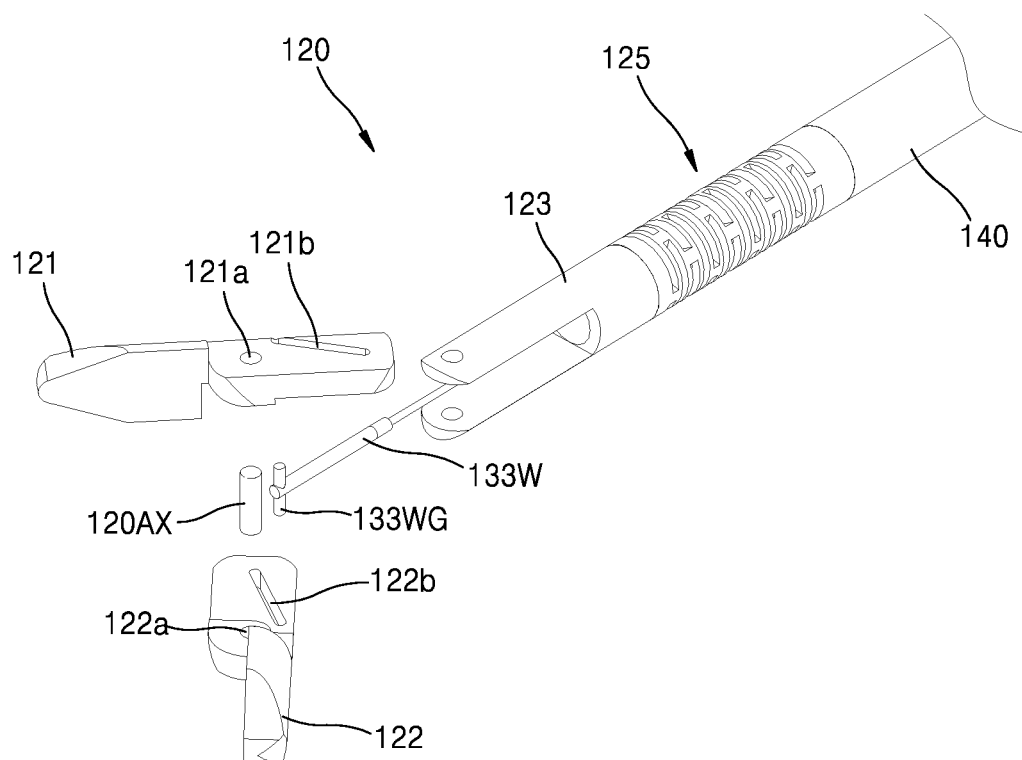
FIG. 7B is an exploded perspective view of the end tool of FIG. 7A.
Figure 7C:
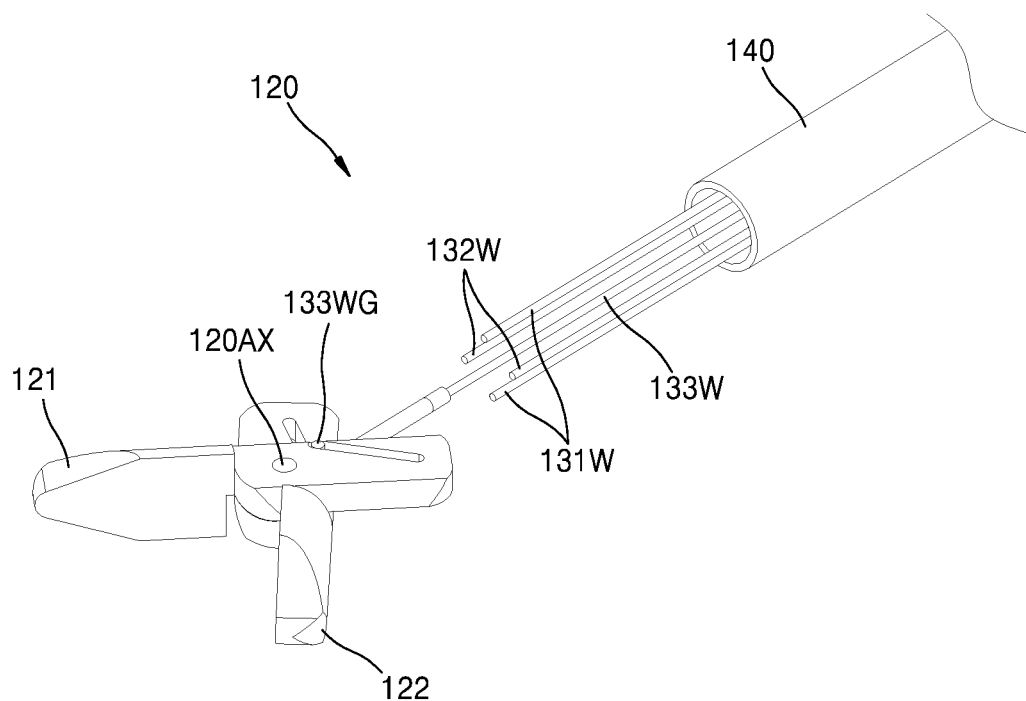
FIG. 7C is a perspective view of the end tool of FIG. 7A, from which a jaw base (123) and a joint member (125) are omitted.
Figure 7D:
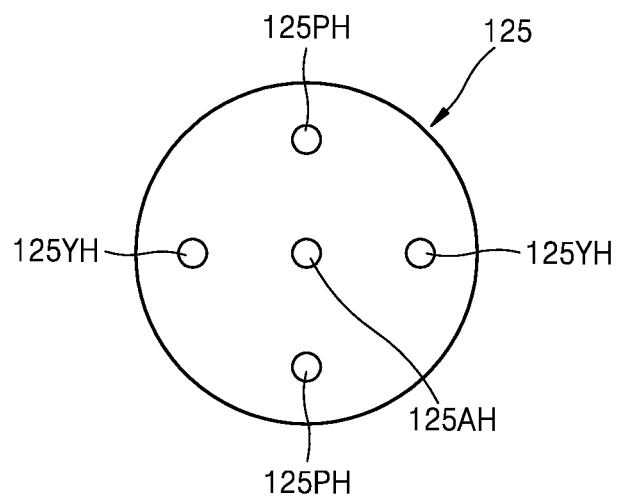
FIG. 7D is a front view of the joint member (125) of the end tool of FIG. 7A.

FIG. 7A is a coupling perspective view of an end tool applied to the surgical instrument 100 according to the first embodiment, FIG. 7B is an exploded perspective view of the end tool of FIG. 7A, FIG. 7C is a perspective view showing the end tool of FIG. 7A, from which a jaw base 123 and a joint member 125 are omitted, and FIG. 7D is a front view of the joint member 125 of the end tool of FIG. 7A.

Referring to FIGS. 7A to 7D, the end tool 120 applied to the surgical instrument 100 according to the first embodiment of the present invention adopts a curved type joint member as the joint member 125. That is, the end tool 120 includes the first jaw 121, the second jaw 122, the jaw base 123, and the joint member 125. In addition, the power transfer unit 130 applied to the surgical instrument 100 according to the first embodiment of the present invention includes one or more pitch wires 131W, one or more yaw wires 132W, and an actuation wire 133W.

In the present embodiments, the pitch operation is performed via the moving of the pitch wire connected to the joint member, and the yaw operation is performed via the moving of the yaw wire connected to the joint member. Here, the actuation wire extends towards the end tool across among the pitch wires and the yaw wires, and is connected to a recess formed in each of the two jaws. In addition, the actuation operation, that is, folding and unfolding of the two jaws, is performed by pushing and pulling of the actuation wires. Here, since the actuation wire is provided at the center across between the pitch wires and the yaw wires, moving of the pitch wires and the yaw wires in the pitch operation and the yaw operation do not affect the actuation wire.

In addition, when the pitch operation is performed as lengths of the pitch wires at opposite sides are differentiated from each other, the yaw wire crossing the center between the opposite pitch wires is not affected by the pitch operation, and likewise, when the yaw operation is performed as lengths of the yaw wires at opposite sides are differentiated from each other, the pitch wire crossing the center between the opposite yaw wires is not affected by the yaw operation. This will be described in more detail later.

A whole structure of the end tool 120 will be described in detail.

In detail, the joint member 125 is formed at an end portion of the connection unit 140. Here, the surgical instrument according to the first embodiment of the present invention may use the curved type joint member as the joint member 125 of the end tool 120. That is, in the present embodiment, the joint member 125 is configured by using the curved type joint member for performing the pitch operation and the yaw operation.

The joint member 125 formed as the curved type has a hollow cylinder shape, and a plurality of recesses 125a are formed in an outer circumferential surface in a direction (X-axis direction of FIG. 7A) to be curved. Here, first ribs 125P and second ribs 125Y for guiding a curved direction of the joint member 125 are formed at a center in each of the recesses 125a. That is, the joint member is not curved at the portions where the ribs 125P and 125Y are formed, but is mainly curved at portions where the ribs 125P and 125Y are not formed.

Here, the first ribs 125P for guiding the curve of the joint member 125 in a first direction (e.g., the pitch movement) and the second ribs 125Y for guiding the curve of the joint member 125 in a second direction (e.g., the yaw movement) are formed in the joint member 125. Here, the second ribs 125Y may be offset a predetermined degree with respect to the first ribs 125P. In addition, the first ribs 125P and the second ribs 125Y may be alternatively formed in a manner that the first ribs 125P are formed in even-numbered recesses 125a and the second ribs 125Y are formed in odd-numbered recesses 125a.

That is, in FIG. 7A, the first ribs 125P are formed along opposite sides of the joint member 125, and thus, the joint member 125 may be curved in the up-and-down direction. Therefore, although an actual rotating axis does not exist in the joint member 125, it may be assumed that the joint member 125 rotates in an up-and-down direction about the Y-axis of FIG. 7A. Therefore, the joint member 125 may become the rotating center of the pitch movement.

In addition, since the second ribs 125Y are formed along upper and lower surfaces of the joint member 125, the joint member 125 may be curved in the left-and-right direction. Therefore, although an actual rotating axis does not exist in the joint member 125, it may be assumed that the joint member 125 rotates in the left-and-right direction about the Z-axis of FIG. 7A. Therefore, the joint member 125 may become the rotating center of the yaw movement. Here, the first ribs 125P and the second ribs 125Y do not have to be formed on a vertical plane or a horizontal plane of the joint member 125, but may be offset a predetermined degree from the vertical plane or the horizontal plane of the joint member 125.

In addition, opposite ends of the pitch wires 131W and the yaw wires 132W are respectively coupled to the end portions of the joint member 125 at the sides of the first and second jaws 121 and 122. Therefore, when an end portion of the pitch wire 131W is pulled, an end portion of the joint member 125 connected to the pitch wire 131W is also pulled, and thus, the joint member 125 rotates about the Y-axis of FIG. 7A to perform the pitch movement. Likewise, when an end portion of the yaw wire 132W is pulled, an end portion of the joint member 125 connected to the yaw wire 132W is also pulled, and thus, the joint member 125 rotates about the Z-axis of FIG. 7A to perform the yaw movement.

In addition, pitch wire through holes 125PH, yaw wire through holes 125YH, and an actuation wire through hole 125AH are formed at an end portion (not shown) of the connection unit 140 and an end portion of the joint member 125 facing the end portion of the connection unit. In addition, the pitch wires 131W extend from the connection unit 140 to the end tool 120 through the pitch wire through hole 125PH and are coupled to the other end portion of the joint member 125. In addition, the yaw wires 132W extend from the connection unit 140 to the end tool 120 through the yaw wire through hole 125YH and are coupled to the other end portion of the joint member 125. Also, the actuation wire 133W extends from the connection unit 140 to the end tool 120 through the actuation wire through hole 125AH. In addition, the actuation wire 133W that has passed through the actuation wire through hole 125AH is connected to the actuation guide pin 133WG.

Here, the pitch wire through holes 125PH are formed at opposite end portions of the diameter of the joint member 125 in the Z-axis direction as shown in FIG. 7D to control the pitch movement. In addition, the yaw wire through holes 125YH are formed at opposite end portions of the diameter of the joint member 125 in the Y-axis direction as shown in FIG. 7D to control the yaw movement. In addition, the actuation wire 125AH is formed at the center of the joint member 125 as shown in FIG. 7D to control the actuation movement.

As described above, the yaw movement is performed by pulling one of the opposite yaw wires, and at this time, lengths of the actuation wire and the pitch wire passing through the center between the opposite yaw wires are not changed, and thus, the yaw operation is independently performed from the actuation operation and the pitch operation. Likewise, the pitch operation is performed by pulling one of the opposite pitch wires, and at this time, lengths of the actuation wire and the yaw wire passing through the center between the opposite pitch wires are not changed, and thus, the pitch operation is independently performed from the actuation operation and the yaw operation.

In addition, axis through holes 121a and 122a are respectively formed in the first and second jaws 121 and 122, and an actuation axis 120AX is inserted through the axis through holes 121a and 122a of the first and second jaws 121 and 122. The first and second jaws 121 and 122 rotate about the actuation axis 120AX.

In addition, guide holes 121b and 122b are formed at one sides of the axis through holes 121a and 122a of the first and second jaws 121 and 122, and the actuation guide pin 133WG is inserted through the guide holes 121b and 122b of the first and second jaws 121 and 122. The actuation wire 133W is coupled to the actuation guide pin 133WG, and when the actuation wire 133W reciprocates along the X-axis, the actuation guide pin 133WG connected to the actuation wire 133W reciprocates along the guide hole 121b. Accordingly, the first jaw 121 and the second jaw 122 rotate about the actuation axis 120AX to perform the actuation operation. That is, the actuation operation, in which two jaws are folded or unfolded simultaneously, may be performed by one actuation wire going forward or backward.

As described above, the end tool 120 of the surgical instrument 100 according to the first embodiment separately include the wire for the pitch operation, the wire for the yaw operation, and the wire for the actuation operation, so that one operation may not affect the other operations.

First, the yaw operation according to the present embodiment will be described below.

Figure 8:
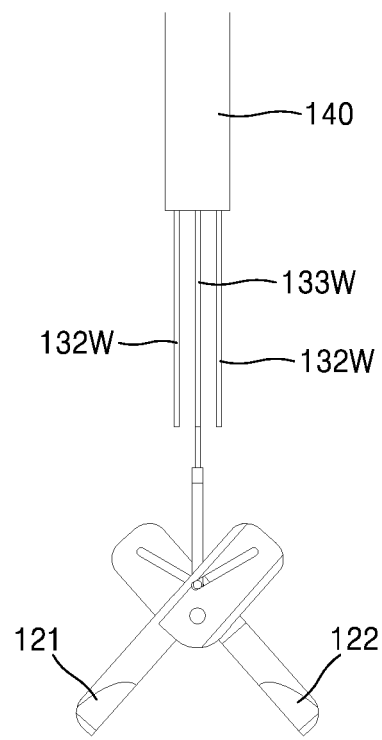
FIGS. 8 and 9 are perspective views showing the end tool of FIG. 7A performing a yaw operation.
Figure 9:
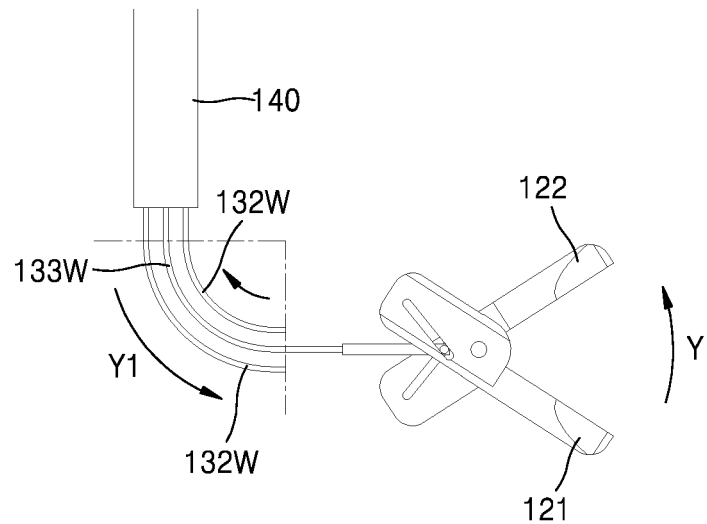

Referring to FIGS. 4, 8, and 9, the yaw wire 132W of the end tool 120 for performing the yaw operation connects the yaw operator 112 of the manipulator 110 to the joint member 125 of the end tool 120. Therefore, when the yaw operator 112 rotates in the counter-clockwise direction about the yaw rotating axis 1121, the yaw wire 132W at the side of the manipulator 110 is entirely moved in an arrow direction in FIG. 4, and accordingly, between the yaw wires 132W at the end tool 120 side, the yaw wire 132W at the left side in FIG. 8 is pushed towards the end tool from the manipulator and the yaw wire 132W at the right side is pulled to move in a direction denoted by the arrow Y1 in FIG. 9. Thus, the joint member 125 connected to the yaw wire 132W and the first and second jaws 121 and 122 connected to the joint member 125 rotate in a direction denoted by the arrow Y in FIG. 9 about the joint member 125 to perform the yaw operation. That is, when the yaw operator 112 rotates in a direction about the yaw rotating axis 1121, the joint member 125 of the end tool 120 and the first and second jaws 121 and 122 connected to the joint member 125 also rotate in the same direction, and accordingly, the manipulating direction of the manipulator 110 and the operating direction of the end tool 120 are intuitively identical to each other.

Next, the pitch operation according to the present embodiment will be described below.

Like the above-described yaw operation, the pitch wires 131W for performing the pitch operation of the end tool 120 connect the pitch operation (see 111 of FIG. 2) of the manipulator (see 110 of FIG. 2) to the joint member 125 of the end tool 120. Therefore, when the pitch operator (see 111 of FIG. 2) rotates about the pitch operating joint (see 1111 of FIG. 2), the pitch wires 131W connected to the pitch operator rotates, and accordingly, the joint member 125 connected to the pitch wires 131W and the first and second jaws 121 and 122 connected to the joint member 125 rotate about the joint member 125 to perform the pitch operation. That is, when the pitch operator (see 111 of FIG. 2) rotates in a direction about the pitch operating joint (see 1111 of FIG. 2), the joint member 125 of the end tool 120 and the first and second jaws 121 and 122 connected to the joint member 125 also rotate in the same direction, the manipulating direction of the manipulator 110 and the operating direction of the end tool 120 intuitively match with each other.

Next, the actuation movement according to the present embodiment will be described below.

Figure 10:
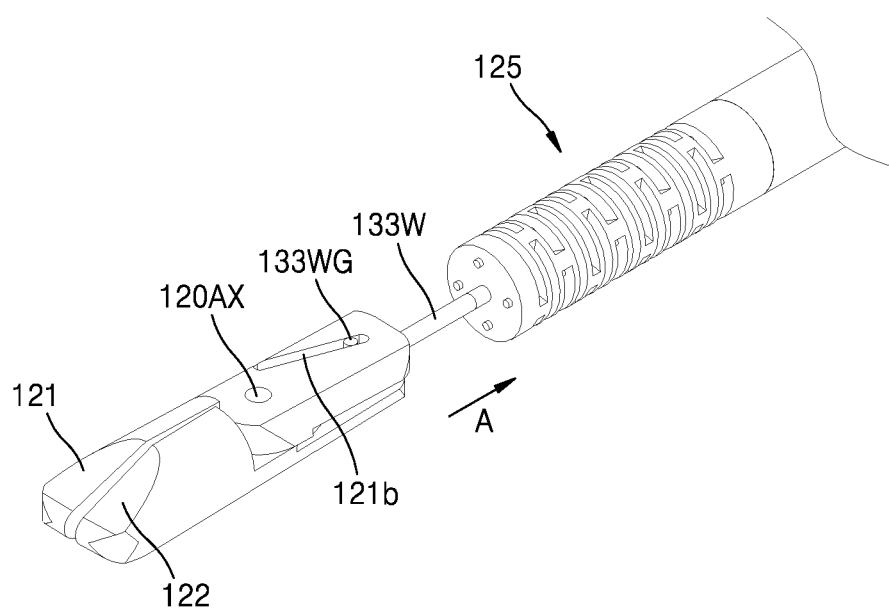
FIG. 10 is a perspective view of the end tool of FIG. 7A performing an actuation movement and being closed.

Referring to FIGS. 5 and 8, the actuation wire 133W for performing the actuation movement of the end tool 120 connects the actuation operator 113 of the manipulator 110 to the actuation guide pin 133WG of the end tool 120. Therefore, when the actuation operator 113 rotates in an arrow A direction of FIG. 5 about the actuation rotating axis 1131, the first actuation link 133L1, the second actuation link 133L2, and the third actuation link 133L3 that are sequentially connected to the actuation operator are respectively moved. Here, the pivot point 133L3P is formed at the third actuation link 133L3 so as to perform as a central point of the rotation of the third actuation link 133L3. In addition, when the third actuation link 133L3 rotates about the pivot point 133L3P as described above, the guide protrusion 133L3e of the third actuation link 133L3 linearly moves in an arrow C direction of FIG. 5, and the actuation wire 133W connected to the guide protrusion 133L3e linearly moves in the arrow A direction of FIG. 10 in a state as shown in FIG. 7A. Therefore, as the actuation guide pin 133WG connected to the actuation wire 133W moves along the guide holes 121b and 122b, the first and second jaws 121 and 122 rotate about the actuation axis 120AX, and then, the actuation operation of unfolding the first and second jaws 121 and 122 is performed.

Various modified examples of the end tool will be described later with reference to FIGS. 33 to 36.

Total Movements According to the First Embodiment

Hereinafter, total configurations of the pitch operation, the yaw operation, and the actuation operation of the surgical instrument 100 according to the first embodiment of the present invention will be summarized as follows, with reference to the above descriptions.

The pitch operation is as follows.

As described above, when the user holds and rotates the pitch operating grip 1112 of the pitch operator 111 in an arrow P (pitch) direction of FIG. 4 about the pitch operating joint 1111, the joint member 125 connected to the pitch operator 111 via the pitch wires 131W and the first and second jaws 121 and 122 connected to the joint member rotate about the Y-axis to perform the pitch operation. That is, when the pitch operator 111 rotates in a direction about the pitch operating joint 1111, the joint member 125 of the end tool 120 and the first and second jaws 121 and 122 connected to the joint member 125 also rotate in the same direction, and accordingly, the manipulating direction of the manipulator 110 and the operating direction of the end tool 120 match with each other intuitively.

Next, the yaw operation according to the present embodiment will be described below.

When the user holds and rotates the yaw rotating member 1122 in the arrow Y direction of FIG. 4 with the index finger, the yaw rotating member 1122 rotates about the yaw rotating axis 1121, and then, the rotating force rotates the joint member 125 connected to the yaw operator 112 via the yaw wires 132W and the jaws 121 and 122 connected to the joint member about the Z-axis to perform the yaw operation. That is, when the yaw operator 112 rotates in a direction about the yaw rotating axis 1121, the joint member 125 of the end tool 120 and the first and second jaws 121 and 122 connected to the joint member 125 also rotate in the same direction, and accordingly, the manipulating direction of the manipulator 110 and the operating direction of the end tool 120 are intuitively identical to each other.

Next, the actuation operation according to the present embodiment will be described below.

When the user holds and rotates the actuation rotating member 1132 in the arrow A direction of FIG. 5 with the thumb finger, the actuation rotating member 1132 rotates about the actuation rotating axis 1131, and thus, the first actuation link 133L1 connected to the actuation rotating axis 1131 rotates with the actuation rotating axis 1131 and the second actuation link 133L2 connected to the first actuation link 133L1 descends in the arrow B direction of FIG. 5. In addition, when the second actuation link 133L2 descends in the arrow B direction of FIG. 5, the third actuation link 133L3 connected to the second actuation link 133L2 rotates in the counter-clockwise direction along the pivot point 133L3P, and thus, the guide protrusion 133L3e of the third actuation link 133L3 linearly moves along the guide recess 1112h of the pitch operating grip 1112 in the X-axis direction along the arrow C of FIG. 5. Therefore, the actuation wire 133W connected to the guide protrusion 133L3e of the third actuation link 133L3 also linearly moves in the arrow C direction along the X-axis, and the actuation wire 133W makes the actuation guide pin (see 133WG of FIG. 7) of the end tool (see 120 of FIG. 7) linearly move and the first and second jaws 121 and 122 rotate in opposite directions to each other to perform the actuation operation of folding the jaws. On the contrary, when the actuation rotating member 1132 is rotated in the opposite direction to the arrow A of FIG. 5, the first and second jaws 121 and 122 rotate in the opposite direction to the above to perform the actuation operation of unfolding the jaws.

BEST MODE

Classification of the First, Second and Third Embodiments of the Surgical Instrument Hereinafter, before describing the surgical instrument according to the second and third embodiments, criteria for a classifying the first, second, and third embodiments of the surgical instrument according to the present invention will be described below.

Figure 11D:
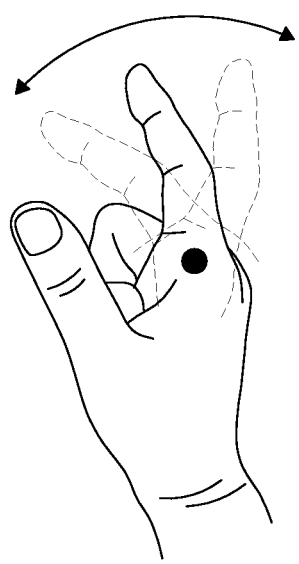
FIG. 11D is a schematic diagram of a yaw operation of the surgical instrument according to the first, second, and third embodiments of the present invention.

FIGS. 11A, 11B, and 11C are schematic diagrams illustrating pitch operation of the surgical instruments according to the first, second, and third embodiments of the present invention, and FIG. 11D is a schematic diagram of the yaw operation of the surgical instruments according to the first, second, and third operation of the present invention.

First, the yaw operations in the first, second, and third embodiments are described as follows.

According to the first, second, and third embodiments, the yaw movements are commonly performed by the index finger. That is, as shown in FIG. 11D, since the yaw movement in the first, second, and third embodiments is performed by the index finger, the pivot point is naturally located behind the moving part, and thus, the manipulating direction of the manipulator by the user and the actual operating direction of the end tool intuitively coincide with each other.

Next, the pitch operations according to the first, second, and third embodiments of the present invention will be described as follows. Here, the first, second, and third embodiments of the surgical instrument of the present invention are classified in view of locational relationship between of a virtual center line of the pitch operating grip in the Z-axis direction and a virtual center line of the pitch operating joint in the Z-axis direction.

Here, "the virtual center line X2 of the pitch operating joint in the Z-axis direction" denotes a virtual axis in the Z-axis direction, which perpendicularly meets a rough center point of the pitch operating joint that is not in curved state in the X-axis direction, or an axis that is perpendicular to a virtual rotating center of the pitch operating joint in the Y-axis direction on a YZ plane including a virtual rotating center axis of the pitch operating joint in the Y-axis direction. Hereinafter, the above axis will be referred to as "a virtual center axis of the pitch operating joint in the Z-axis direction".

Referring to FIG. 11A, according to the surgical instrument of the first embodiment, the virtual center axis of the pitch operating grip in the Z-axis direction is closer to the end tool than the virtual center axis of the pitch operating joint in the Z-axis direction. That is, the virtual center axis X1 of the pitch operating grip 1112 in the Z-axis direction in the surgical instrument 100 is closer to the end tool than the virtual center axis X2 of the pitch operating joint 1111 in the Z-axis direction. In this case, the pitch operating grip 1112 (or the hand holding that) moving for the pitch operation is located on the front portion than the pitch operating joint 1111 (e.g, the end tool side), and thus, the rotating center of the joint is placed on a portion corresponding to the wrist of the user as shown in FIG. 11A, and the hand of the user is rotated. Thus, the manipulation is intuitively performed and is easy to be performed. That is, as if the end tool 120 actually rotates, the end tool may be manipulated by the user while moving the hand that is in front of the wrist, and thus, the pitch operation of the surgical instrument is intuitively identical to the hand movement.

Referring to FIG. 11B, according to the surgical instrument of the second embodiment, the virtual center axis of the pitch operating grip in the Z-axis direction and the virtual center axis of the pitch operating joint in the Z-axis direction are formed on the same line. That is, the virtual center axis X1 of a pitch operating grip 2112 of a surgical instrument 200 in the X-axis direction is formed at the same distance from the end tool as that of the virtual center axis X2 of a pitch operating joint 2111 in the Z-axis direction. In this case, the pitch operating grip 1112 (or the hand holding that) moving for the pitch operation is located on the pitch joint point, and thus, the rotating center of the joint is placed on a portion where the user holds the pitch operating grip 2112 as shown in FIG. 11B.

Referring to FIG. 11C, according to the surgical instrument of the third embodiment, the virtual center axis of the pitch operating grip in the Z-axis direction is farther from the end tool than the virtual center axis of the pitch operating joint in the Z-axis direction. That is, the virtual center axis X1 of a pitch operating grip 3112 in the Z-axis direction in a surgical instrument 300 is farther from the end tool than the virtual center axis X2 of the pitch operating joint 1111 in the Z-axis direction. In this case, the pitch operating grip 3112 (or the hand holding that) moving for the pitch operation is located behind the pitch operating joint (that is, opposite to the end tool).

A common point among the first, second, and third embodiments of the surgical instrument according to the present invention is that the pitch operating grip 1112 is configured to be closer to the end tool 120 than the virtual center axis X2 of the pitch operating joint in the Z-axis direction in at least one operating stage of the pitch operator 111.

For example, in the surgical instrument according to the first embodiment illustrated with reference to FIG. 11A, since the virtual center axis X1 of the pitch operating grip 1112 in the Z-axis direction is formed to be closer to the end tool 120 than the virtual center axis X2 of the pitch operating joint 1111 in the Z-axis direction, the pitch operating grip 1112 is configured to be closer to the end tool 120 than the virtual center axis X2 of the pitch operating joint 1111 in the Z-axis direction at almost every operating stage of the pitch operator 111.

In addition, in the surgical instrument according to the second embodiment of the present invention illustrated in FIG. 11B, since the virtual center axis X1 of the pitch operating grip 2112 in the Z-axis direction and the virtual center axis X2 of the pitch operating joint 2111 in the Z-axis direction are formed at the same line, if the pitch operator 211 rotates about the pitch operating joint 2111 forward even a little in the state as shown in FIG. 11B, the pitch operating grip 2112 is configured to be closer the end tool 220 than the virtual center axis X2 of the pitch operating joint 2111 in the Z-axis direction.

In addition, in the surgical instrument according to the third embodiment of the present invention illustrated with reference to FIG. 11C, the virtual center axis X1 of the pitch operating grip 3112 in the Z-axis direction is formed to be farther from the end tool than the virtual center axis X2 of the pitch operating joint 3111 in the Z-axis direction. Therefore, in a state as shown in FIG. 11C, the pitch operating grip 3112 is farther from the end tool 320 than the virtual center axis X2 of the pitch operating joint in the Z-axis direction. However, if the pitch operator 311 is rotated forward by a predetermined angle or greater about the pitch operating joint 3111 in order to perform the pitch movement, it is configured that a part of the pitch operating grip 3112 is closer to the end tool 320 than the virtual center axis X2 of the pitch operating joint 3111 in the Z-axis direction.

As described above, in at least one operating stage of the pitch operators 111, 211, and 311, the pitch operating grips 1112, 2112, and 3112 are formed to be closer to the end tools 120, 220, and 320 than the virtual center axis X2 of the pitch operating joint 1111, 2111, and 3111 in the Z-axis direction, and thus, fingers and the hand of the user performing the pitch operation may move more than the wrist joint of the user, wherein the fingers and the hand of the user are located in front of the wrist joint of the user. That is, according to the related art illustrated in FIGS. 1A to 1D, front part of the hand is fixed and rear part of the hand, e.g., the wrist and arm, have to move a lot, which is largely different from the operation of the end tool, and thus, it is difficult to intuitively manipulate the surgical instrument. However, according to the embodiments of the present invention, intuitiveness in manipulating the manipulator for operating the end tool may be greatly improved due to the above-described characteristics.

Second Embodiment of the Surgical Instrument
(E1+H1b)

Hereinafter, the surgical instrument 200 according to the second embodiment of the present invention will be described below. Here, the surgical instrument 200 according to the second embodiment is different from the surgical instrument (see 100 of FIG. 2) according to the first embodiment of the present invention, in that the virtual center axis X1 of the pitch operating grip 2112 of the surgical instrument 200 in the Z-axis direction is formed at the same line as the virtual center axis X2 of the pitch operating joint 2111 in the Z-axis direction. The different structure from that of the first embodiment will be described later in more detail.

Figure 12:
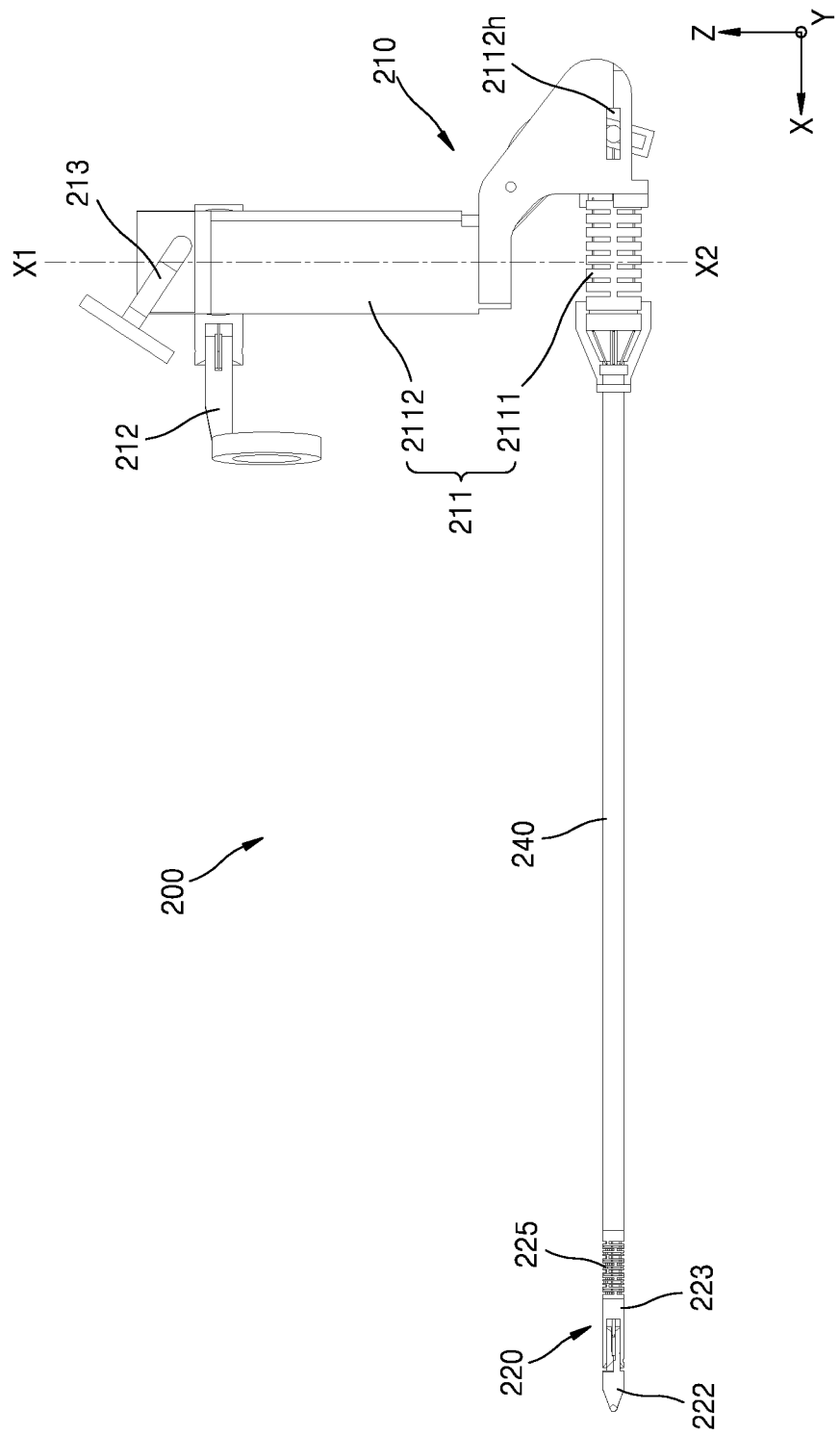
FIGS. 12 and 13 are diagrams of a surgical instrument (200) according to the second embodiment of the present invention.
Figure 13:
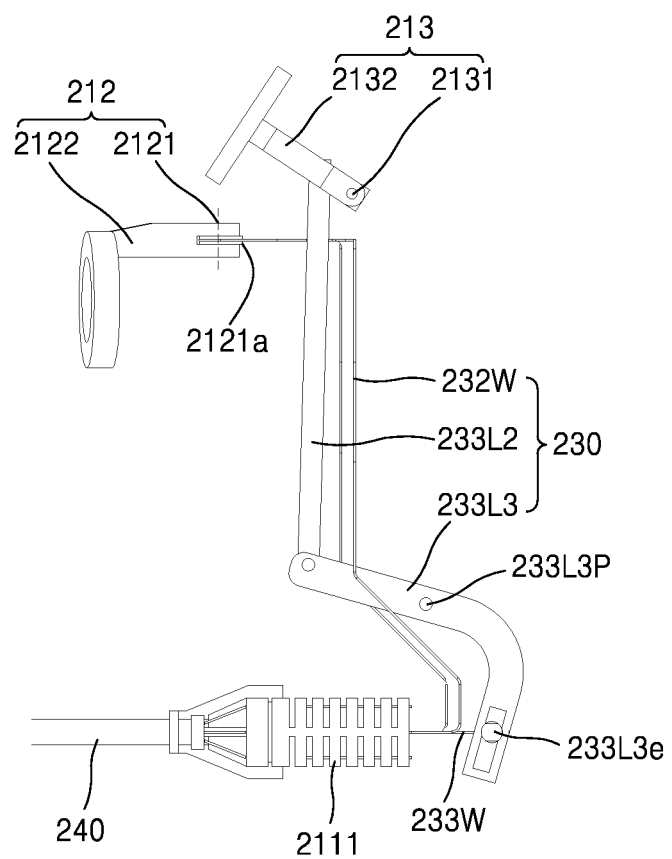

FIGS. 12 and 13 are diagrams of the surgical instrument 200 according to the second embodiment of the present invention. Referring to FIGS. 12 and 13, the surgical instrument 200 according to the second embodiment of the present invention includes a manipulator 210, an end tool 220, a power transfer unit 230, and a connection unit 240.

The manipulator 210 of the surgical instrument 200 includes a pitch operator 211 for controlling the pitch movement of the end tool 220, a yaw operator 212 for performing the yaw movement of the end tool 220, and an actuation operator 213 for controlling the actuation movement of the end tool 220.

The pitch operator 211 includes the pitch operating joint 2111 and the pitch operating grip 2112. Here, the pitch operating joint 2111 may be formed to be rotatable about the Y-axis, and the pitch operating grip 2112 is connected to the pitch operating joint 2111 to be rotatable with the pitch operating joint 2111. Here, the pitch operating joint 2111 may be a curved type joint member.

In addition, the yaw operator 212 and the actuation operator 213 are formed on one end portion of the pitch operating grip 2112 of the pitch operator 211.

The yaw operator 212 includes a yaw rotating axis 2121 and a yaw rotating member 2122. Here, the yaw rotating member 2122 is connected to the yaw rotating axis 2121 to rotate along with the yaw rotating axis 2121. For example, when the user holds and rotates the yaw rotating member 2122 with the index finger, the yaw rotating axis 2121 connected to the yaw rotating member 2122 rotates along with the yaw rotating member 2122, and the rotating force is transmitted to the end tool 220 via the power transfer unit 230 so that two jaws 221 and 222 of the end tool 220 rotate in the same direction as the rotating direction of the yaw rotating axis 2121. To do this, a pulley 2121a may be formed at the yaw rotating axis 2121. In addition, a yaw wire 232W may be connected to the pulley 2121a. The yaw wire 232W is connected to the end tool 220 to rotate the end tool 220.

The actuation operator 213 includes an actuation rotating axis 2131 and an actuation rotating member 2132. In addition, a first actuation link (not shown) may be connected to an end portion of the actuation rotating axis 2131, a second actuation link 233L2 may be connected to an end portion of the first actuation link (not shown), and a third actuation link 233L3 may be connected to an end portion of the second actuation link 233L2. Here, a pivot point 233L3P is formed at the third actuation link 233L3 so as to perform as a central point of the movement of the third actuation link 233L3. In addition, a guide protrusion 233L3e is formed at an end portion of the third actuation link 233L3, and a guide recess 2112h may be formed in the pitch operating grip 2112.

In addition, the end tool 220 of the surgical instrument 200 uses the curved type joint member described above with reference to FIGS. 7A to 7D as a joint member 225. That is, the end tool 220 includes the first jaw (not shown), the second jaw 222, the jaw base 223, and the joint member 225. In addition, the power transfer unit 230 applied to the surgical instrument 200 according to the second embodiment of the present invention includes one or more pitch wires (not shown), one or more yaw wires 232W, and an actuation wire 233W.

Here, according to the surgical instrument of the second embodiment, the virtual center axis of the pitch operating grip in the Z-axis direction and the virtual center axis of the pitch operating joint in the Z-axis direction are formed on the same line. That is, the virtual center axis X1 of a pitch operating grip 2112 of a surgical instrument 200 in the X-axis direction is formed at the same distance from the end tool as that of the virtual center axis X2 of a pitch operating joint 2111 in the Z-axis direction. Here, in the surgical instrument according to the second embodiment of the present invention, the pitch operating grip 2112 is configured to be closer to the end tool 220 than the virtual center axis X2 of the pitch operating joint in the Z-axis direction in at least one operating stage of the pitch operator 211. That is, according to the surgical instrument of the second embodiment, since the virtual center axis X1 of the pitch operating grip 2112 in the Z-axis direction and the virtual center axis X2 of the pitch operating joint 2111 in the Z-axis direction are formed on the same line, if the pitch operator 211 rotates about the pitch operating joint 2111 even a little in the state as shown in FIG. 12, the pitch operating grip 2112 is closer to the end tool 220 than the virtual center axis X2 of the pitch operating joint 2111 in the Z-axis direction.

Third Embodiment of the Surgical Instrument
(E1+H1c)

Hereinafter, the surgical instrument 300 according to the third embodiment of the present invention will be described below. Here, the surgical instrument 300 according to the third embodiment is different from the surgical instrument (see 100 of FIG. 2) according to the first embodiment of the present invention, in that the virtual center axis X1 of the pitch operating grip 3112 of the surgical instrument 300 in the Z-axis direction is formed to be farther from the end tool than the virtual center axis X2 of the pitch operating joint 3111 in the Z-axis direction. Also, a yaw operator 312 is different from that of the surgical instrument (see 100 of FIG. 2) according to the first embodiment of the present invention. The different structure from that of the first embodiment will be described later in more detail.

Figure 14:
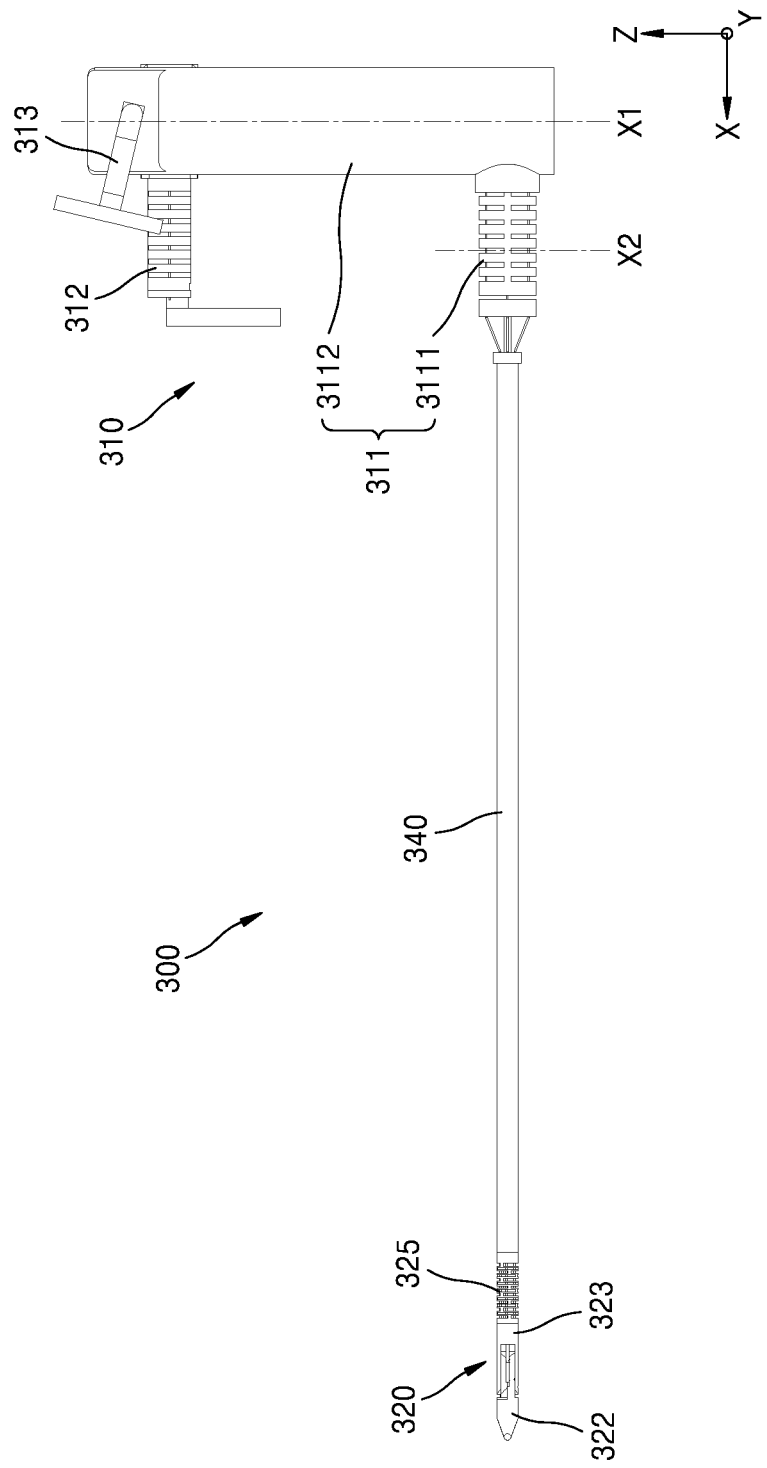
FIGS. 14 and 15 are diagrams of a surgical instrument (300) according to the third embodiment of the present invention.
Figure 15:
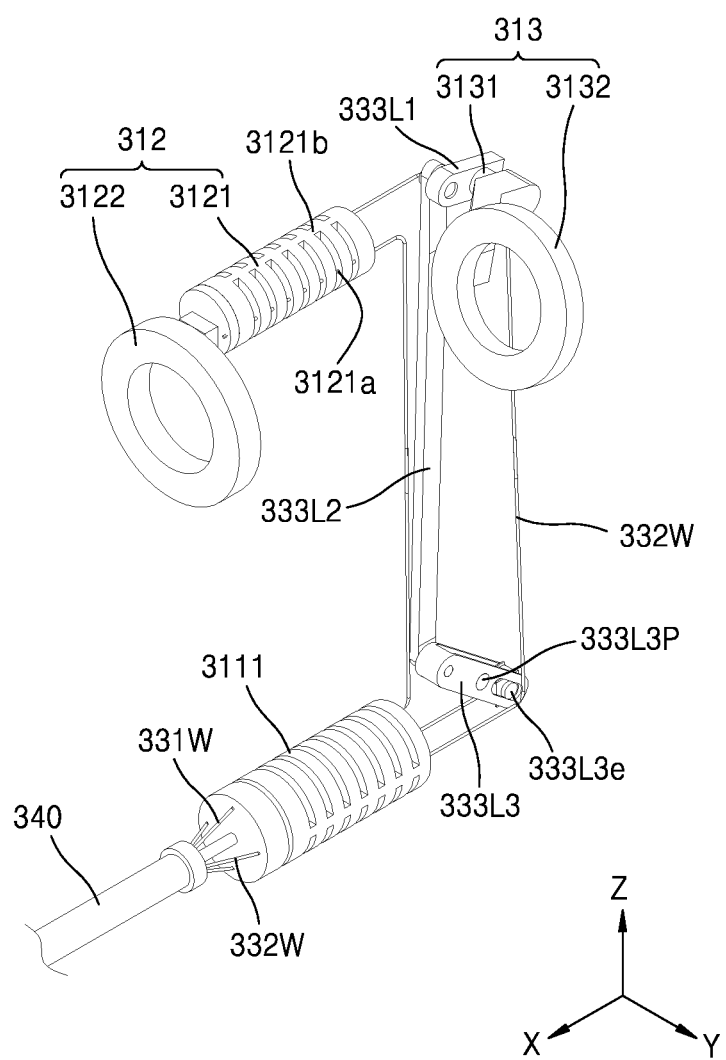

FIGS. 14 and 15 are diagrams of a surgical instrument 300 according to the third embodiment of the present invention. Referring to FIGS. 14 and 15, the surgical instrument 300 according to the third embodiment of the present invention includes a manipulator 310, an end tool 320, a power transfer unit 330, and a connection unit 340.

The manipulator 310 of the surgical instrument 300 includes a pitch operator 311 for controlling the pitch movement of the end tool 320, a yaw operator 312 for performing the yaw movement of the end tool 320, and an actuation operator 313 for controlling the actuation movement of the end tool 320.

The pitch operator 311 includes the pitch operating joint 3111 and the pitch operating grip 3112. Here, the pitch operating joint 3111 may be formed to be rotatable about the Y-axis, and the pitch operating grip 3112 is connected to the pitch operating joint 3111 to be rotatable with the pitch operating joint 3111. Here, the pitch operating joint 3111 may be a curved type joint member.

In addition, the yaw operator 312 includes a yaw rotating joint 3121 and a yaw rotating member 3122. Here, the yaw rotating member 3122 is connected to the yaw rotating joint 3121 to be rotated with the yaw rotating joint 3121. For example, when the user holds and rotates the yaw rotating member 3122 with the index finger, the yaw rotating joint 3121 connected to the yaw rotating member 3122 rotates along with the yaw rotating member 3122, and the rotating force is transmitted to the end tool 320 via the power transfer unit 330 so that two jaws of the end tool 320 rotate in the same direction as the rotating direction of the yaw rotating joint 3121.

That is, in the third embodiment, the curved type joint member is used as the yaw operator 312, which is an equivalent element having the same objective as that of the yaw operator in the above-described embodiments in that the rotation is made according to the yaw operation, and various other structures than the curved type joint member of the present embodiment may be used to achieve the objective. In the present embodiment, the yaw operator 312 is formed as a hollow cylinder shape, and a plurality of recesses 3121a are formed in an outer circumferential surface thereof along a direction (X-axis direction) so that the yaw operator 312 may be curved. Here, a rib 3121b is formed at a center portion of each of the recesses 3121a for determining a curved direction of the yaw rotating joint 3121. That is, at a portion where the rib 3121b is formed, the curvature is not performed, and the curvature of the yaw rotating joint is performed at the portion where the rib 3121b is not formed. That is, the ribs 3121b are formed along upper and lower surfaces of the yaw rotating joint 3121, and thus, the yaw rotating joint 3121 may be curved in a left-and-right direction where the ribs 3121b are not provided. Therefore, although an actual rotating axis does not exist in the yaw rotating joint 3121, it may be assumed that the yaw rotating joint 3121 rotates in the left-and-right direction about the Z-axis. Therefore, the yaw rotating joint 3121 is formed as a curved type joint member, and becomes a rotating center of the yaw movement.

The actuation operator 313 includes an actuation rotating axis 3131 and an actuation rotating member 3132. In addition, a first actuation link 333L1 may be connected to an end portion of the actuation rotating axis 3131, a second actuation link 333L2 may be connected to an end portion of the first actuation link 333L1, and a third actuation link 333L3 may be connected to an end portion of the second actuation link 333L2. Here, a pivot point 333L3P is formed at the third actuation link 333L3 so as to perform as a central point of the movement of the third actuation link 333L3. In addition, a guide protrusion 333L3e is formed at an end portion of the third actuation link 333L3, and a guide recess (not shown) may be formed in the pitch operating grip 3112.

In addition, the end tool 320 of the surgical instrument 300 uses the curved type joint member described above with reference to FIGS. 7A to 7D as a joint member 325. That is, the end tool 320 includes a first jaw (not shown), a second jaw 322, a jaw base 323, and the joint member 325. In addition, the power transfer unit 330 applied to the surgical instrument 300 according to the third embodiment of the present invention includes one or more pitch wires 331W, one or more yaw wires 332W, and an actuation wire (not shown).

Here, according to the surgical instrument of the third embodiment, the virtual center axis of the pitch operating grip in the Z-axis direction is farther from the end tool than the virtual center axis of the pitch operating joint in the Z-axis direction. That is, the virtual center axis X1 of a pitch operating grip 3112 in the Z-axis direction in a surgical instrument 300 is farther from the end tool than the virtual center axis X2 of the pitch operating joint 1111 in the Z-axis direction.

Here, in the surgical instrument according to the third embodiment of the present invention, the pitch operating grip 3112 is configured to be closer to the end tool 320 than the virtual center axis X2 of the pitch operating joint in the Z-axis direction in at least one operating stage of the pitch operator 311. Therefore, according to the surgical instrument of the third embodiment, the pitch operating grip 3112 is farther from the end tool 320 than the virtual center axis X2 of the pitch operating joint in the Z-axis direction. However, if the pitch operator 311 is rotated by a predetermined angle or greater about the pitch operating joint 3111 in order to perform the pitch movement, it is configured that a part of the pitch operating grip 3112 is closer to the end tool 320 than the virtual center axis X2 of the pitch operating joint 3111 in the Z-axis direction.

Fourth Embodiment of the Surgical Instrument
(E1+H21)

Hereinafter, a surgical instrument 400 according to a fourth embodiment of the present invention will be described below. Here, the surgical instrument 400 according to the fourth embodiment of the present invention is different from the surgical instrument (see 100 of FIG. 2)

described above according to the first embodiment, in that pitch/yaw operator 411 in which a pitch operator and a yaw operator of a manipulator 410 are integrally formed is provided to perform functions of both the pitch operator and the yaw operator, and the pitch/yaw operator 411 is formed over an extension line of an end tool 420. Accordingly, in the surgical instrument 400 according to the fourth embodiment of the present invention, the pitch/yaw operator 411 is manipulated by using the finger of the user, not the wrist of the user. The different structure from that of the first embodiment will be described later in more detail.

Figure 16:
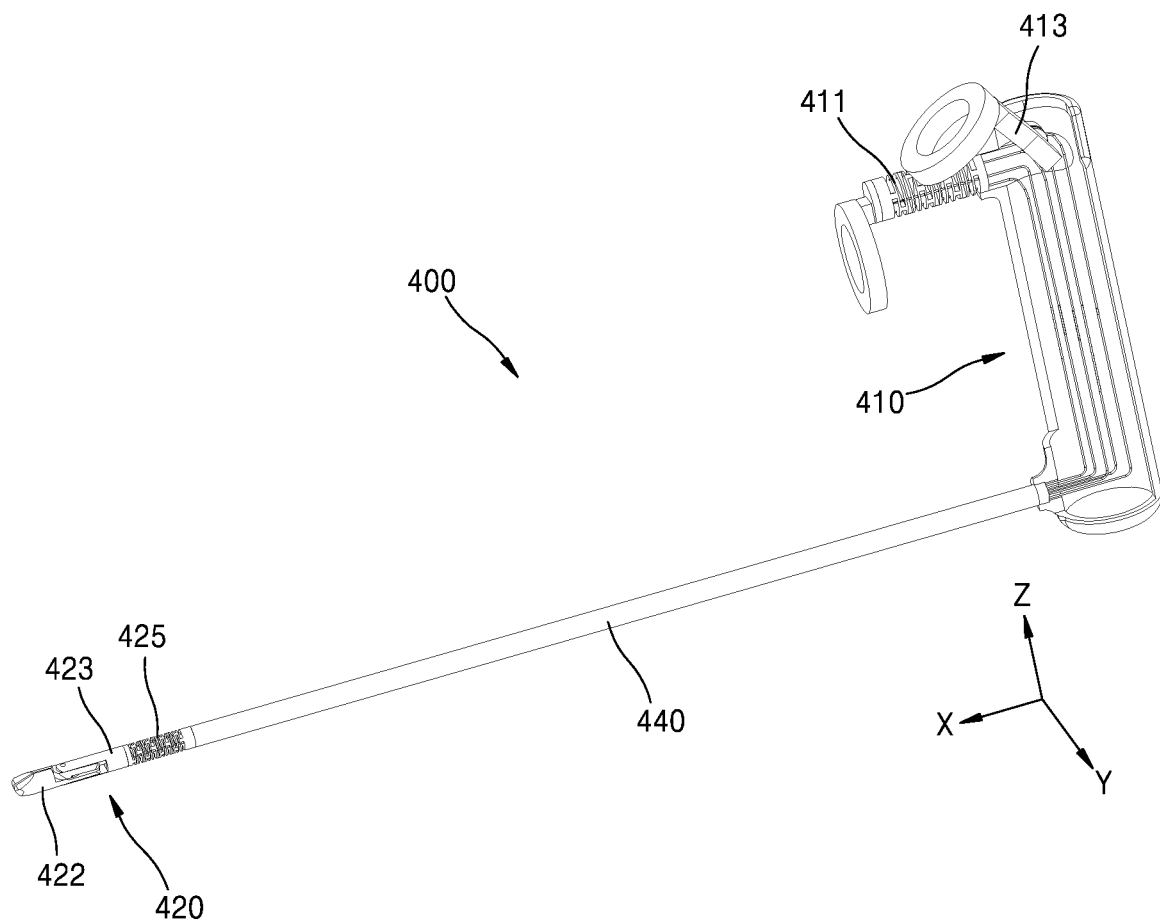
FIGS. 16 and 17 are diagrams of a surgical instrument (400) according to the fourth embodiment of the present invention.
Figure 17:
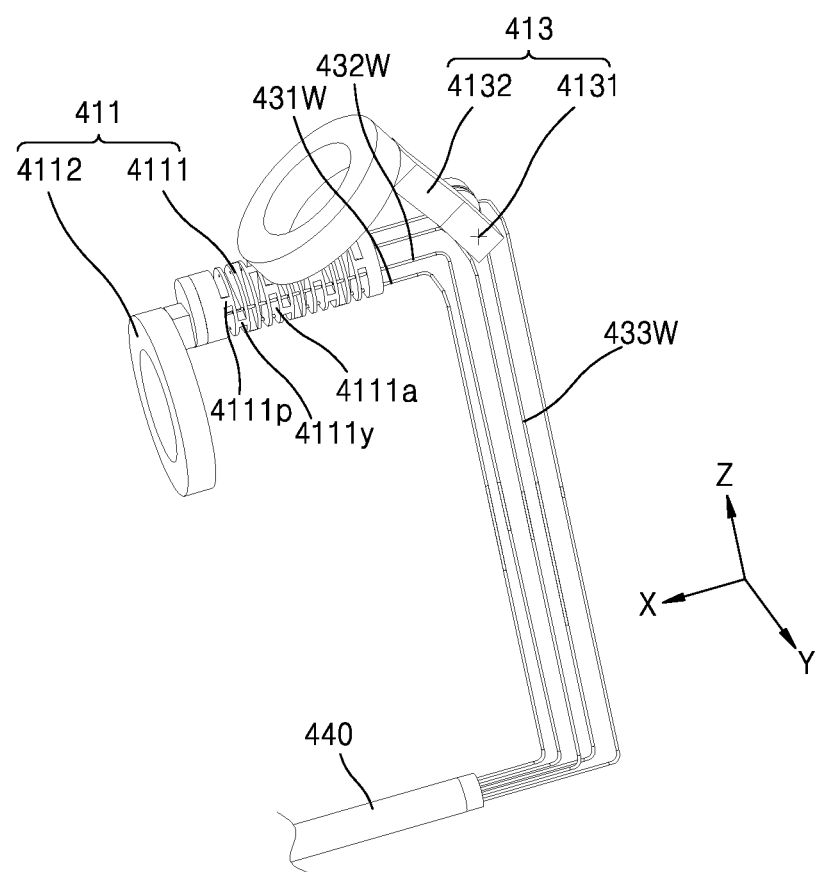

FIGS. 16 and 17 are diagrams of the surgical instrument 400 according to the fourth embodiment of the present invention. Referring to FIGS. 16 and 17, the surgical instrument 400 according to the fourth embodiment of the present invention includes a manipulator 410, an end tool 420, a power transfer unit 430, and a connection unit 440.

The manipulator 410 of the surgical instrument 400 includes the pitch/yaw operator 411 for controlling the pitch movement and the yaw movement of the end tool 420, and an actuation operator 413 for controlling the actuation movement of the end tool 420.

The pitch/yaw operator 411 includes a pitch/yaw rotating joint 411 and a pitch/yaw rotating member 4112. Here, the pitch/yaw rotating joint 4111 may be configured to rotate about the Y-axis and the Z-axis, and the pitch/yaw rotating member 4112 is connected to the pitch/yaw rotating joint 4111 to rotate with the pitch/yaw rotating joint 4111. Here, the pitch/yaw rotating joint 4111 may be a curved type joint member.

The pitch/yaw rotating joint 4111 formed as the curved type has a hollow cylinder shape, and a plurality of recesses 4111a are formed in an outer circumferential surface in a direction (X-axis direction) so that the pitch/yaw rotating joint 4111 may be curved. Here, first ribs 4111P and second ribs 4111Y are formed at a center portion of each of the recesses 4111a for guiding a curved direction of the pitch/yaw rotating joint 4111. That is, the pitch/yaw rotating joint 4111 is not curved at the portions where the ribs 4111P and 4111Y are formed, but is mainly curved at portions where the ribs 4111P and 4111Y are not formed.

Here, first ribs 4111P for guiding the curvature (e.g., the pitch movement) of the pitch/yaw rotating joint 4111 in a first direction and second ribs 4111Y for guiding the curvature (e.g., the yaw movement) of the pitch/yaw rotating joint 4111 in a second direction are formed in the pitch/yaw rotating joint 4111. Here, the second ribs 4111Y may be offset a predetermined degree with respect to the first ribs 4111P. In addition, the first ribs 4111P and the second ribs 4111Y may be alternatively formed in a manner that the first ribs 4111P are formed in even-numbered recesses 4111a and the second ribs 4111Y are formed in odd-numbered recesses 4111a.

That is, in FIG. 17, the first ribs 4111P are formed along opposite side surfaces of the pitch/yaw rotating joint 4111, and thus, the pitch/yaw rotating joint 4111 may be curved in an up-and-down direction. Therefore, although an actual rotating axis does not exist in the pitch/yaw rotating joint 4111, it may be assumed that the pitch/yaw rotating joint 4111 rotates in the up-and-down direction about the Y-axis of FIG. 17. Therefore, the pitch/yaw rotating joint 4111 may be a rotating center of the pitch movement.

In addition, since the second ribs 4111Y are formed along upper and lower surfaces of the pitch/yaw rotating joint 4111, the pitch/yaw rotating joint 4111 may be curved in a left-and-right direction. Therefore, although an actual rotating axis does not exist in the pitch/yaw rotating joint 4111, it may be assumed that the pitch/yaw rotating joint 4111 rotates in the left-and-right direction about the Z-axis of FIG. 17. Therefore, the pitch/yaw rotating joint 4111 may be a rotating center of the yaw movement.

Here, the first ribs 4111P and the second ribs 4111Y do not have to be formed on a vertical plane or a horizontal plane of the pitch/yaw rotating joint 4111, but may be offset a predetermined degree from the vertical plane or the horizontal plane of the pitch/yaw rotating joint 4111.

In addition, opposite end portions of pitch wires 431W and yaw wires 432W are respectively coupled to an end portion of the pitch/yaw rotating joint 4111 at the pitch/yaw rotating member 4112 side. Therefore, when the pitch/yaw rotating member 4112 is rotated, the pitch/yaw rotating joint 4111 connected to the pitch/yaw rotating member 4112 is rotated, and as the pitch/yaw rotating joint 4111 is rotated, one end portions of the pitch wires 431W or the yaw wires 432W are pushed and the other end portions are pulled so as to perform the pitch movement or the yaw movement of the end tool 420.

In other words, the rotating center (e.g., the joint member) of the pitch movement and the yaw movement is also formed behind the end tool (the first and second jaws) and the rotating center (e.g., pitch/yaw rotating joint) of the pitch movement and the yaw movement is also formed behind the manipulator (pitch/yaw rotating member), and thus, the end tool and the manipulator are both moved based on the rotating centers formed behind them and the operations thereof may be intuitively identical with each other.

The actuation operator 413 includes an actuation rotating axis 4131 and an actuation rotating member 4132. In addition, the actuation wire 433W may be connected to an end portion of the actuation rotating axis 4131. In addition, the other end portion of the actuation wire 433W may be connected to the actuation guide pin (see 133WG of FIG. 8) of the end tool 420.

In addition, the end tool 420 of the surgical instrument 400 uses the curved type joint member described above with reference to FIGS. 7A to 7D as a joint member 425. That is, the end tool 420 includes a first jaw (not shown), a second jaw 422, a jaw base 423, and the joint member 425. In addition, the power transfer unit 430 applied in the surgical instrument 400 according to the fourth embodiment includes one or more pitch wires 431W, one or more yaw wires 432W, and an actuation wire 433W.

Here, the surgical instrument according to the fourth embodiment of the present invention 1) includes the pitch/yaw operator 411 in which the pitch operator and the yaw operator of the manipulator 410 are integrally formed so as to perform functions of both the pitch operator and the yaw operator, as described above. 2) Here, the pitch/yaw operator 411 is formed above an extension line of an end tool 420.

Classification of Fifth, Sixth, and Seventh Embodiments of the Surgical Instrument Hereinafter, before describing the surgical instrument according to the fifth, sixth, and seventh embodiments, criteria for classifying the fifth, sixth, and seventh embodiments of the surgical instrument according to the present invention will be described below.

Figure 18B:
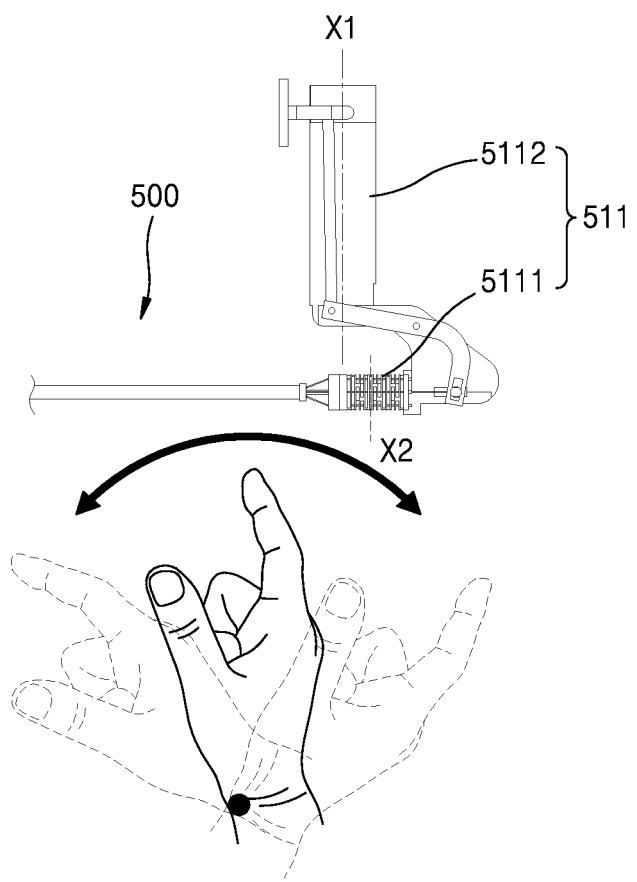
FIG. 18B is a conceptual diagram of a yaw operation.
Figure 18D:
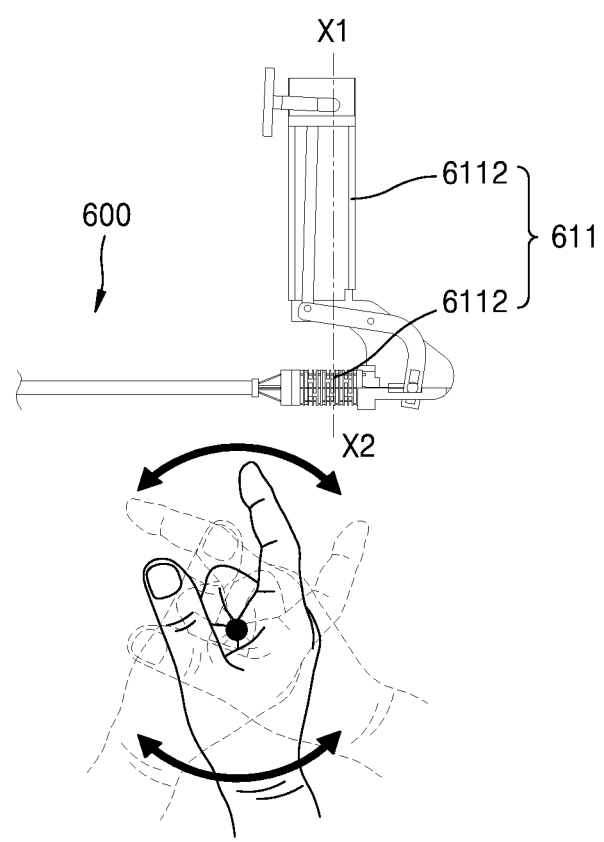
FIG. 18D is a conceptual diagram of a yaw operation.
Figure 18F:
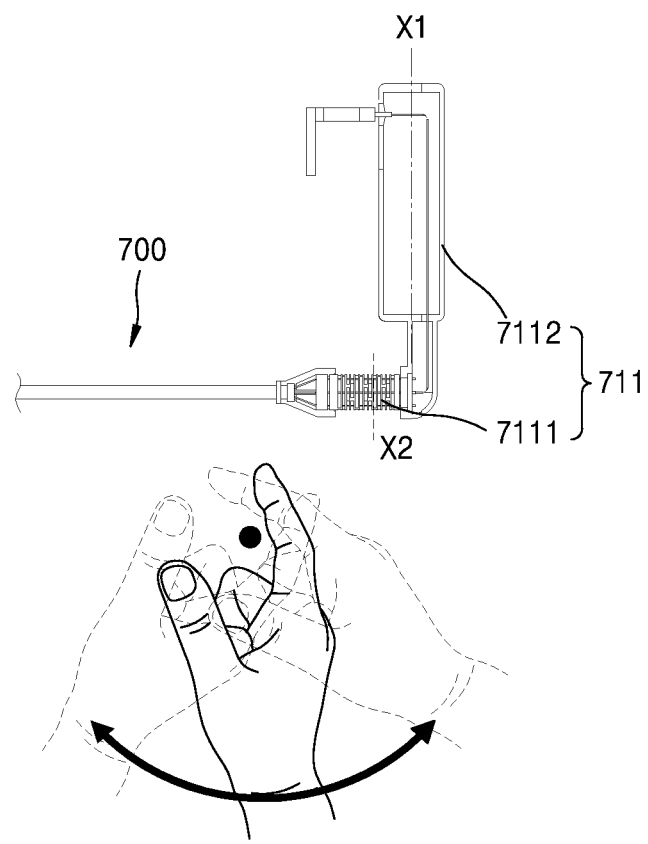
FIG. 18F is a conceptual diagram of a yaw operation.

FIG. 18A is a conceptual diagram of a pitch operation of a surgical instrument according to the fifth embodiment, FIG. 18B is a conceptual diagram of a yaw operation, FIG. 18C is a conceptual diagram of a pitch operation of a surgical instrument according to the sixth embodiment, FIG. 18D is a conceptual diagram of a yaw operation, FIG. 18E is a conceptual diagram of a pitch operation of a surgical instrument according to the seventh embodiment, FIG. 18F is a conceptual diagram of a yaw operation.

Here, the fifth, sixth, and seventh embodiments of the surgical instrument of the present invention are classified in view of locational relationship between of a virtual center line of the pitch/yaw operating grip in the Z-axis direction and a virtual center line of the pitch/yaw rotating joint in the Z-axis direction.

Referring to FIGS. 18A and 18B, the surgical instrument according to the fifth embodiment of the present invention is characterized in that the virtual center axis of the pitch/yaw operating grip in the Z-axis direction is closer to the end tool than a virtual center axis of the pitch/yaw rotating joint in the Z-axis direction. That is, a virtual center axis X1 of a pitch/yaw operating grip 5112 in the Z-axis direction in the surgical instrument 500 is closer to the end tool than a virtual center axis X2 of a pitch/yaw rotating joint 5111 in the Z-axis direction.

In this case, the pitch/yaw operating grip 5112 (or the hand holding that) moving for the pitch movement is located on a front portion than a pitch/yaw joint point (e.g., the end tool side), and thus, the rotating center of the joint is placed on a portion corresponding to the wrist of the user as shown in FIG. 18A, and the hand of the user is rotated. Thus, the manipulation is intuitively performed and is easy to be performed. That is, as if the end tool 520 actually rotates, the end tool may be manipulated by the user while moving the hand that is in front of the wrist, and thus, the pitch movement of the surgical instrument is intuitively identical to the hand movement.

In addition, the pitch/yaw operating grip 5112 (or the hand holding that) moving for the yaw movement is located on a front portion than a pitch/yaw joint point (e.g., the end tool side), and thus, the rotating center of the joint is placed on a portion corresponding to the wrist of the user as shown in FIG. 18B, and the hand of the user is rotated. Thus, the manipulation is intuitively performed and is easy to be performed. That is, as if the end tool 520 actually rotates, the end tool may be manipulated by the user while moving the hand that is in front of the wrist, and thus, the yaw movement of the surgical instrument is intuitively identical to the hand movement. The above configuration is applied to an eighth embodiment that will be described later.

Referring to FIGS. 18C and 18D, the surgical instrument according to the sixth embodiment of the present invention is characterized in that the virtual center axis of the pitch/yaw operating grip in the Z-axis direction and a virtual center axis of the pitch/yaw rotating joint in the Z-axis direction are formed on the same line. That is, a virtual center axis X1 of a pitch/yaw operating grip 6112 in the Z-axis direction in a surgical instrument 600 and a virtual center axis X2 of a pitch/yaw rotating joint 5111 in the Z-axis direction are formed at the same distance from the end tool.

In this case, the pitch/yaw operating grip 6112 (or the hand holding that) moving for the pitch movement is located on the pitch/yaw joint point, and thus, the rotating center of the joint is placed on a portion where the user grips the pitch/yaw operating grip 6112 as shown in FIG. 18B.

In addition, the pitch/yaw operating grip 6112 (or the hand holding that) moving for the yaw movement is located on the pitch/yaw joint point, and thus, the rotating center of the joint is placed on a portion where the user grips the pitch/yaw operating grip 6112 as shown in FIG. 18D. Therefore, in this case, front and rear parts of the hand are both moved. The above configuration is applied to a ninth embodiment that will be described later.

Referring to FIGS. 18E and 18F, the surgical instrument according to the seventh embodiment of the present invention is characterized in that the virtual center axis of the pitch/yaw operating grip in the Z-axis direction is farther from the end tool than a virtual center axis of the pitch/yaw rotating joint in the Z-axis direction. That is, a virtual center axis X1 of a pitch/yaw operating grip 7112 in the Z-axis direction in a surgical instrument 700 is farther from the end tool than a virtual center axis X2 of a pitch/yaw rotating joint 7111 in the Z-axis direction.

In this case, the pitch/yaw operating grip 7112 (or the hand holding that) moving for the pitch movement is located behind a pitch/yaw joint point (that is, opposite to the end tool).

In addition, the pitch/yaw operating grip 7112 (or the hand holding that) moving for the yaw movement is located behind a pitch/yaw joint point (e.g., opposite the end tool side), and thus, the front part of the user is fixed and the rear part of the hand (e.g., the wrist, etc.) is moved as shown in FIG. 18E.

A common point among the fifth, sixth, and seventh embodiments of the surgical instrument according to the present invention is that the pitch/yaw operating grip is configured to be closer to the end tool than the virtual center axis X2 of the pitch/yaw rotating joint in the Z-axis direction in at least one operating stage of at least the pitch operator.

For example, according to the surgical instrument of the fifth embodiment illustrated in FIGS. 18A and 18B, the virtual center axis X1 of the pitch/yaw operating grip 5112 in the Z-axis direction is closer to the end tool 520 than the virtual center axis X2 of the pitch/yaw rotating joint 5111, and thus, the pitch/yaw operating grip 5112 is formed to be closer to the end tool 520 than the virtual center axis X2 of the pitch/yaw rotating joint 5111 in the Z-axis direction in almost every operating stage of the pitch/yaw operator 511.

In addition, in the surgical instrument according to the sixth embodiment illustrated in FIGS. 18C and 18D, since the virtual center axis X1 of the pitch/yaw operating grip 6112 in the Z-axis direction and the virtual center axis X2 of the pitch/yaw rotating joint 6111 in the Z-axis direction are formed at the same line, if the pitch/yaw operator 611 is rotated forward even a little based on the pitch/yaw rotating joint 6111 in the state of FIG. 18C, the pitch/yaw operating grip 6112 is closer to the end tool 620 than the virtual center axis X2 of the pitch/yaw rotating joint 6111 in the Z-axis direction.

In addition, in the surgical instrument according to the seventh embodiment illustrated in FIGS. 18E and 18F, a virtual center axis X1 of a pitch/yaw operating grip 7112 in the Z-axis direction is farther from the end tool than a virtual center axis X2 of a pitch/yaw rotating joint 7111 in the Z-axis direction. Therefore, in a state as shown in FIG. 18E, the pitch/yaw operating grip 7112 is farther from an end tool 720 than the virtual center axis X2 of the pitch/yaw rotating joint in the Z-axis direction. However, if the pitch/yaw operator 711 is rotated forward by a predetermined angle or greater about the pitch/yaw rotating joint 7111 in order to perform the pitch operation, it is configured that a part of the pitch/yaw operating grip 7112 is closer to the end tool 720 than the virtual center axis X2 of the pitch/yaw rotating joint 7111 in the Z-axis direction.

As described above, in at least one operating stage of the pitch/yaw operators 511, 611, and 711, the pitch/yaw operating grips 5112, 6112, and 7112 are formed to be closer to the end tools 520, 620, and 720 than the virtual center axis X2 of the pitch/yaw rotating joints 5111, 6111, and 7111 in the Z-axis direction, and thus, fingers and the hand of the user performing the pitch operation may move more than the wrist joint of the user, wherein the fingers and the hand of the user are located in front of the wrist joint of the user. That is, according to the related art illustrated in FIGS. 1A to 1D, the front part of the hand is fixed and the rear part of the hand, e.g., the wrist and arm, have to move a lot, which is largely different from the operation of the end tool, and thus, it is difficult to intuitively manipulate the surgical instrument. However, according to the embodiments of the present invention, intuitiveness in manipulating the manipulator for operating the end tool may be greatly improved due to the above-described characteristics.

Fifth Embodiment of the Surgical Instrument (E1+H22a)

Hereinafter, the surgical instrument 500 according to the fifth embodiment of the present invention will be described below. Here, the surgical instrument 500 according to the fifth embodiment of the present invention is different from the surgical instrument (see 100 of FIG. 2) described above according to the first embodiment, in that the pitch/yaw operator 511 in which a pitch operator and a yaw operator of a manipulator 510 are integrally formed is provided to perform functions of both the pitch operator and the yaw operator, and the pitch/yaw operator 511 is formed on an extension line of an end tool 520. In addition, the surgical instrument 500 according to the fifth embodiment of the present invention is characterized in that the virtual center axis X1 of the pitch/yaw operating grip 5112 of the surgical instrument 500 in the Z-axis direction is closer to the end tool 520 than the virtual center axis X2 of the pitch/yaw rotating joint 5111 in the Z-axis direction. The different structure from that of the first embodiment will be described later in more detail.

Figure 19A:
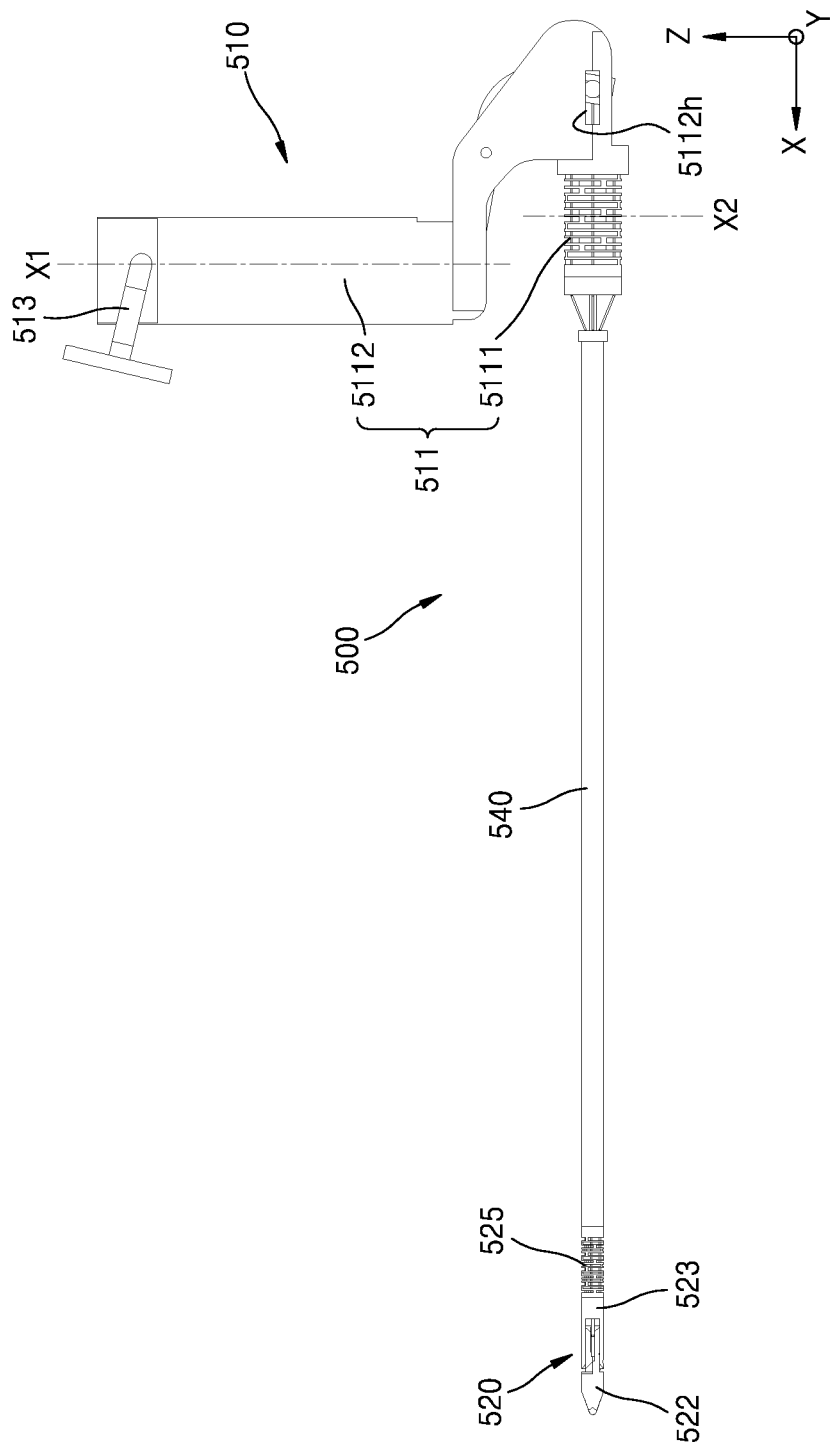
FIGS. 19A and 19B are diagrams of a surgical instrument (800) according to the fifth embodiment of the present invention.
Figure 19B:
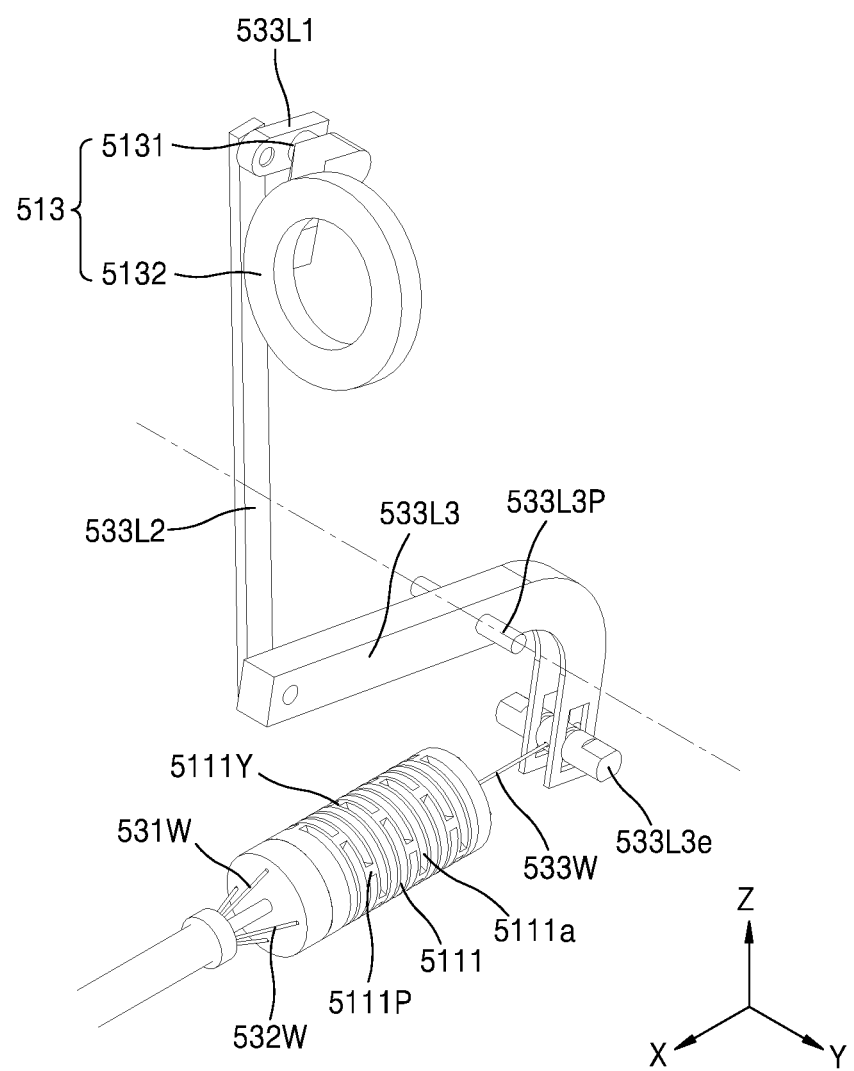

FIGS. 19A and 19B are diagrams of the surgical instrument 500 according to the fifth embodiment of the present invention. Referring to FIGS. 19A and 19B, the surgical instrument 500 according to the fifth embodiment of the present invention includes a manipulator 510, an end tool 520, a power transfer unit 530, and a connection unit 540.

The manipulator 510 of the surgical instrument 500 includes the pitch/yaw operator 511 for controlling the pitch movement and the yaw movement of the end tool 520, and an actuation operator 513 for controlling the actuation movement of the end tool 520.

The pitch/yaw operator 511 includes a pitch/yaw rotating joint 5111 and a pitch/yaw operating grip 5112. Here, the pitch/yaw rotating joint 5111 may be configured to rotate about the Y-axis and the Z-axis, and the pitch/yaw operating grip 5112 is connected to the pitch/yaw rotating joint 5111 to rotate with the pitch/yaw rotating joint 5111. Here, the pitch/yaw rotating joint 5111 may be a curved type joint member.

The pitch/yaw rotating joint 5111 formed as the curved type has a hollow cylinder shape, and a plurality of recesses 5111a are formed in an outer circumferential surface in a direction (X-axis direction) so that the pitch/yaw rotating joint 5111 may be curved. Here, first and second ribs 5111P and 5111Y are formed at a center portion of each of the recesses 5111a for guiding a curved direction of the pitch/yaw rotating joint 5111. That is, the pitch/yaw rotating joint 5111 is not curved at the portions where the ribs 5111P and 5111Y are formed, but is mainly curved at portions where the ribs 5111P and 5111Y are not formed.

Here, the pitch/yaw rotating joint 5111 is rotated by the first ribs 5111P in an up-and-down direction about the Y-axis, the first ribs 5111P guiding the curvature of the pitch/yaw rotating joint 5111 in the first direction (e.g., the pitch movement), and the pitch/yaw rotating joint 5111 may become a rotating center of the pitch movement. Also, the pitch/yaw rotating joint 5111 is rotated by the second ribs 5111Y in a left-and-right direction about the Z-axis, the second ribs 5111Y guiding the curvature of the pitch/yaw rotating joint 5111 in the second direction (e.g., the yaw movement), and the pitch/yaw rotating joint 5111 may become a rotating center of the yaw movement.

In other words, as shown in FIG. 19B, the first ribs 5111P may be formed on a diameter of the pitch/yaw rotating joint 5111 in the Y-axis direction in order to be the rotating center of the pitch movement, and the second ribs 5111Y may be formed on a diameter of the pitch/yaw rotating joint 5111 in the Z-axis direction in order to be the rotating center of the yaw movement. Moreover, ribs may be additionally formed at various locations in the pitch/yaw rotating joint 5111, besides the first and second ribs 5111P and 5111Y, and the ribs may smoothen the curvature of the pitch/yaw rotating joint 5111.

In addition, opposite end portions of pitch wires 531W and yaw wires 532W are respectively coupled to an end portion of the pitch/yaw rotating joint 511 at the end tool 520 side. Therefore, when the pitch/yaw operating grip 5112 is rotated, the pitch/yaw rotating joint 5111 connected to the pitch/yaw operating grip 5112 is rotated, and as the pitch/yaw rotating joint 5111 is rotated, one end portions of the pitch wires 531W or the yaw wires 532W are pushed and the other end portions are pulled so as to perform the pitch movement or the yaw movement of the end tool 520.

The actuation operator 513 includes an actuation rotating axis 5131 and an actuation rotating member 5132. In addition, a first actuation link 533L1 may be connected to an end portion of the actuation rotating axis 5131, a second actuation link 533L2 may be connected to an end portion of the first actuation link 533L1, and a third actuation link 533L3 may be connected to an end portion of the second actuation link 533L2. Here, a pivot point 533L3P is formed at the third actuation link 533L3 so as to perform as a central point of the movement of the third actuation link 533L3. In addition, a guide protrusion 533L3e is formed at an end portion of the third actuation link 533L3, and a guide recess 5112h may be formed in the pitch/yaw operating grip 5112. In addition, an actuation wire 533W may be connected to the guide protrusion 533L3e. In addition, the other end portion of the actuation wire 533W may be connected to the actuation guide pin (see 133WG of FIG. 8) of the end tool 520.

In addition, the end tool 520 of the surgical instrument 500 uses the curved type joint member described above with reference to FIGS. 7A to 7D as a joint member 525. That is, the end tool 520 includes a first jaw (not shown), a second jaw 522, a jaw base 523, and the joint member 525. In addition, the power transfer unit 530 applied in the surgical instrument 500 according to the fifth embodiment includes one or more pitch wires 531W, one or more yaw wires 532W, and the actuation wire 533W.

Here, the surgical instrument according to the fifth embodiment of the present invention 1) includes the pitch/yaw operator 511 in which the pitch operator and the yaw operator of the manipulator 510 are integrally formed so as to perform functions of both the pitch operator and the yaw operator, as described above. 2) Here, the pitch/yaw operator 511 is formed on an extension line of an end tool 520.

In addition, in the surgical instrument according to the fifth embodiment of the present invention, the virtual center axis X1 of the pitch/yaw operating grip 5112 in the Z-axis direction is closer to the end tool 520 than the virtual center axis X2 of the pitch/yaw rotating joint 5111 in the Z-axis direction.

Therefore, in the surgical instrument according to the fifth embodiment, the pitch/yaw operating grip 5112 is configured to be closer to the end tool 520 than the virtual center axis X2 of the pitch/yaw rotating joint 5111 in the Z-axis direction. That is, in the surgical instrument according to the fifth embodiment, since the virtual center axis X1 of the pitch/yaw operating grip 5112 in the Z-axis direction itself is closer to the end tool 520 than the virtual center axis X2 of the pitch/yaw rotating joint 5111 in the Z-axis direction, the pitch/yaw operating grip 5112 is closer to the end tool 520 than the virtual center axis X2 of the pitch/yaw rotating joint 5111 in the Z-axis direction in almost every operating stage of the pitch/yaw operator 511.

As described above, since the pitch/yaw operating grip 5112 is closer to the end tool 520 than the virtual center axis X2 of the pitch/yaw rotating joint 5111 in the Z-axis direction in at least one operating stage of the pitch/yaw operator 511, fingers and the hand of the user in front of the wrist joint of the user who is performing the pitch operation may move more than the wrist joint. That is, according to the related art illustrated in FIGS. 1A to 1D, the front part of the hand is fixed and the rear part of the hand, e.g., the wrist and arm, have to move a lot, which is largely different from the operation of the end tool, and thus, it is difficult to intuitively manipulate the surgical instrument. However, according to the present embodiment, intuitiveness in manipulating the manipulator for operating the end tool may be greatly improved due to the above-described characteristics.

Sixth Embodiment of a Surgical Instrument
(E1+H22b)

Hereinafter, a surgical instrument 600 according to the sixth embodiment of the present invention will be described below. Here, the surgical instrument 600 according to the sixth embodiment is different from the surgical instrument (see 500 of FIG. 19A) according to the fifth embodiment of the present invention, in that a virtual center axis X1 of a pitch/yaw operating grip 6112 of the surgical instrument 600 in the Z-axis direction is formed at the same line as a virtual center axis X2 of a pitch/yaw rotating joint 6111 in the Z-axis direction.

Figure 20:
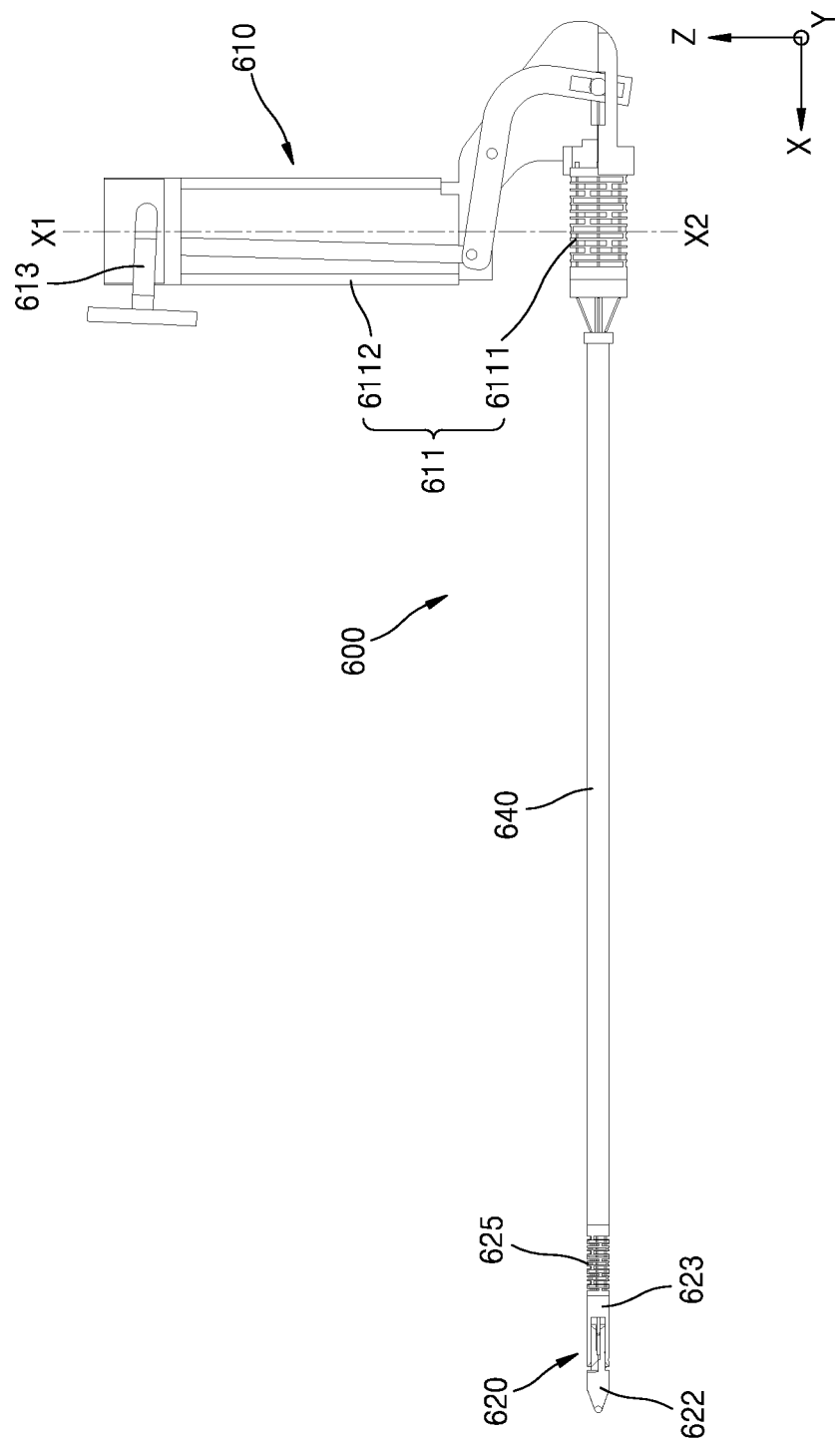
FIGS. 20 and 21 are diagrams of a surgical instrument (600) according to the sixth embodiment of the present invention.
Figure 21:
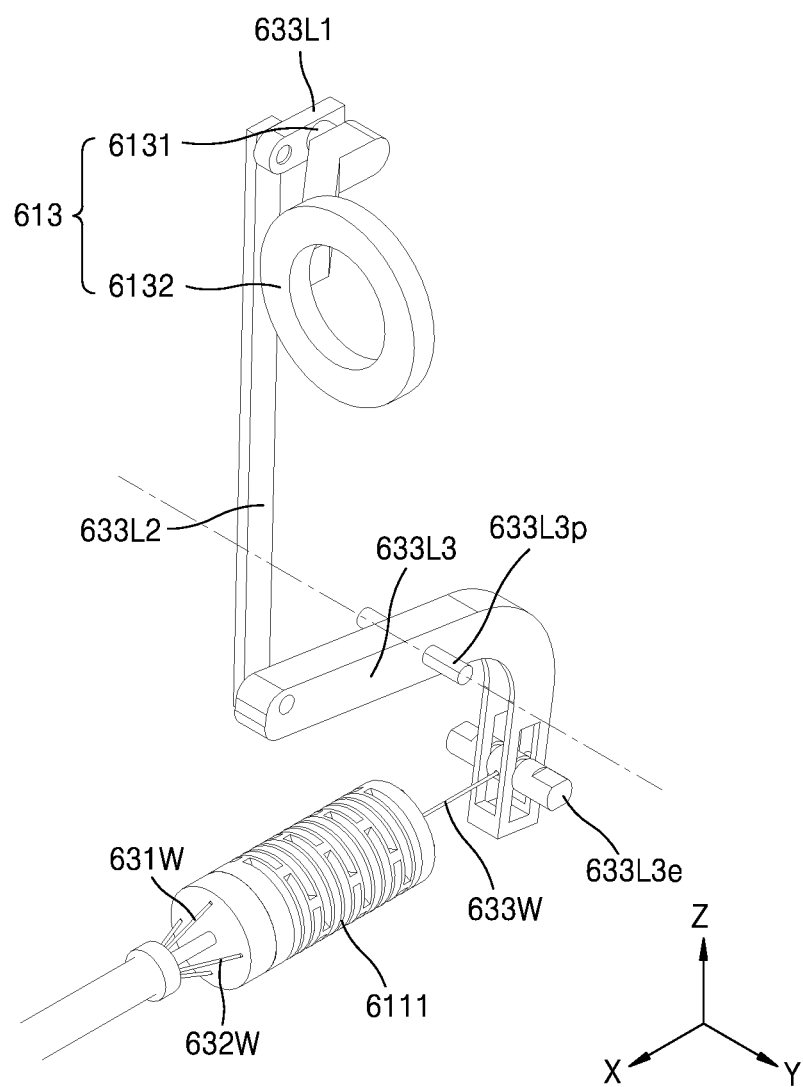

FIGS. 20 and 21 are diagrams of the surgical instrument 600 according to the sixth embodiment of the present invention. Referring to FIGS. 20 and 21, the surgical instrument 600 according to the sixth embodiment of the present invention includes a manipulator 610, an end tool 620, a power transfer unit 630, and a connection unit 640.

The manipulator 610 of the surgical instrument 600 includes a pitch/yaw operator 611 for controlling a pitch movement and a yaw movement of the end tool 620, and an actuation operator 613 for controlling an actuation movement of the end tool 620. Here, the pitch/yaw operator 611 includes a pitch/yaw rotating joint 6111 and a pitch/yaw operating grip 6112. Here, the pitch/yaw rotating joint 6111 may be configured to rotate about the Y-axis and the Z-axis, and the pitch/yaw operating grip 6112 is connected to the pitch/yaw rotating joint 6111 to rotate with the pitch/yaw rotating joint 6111. Here, the pitch/yaw rotating joint 6111 may be a curved type joint member.

In addition, the end tool 620 of the surgical instrument 600 uses the curved type joint member described above with reference to FIGS. 7A to 7D as a joint member 625. That is, the end tool 620 includes a first jaw (not shown), a second jaw 622, a jaw base 623, and the joint member 625. In addition, the power transfer unit 630 applied in the surgical instrument 600 according to the sixth embodiment includes one or more pitch wires 631W, one or more yaw wires 632W, and an actuation wire 633W.

Here, according to the surgical instrument of the sixth embodiment, a virtual center axis X1 of the pitch/yaw operating grip 6112 in the Z-axis direction and a virtual center axis X2 of the pitch/yaw rotating joint 6111 in the Z-axis direction are formed at the same distance from the end tool. In this case, the rotating center of the joint is placed on a portion where the user grips the pitch/yaw operating grip 6112.

Also, in the surgical instrument according to the sixth embodiment, the pitch/yaw operating grip 6112 is configured to be closer to the end tool 620 than the virtual center axis X2 of the pitch/yaw rotating joint 6111 in the Z-axis direction in at least one operating stage of the pitch/yaw operator 611. That is, in the surgical instrument according to the sixth embodiment of the present invention, the virtual center axis X1 of the pitch/yaw operating grip 6112 and the virtual center axis X2 of the pitch/yaw rotating joint 6111 in the Z-axis direction are formed on the same line, and thus, when the pitch/yaw operator 6111 rotates about the pitch/yaw rotating joint 6111 even a little from the state as shown in FIG. 20, the pitch/yaw operating grip 6112 is closer to the end tool 620 than the virtual center axis X2 of the pitch/yaw rotating joint 6111 in the Z-axis direction.

As described above, since the pitch/yaw operating grip 6112 is closer to the end tool 620 than the virtual center axis X2 of the pitch/yaw rotating joint 6111 in the Z-axis direction in at least one operating stage of the pitch/yaw operator 611, fingers and the hand of the user in front of the wrist joint of the user who is performing the pitch operation may move more than the wrist joint. That is, according to the related art illustrated in FIGS. 1A to 1D, the front part of the hand is fixed and the rear part of the hand, e.g., the wrist and arm, have to move a lot, which is largely different from the operation of the end tool, and thus, it is difficult to intuitively manipulate the surgical instrument. However, according to the present embodiment, intuitiveness in manipulating the manipulator for operating the end tool may be greatly improved due to the above-described characteristics.

Seventh Embodiment of a Surgical Instrument
(E1+H22c)

Hereinafter, the surgical instrument 700 according to the seventh embodiment of the present invention will be described below. Here, the surgical instrument 700 according to the seventh embodiment is different from the surgical instrument (see 500 of FIG. 19A) according to the fifth embodiment of the present invention, in that a virtual center axis X1 of a pitch/yaw operating grip 7112 of the surgical instrument 700 in the Z-axis direction is formed to be farther from an end tool 720 than a virtual center axis X2 of a pitch/yaw rotating joint 7111 in the Z-axis direction. Also, an actuation operator 713 is different from that of the surgical instrument (see 500 of FIG. 19A) according to the fifth embodiment of the present invention. The different structure from that of the fifth embodiment will be described later in more detail.

Figure 22:
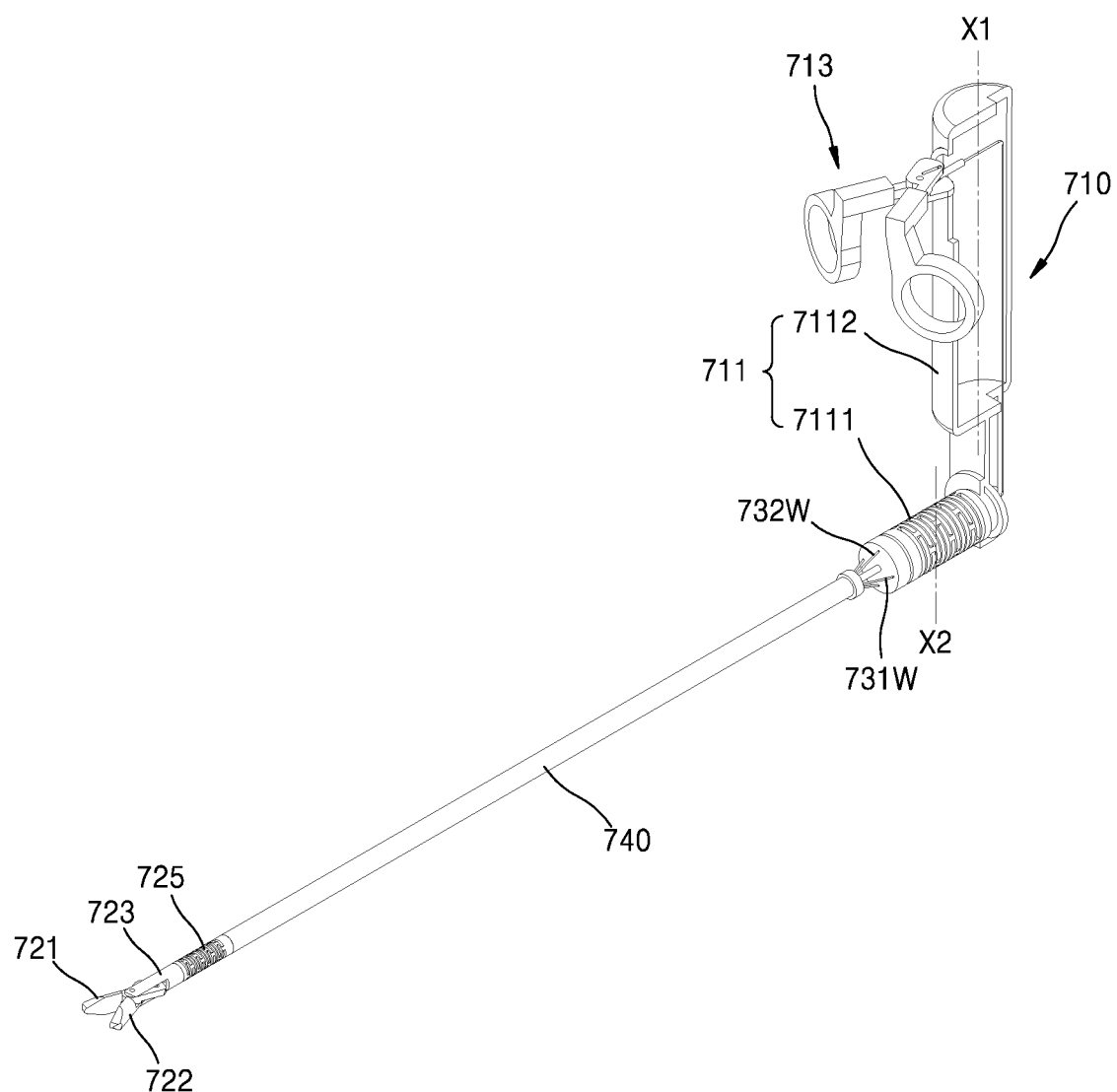
FIGS. 22, 23, and 24 are diagrams of a surgical instrument 700 according to the seventh embodiment of the present invention.
Figure 23:
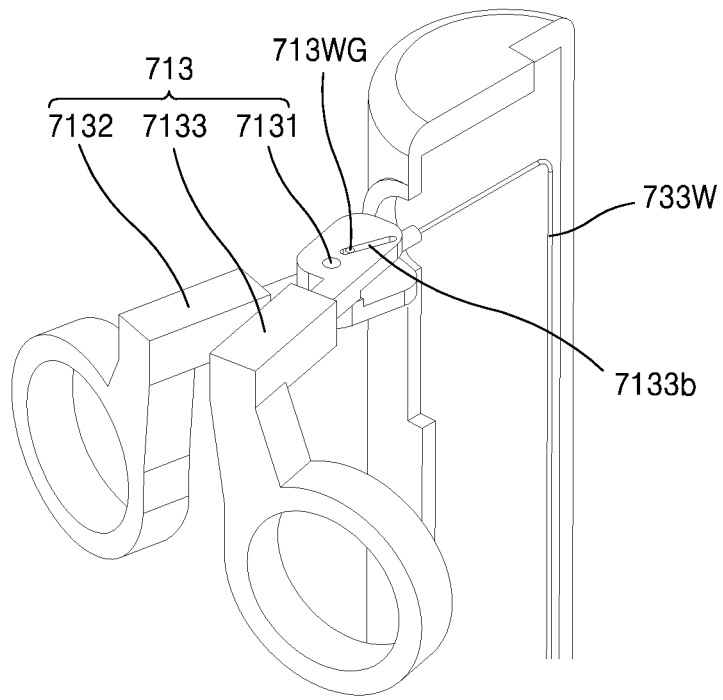
Figure 24:
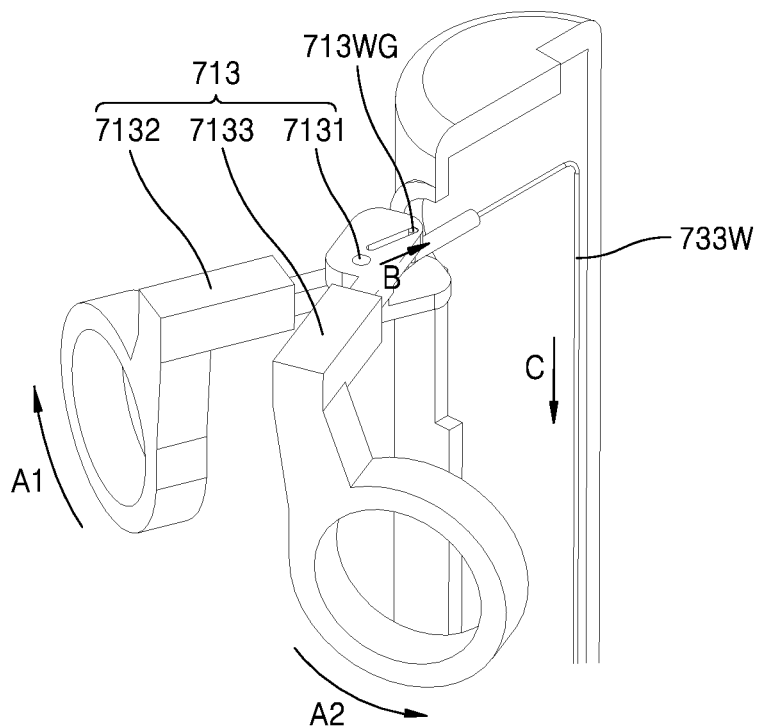

FIGS. 22, 23, and 24 are diagrams of the surgical instrument 700 according to the seventh embodiment of the present invention. Referring to FIGS. 22, 23, and 24, the surgical instrument 700 according to the seventh embodiment of the present invention includes a manipulator 710, an end tool 720, a power transfer unit 730, and a connection unit 740.

The manipulator 710 of the surgical instrument 700 includes the pitch/yaw operator 711 for controlling the pitch movement and the yaw movement of the end tool 720, and the actuation operator 713 for controlling the actuation movement of the end tool 720.

Here, the pitch/yaw operator 711 includes a pitch/yaw rotating joint 7111 and a pitch/yaw operating grip 7112. Here, the pitch/yaw rotating joint 7111 may be configured to rotate about the Y-axis and the Z-axis, and the pitch/yaw operating grip 7112 is connected to the pitch/yaw rotating joint 7111 to rotate with the pitch/yaw rotating joint 7111. The pitch/yaw rotating joint 7111 may be a combination of a curved type joint member and a ball joint. The combination type joint of the curved type joint member and the ball joint as above will be described later with reference to FIG. 46.

In addition, the actuation operator 713 includes an actuation rotating axis 7131, a first actuation rotating member 7132, a second actuation rotating member 7133, and an actuation guide pin 713WG. In detail, an axis through hole (not shown) is formed in each of the first and second actuation rotating members 7132 and 7133, and the actuation rotating axis 7131 is inserted through the axis through holes (not shown) of the first and second actuation rotating members 7132 and 7133. The first and second actuation rotating members 7132 and 7133 are rotated about the actuation rotating axis 7131.

In addition, a guide hole 7133b is formed at a side of the axis through hole (not shown) formed in each of the first and second actuation rotating members 7132 and 7133, and the actuation guide pin 713WG is inserted through the guide holes 7133b in the first and second actuation rotating members 7132 and 7133. Then, the actuation wire 733W is coupled to the actuation guide pin 713WG. Therefore, when the first actuation rotating member 7132 and the second actuation rotating member 7133 are rotated, the actuation guide pin 713WG connected to the first and second actuation rotating members 7132 and 7133 is moved along the guide hole 7133b, and accordingly, the actuation wire 733W linearly translates to perform the actuation operation.

For example, when one or both of the first and second actuation rotating members 7132 and 7133 are rotated in a direction A1 and/or A2 in FIG. 24 from the state of FIG. 23, the actuation guide pin 713WG is linearly moved in a direction of the arrow B, and thus, the actuation wire 733W connected to the actuation guide pin 713WG is linearly moved in a direction of the arrow C so that a first jaw 721 and a second jaw 722 of the end tool 720 connected to the actuation wire 733W may be unfolded to opposite sides. That is, the above example is one of various modified examples for transferring the actuation movement, which shows that the movement of the actuation operator 713 may be transferred to the end tool 720 via a simple wire structure, not only by the above described link structure, and other various structures may be provided to achieve the same objective.

Although the actuation operator 713 of the surgical instrument 700 according to the seventh embodiment includes the first actuation rotating member 7132 and the second actuation rotating member 7133 so that the actuation operation is performed by two fingers in FIGS. 22 to 24, the present embodiment is not limited thereto, and the actuation operator (see 513 of FIG. 19B or 613 of FIG. 21) performing the actuation operation by one finger as illustrated in FIG. 19B or 21 may be also applied to the present embodiment.

In addition, the end tool 720 of the surgical instrument 700 uses the curved type joint member described above with reference to FIGS. 7A to 7D as a joint member 725. That is, the end tool 720 includes the first jaw 721, the second jaw 722, a jaw base 723, and the joint member 725. In addition, the power transfer unit 730 applied in the surgical instrument 700 according to the seventh embodiment includes one or more pitch wires 731W, one or more yaw wires 732W, and the actuation wire 733W.

Here, according to the surgical instrument of the seventh embodiment, a virtual center axis X1 of the pitch/yaw operating grip 7112 of the surgical instrument 700 in the Z-axis direction is formed to be farther from the end tool than a virtual center axis X2 of the pitch/yaw rotating joint 7111 in the Z-axis direction. In this case, the front part of the hand of the user is fixed, and based on the front part, the rear part of the arm (elbow, etc.) is moved.

Also, in the surgical instrument according to the seventh embodiment, the pitch/yaw operating grip 7112 is configured to be closer to the end tool 720 than the virtual center axis X2 of the pitch/yaw rotating joint 7111 in the Z-axis direction in at least one operating stage of the pitch/yaw operator 711. That is, according to the surgical instrument of the seventh embodiment, the pitch/yaw operating grip 7112 is farther from the end tool 720 than the virtual center axis X2 of the pitch/yaw rotating joint 7111 in the Z-axis direction. However, if the pitch/yaw operator 711 is rotated by a predetermined angle or greater about the pitch/yaw rotating joint 7111 in order to perform the pitch or yaw movement, it is configured that a part of the pitch/yaw operating grip 7112 is closer to the end tool 720 than the virtual center axis X2 of the pitch/yaw rotating joint 7111 in the Z-axis direction.

As described above, since the pitch/yaw operating grip 7112 is closer to the end tool 720 than the virtual center axis X2 of the pitch/yaw rotating joint 7111 in the Z-axis direction in at least one operating stage of the pitch/yaw operator 711, fingers and the hand of the user in front of the wrist joint of the user who is performing the pitch operation may move more than the wrist joint. That is, according to the related art illustrated in FIGS. 1A to 1D, the front part of the hand is fixed and the rear part of the hand, e.g., the wrist and arm, have to move a lot, which is largely different from the operation of the end tool, and thus, it is difficult to intuitively manipulate the surgical instrument. However, according to the present embodiment, intuitiveness in manipulating the manipulator for operating the end tool may be greatly improved due to the above-described characteristics.

Eighth Embodiment of a Surgical Instrument
(E1+H23a)

Hereinafter, a surgical instrument 800 according to the eighth embodiment of the present invention will be described below. Here, the surgical instrument 800 according to the eighth embodiment of the present invention is different from the surgical instrument (see 100 of FIG. 2) described above according to the first embodiment, in that pitch/yaw operator 811 in which a pitch operator and a yaw operator of a manipulator 810 are integrally formed is provided to perform functions of both the pitch operator and the yaw operator, and the pitch/yaw operator 811 is formed on an extension line of an end tool 820, wherein the connection unit 840 is not straight, but curved at least once. In addition, the surgical instrument 800 according to the eighth embodiment of the present invention is characterized in that a virtual center axis X1 of a pitch/yaw operating grip 8112 of the surgical instrument 800 in the Z-axis direction is closer to the end tool 820 than a virtual center axis X2 of a pitch/yaw rotating joint 8111 in the Z-axis direction. The different structure from that of the first embodiment will be described later in more detail.

Figure 25:
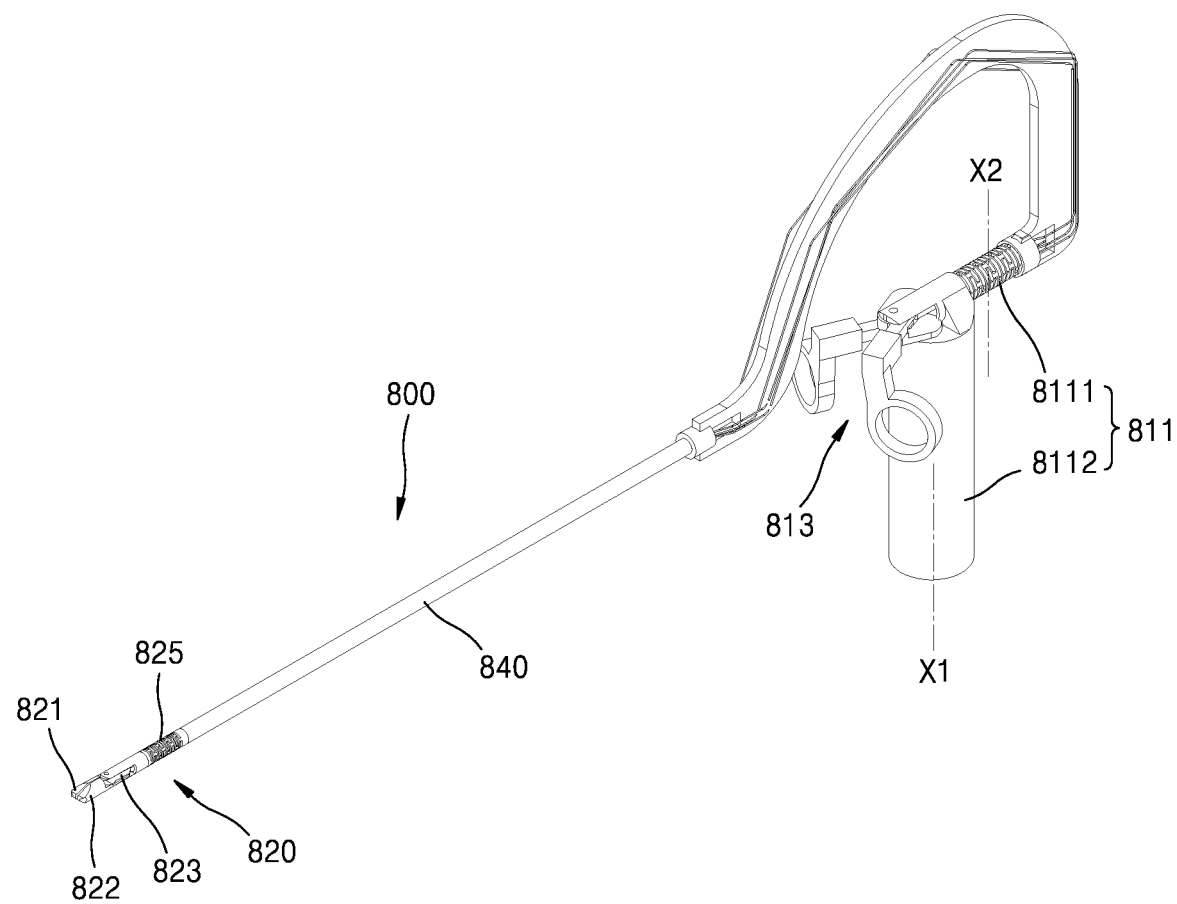
FIGS. 25, 26A, and 26B are diagrams of a surgical instrument (800) according to an eighth embodiment of the present invention.
Figure 26A:
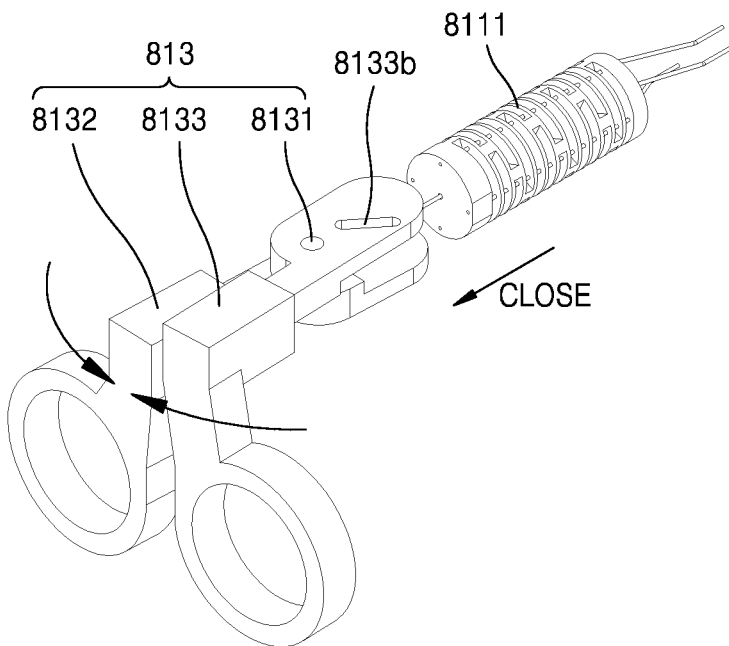
Figure 26B:
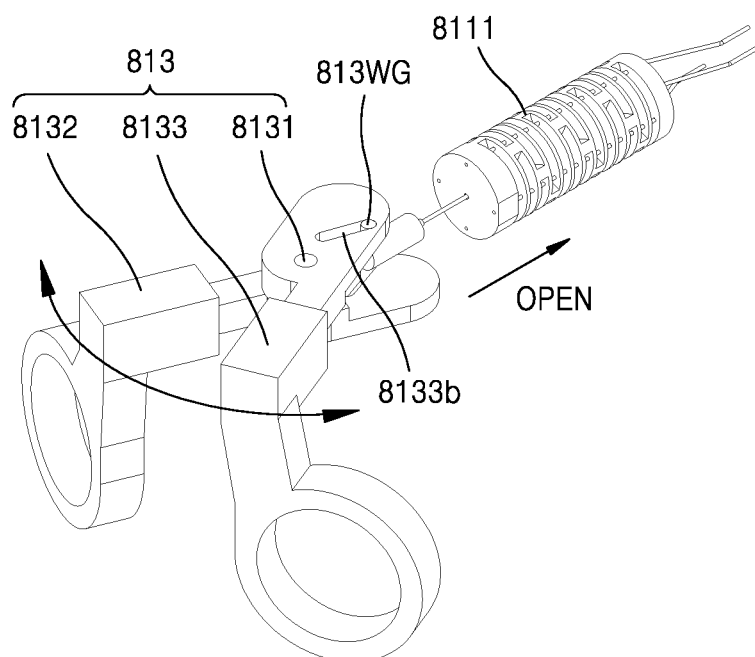

FIGS. 25, 26A, and 26B are diagrams of the surgical instrument 800 according to the eighth embodiment of the present invention. Referring to FIGS. 25, 26A, and 26B, the surgical instrument 800 according to the eighth embodiment of the present invention includes a manipulator 810, the end tool 820, a power transfer unit 830, and the connection unit 840.

The manipulator 810 of the surgical instrument 800 includes the pitch/yaw operator 811 for controlling the pitch movement and the yaw movement of the end tool 820, and an actuation operator 813 for controlling the actuation movement of the end tool 820.

Here, the pitch/yaw operator 811 includes a pitch/yaw rotating joint 8111 and a pitch/yaw operating grip 8112. Here, the pitch/yaw rotating joint 8111 may be configured to rotate about the Y-axis and the Z-axis, and the pitch/yaw operating grip 8112 is connected to the pitch/yaw rotating joint 8111 to rotate with the pitch/yaw rotating joint 8111. Here, the pitch/yaw rotating joint 8111 may be a curved type joint member.

In addition, the actuation operator 813 includes an actuation rotating axis 8131, a first actuation rotating member 8132, a second actuation rotating member 8133, and an actuation guide pin 813WG. The actuation operator 813 has a structure that is substantially identical with that of the actuation operator (see 713 of FIG. 23) according to the seventh embodiment.

That is, when the first actuation rotating member 8132 and the second actuation rotating member 8133 are rotated, the actuation guide pin 813WG connected to the first and second actuation rotating members 8132 and 8133 is moved along a guide hole 8133b, and accordingly, an actuation wire 833W linearly translates to perform the actuation operation.

Although the actuation operator 813 of the surgical instrument 800 according to the eighth embodiment includes the first actuation rotating member 8132 and the second actuation rotating member 8133 so that the actuation operation is performed by two fingers in FIGS. 25 to 27, the present embodiment is not limited thereto, and the actuation operator (see 513 of FIG. 19B or 613 of FIG. 21) performing the actuation operation by one finger as illustrated in FIG. 19B or 21 may be also applied to the present embodiment.

In addition, the end tool 820 of the surgical instrument 800 uses the curved type joint member described above with reference to FIGS. 7A to 7D as a joint member 825. That is, the end tool 820 includes a first jaw 821, a second jaw 822, a jaw base 823, and the joint member 825. In addition, the power transfer unit 830 applied in the surgical instrument 800 according to the eighth embodiment includes one or more pitch wires 831W, one or more yaw wires 832W, and an actuation wire 833W.

Here, the surgical instrument according to the eighth embodiment of the present invention 1) includes the pitch/yaw operator 811 in which the pitch operator and the yaw operator of the manipulator 810 are integrally formed so as to perform functions of both the pitch operator and the yaw operator, as described above. 2) In addition, the pitch/yaw operator 811 is formed on an extension line of an end tool 820, and the connection unit 840 is not straight, but is curved at least once.

In addition, in the surgical instrument according to the eighth embodiment of the present invention, the virtual center axis X1 of the pitch/yaw operating grip 8112 in the Z-axis direction is closer to the end tool 820 than the virtual center axis X2 of the pitch/yaw rotating joint 8111 in the Z-axis direction.

Therefore, in the surgical instrument according to the eighth embodiment, the pitch/yaw operating grip 8112 is configured to be closer to the end tool 820 than the virtual center axis X2 of the pitch/yaw rotating joint 8111 in the Z-axis direction in at least one operating stage of the pitch/yaw operator 811. That is, in the surgical instrument according to the eighth embodiment, since the virtual center axis X1 of the pitch/yaw operating grip 8112 in the Z-axis direction itself is closer to the end tool 820 than the virtual center axis X2 of the pitch/yaw rotating joint 8111 in the Z-axis direction, the pitch/yaw operating grip 8112 is closer to the end tool 820 than the virtual center axis X2 of the pitch/yaw rotating joint 8111 in the Z-axis direction in almost every operating stage of the pitch/yaw operator 811.

As described above, since the pitch/yaw operating grip 8112 is closer to the end tool 820 than the virtual center axis X2 of the pitch/yaw rotating joint 8111 in the Z-axis direction in at least one operating stage of the pitch/yaw operator 811, fingers and the hand of the user in front of the wrist joint of the user who is performing the pitch operation may move more than the wrist joint. That is, according to the related art illustrated in FIGS. 1A to 1D, the front part of the hand is fixed and the rear part of the hand, e.g., the wrist and arm, have to move a lot, which is largely different from the operation of the end tool, and thus, it is difficult to intuitively manipulate the surgical instrument. However, according to the present embodiment, intuitiveness in manipulating the manipulator for operating the end tool may be greatly improved due to the above-described characteristics.

Figure 27A:
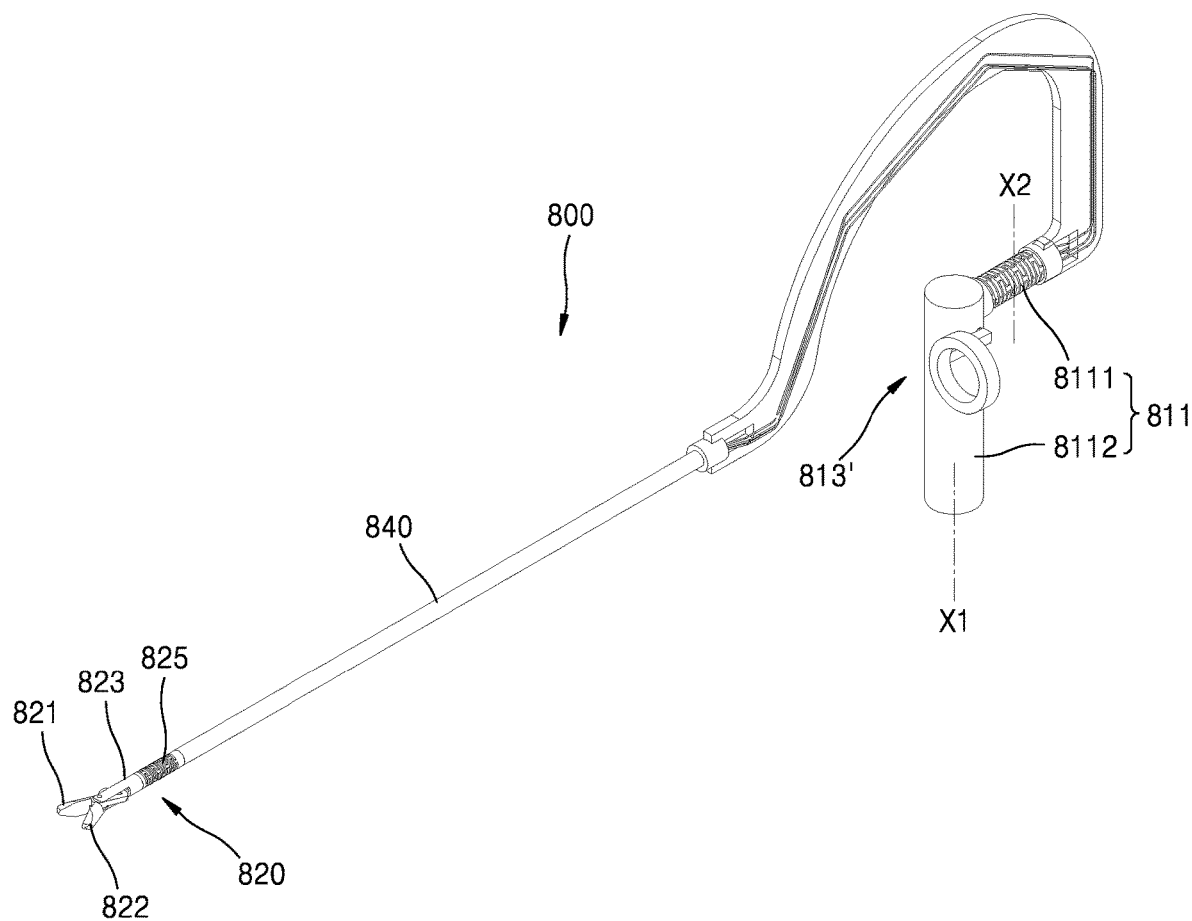
FIGS. 27A and 27B are diagrams of a surgical instrument (800) according to a modified example of the eighth embodiment of the present invention.
Figure 27B:
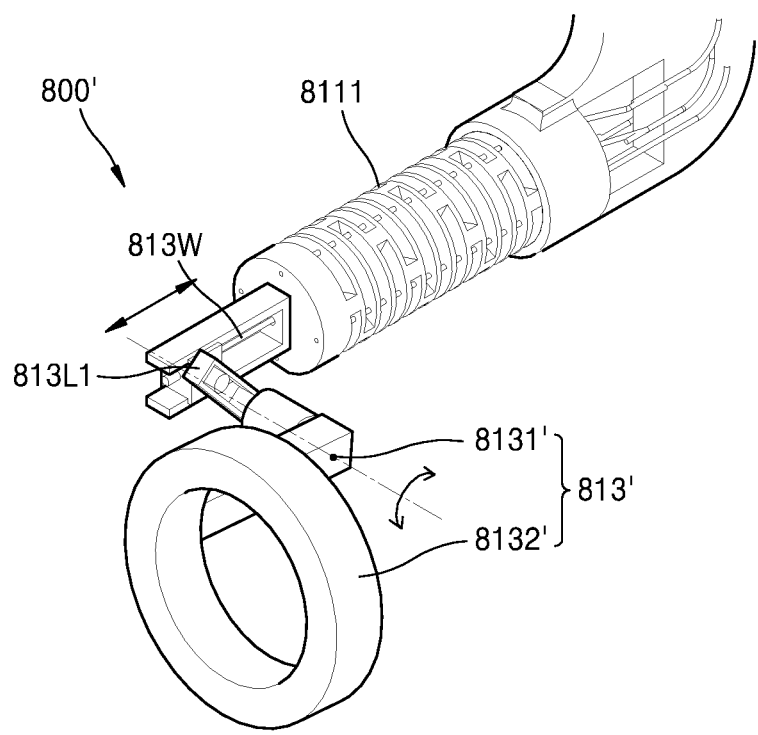

FIGS. 27A and 27B are diagrams of the surgical instrument 800 according to a modified example of the eighth embodiment of the present invention. Here, the surgical instrument 800 according to the modified example of the eighth embodiment is different from the surgical instrument (see 800 of FIG. 25) according to the eighth embodiment in that the actuation operation is performed by using one finger, not two fingers.

In detail, the manipulator 810 of the surgical instrument 800 includes the pitch/yaw operator 811 for controlling the pitch movement and the yaw movement of the end tool 820, and an actuation operator 813 for controlling the actuation movement of the end tool 820. The actuation operator 813 includes an actuation rotating axis 8131 and an actuation rotating member 8132. In addition, a first actuation link 813L1 may be connected to an end portion of the actuation rotating axis 8131, and an actuation wire 813W may be connected to an end portion of the first actuation link 813L1. In addition, an actuation guide pin (not shown) of the end tool 820 may be connected to the other end portion of the actuation wire 813W. According to the above configuration, the actuation movement may be performed only by one finger. The above example is a modified example for performing the operation of pushing and pulling the actuation wire 813W by the actuation operator 813, and another configuration for performing the above operation may be provided.

Ninth Embodiment of a Surgical Instrument (E1+H23b)

Hereinafter, a surgical instrument 900 according to the ninth embodiment of the present invention will be described below. Here, the surgical instrument 900 according to the ninth embodiment is different from the surgical instrument (see 800 of FIG. 25) according to the eighth embodiment of the present invention, in that a virtual center axis X1 of a pitch/yaw operating grip 9112 of the surgical instrument 900 in the Z-axis direction is formed on the same line as a virtual center axis X2 of a pitch/yaw rotating joint 9111 in the Z-axis direction.

Figure 28:
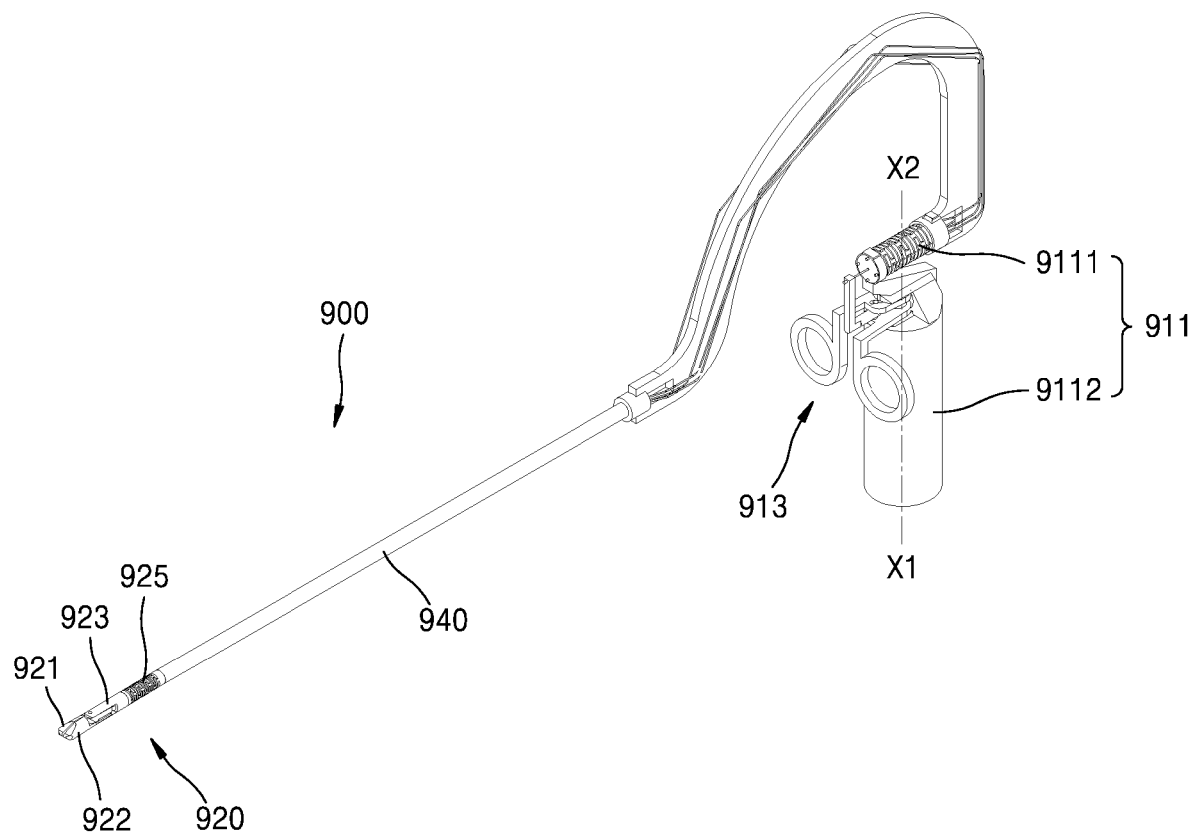
FIGS. 28, 29, and 30 are diagrams of a surgical instrument (900) according to a ninth embodiment of the present invention.
Figure 29:
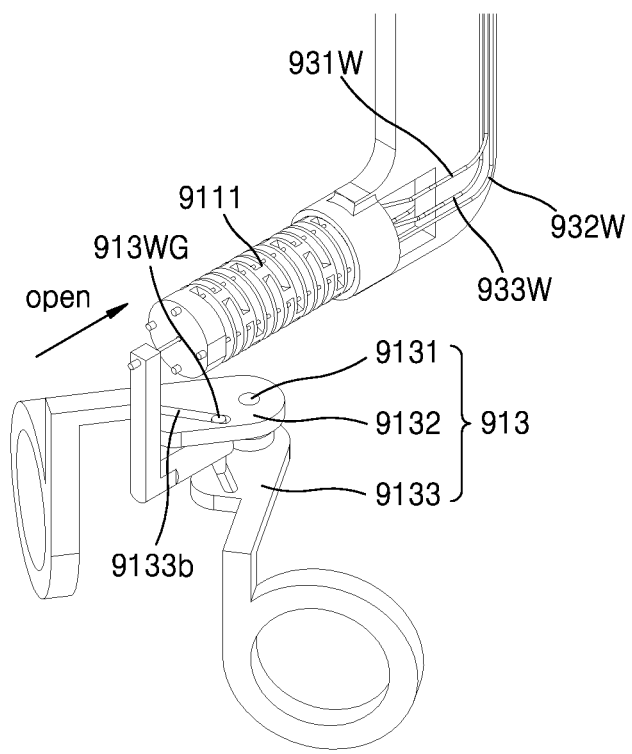
Figure 30:
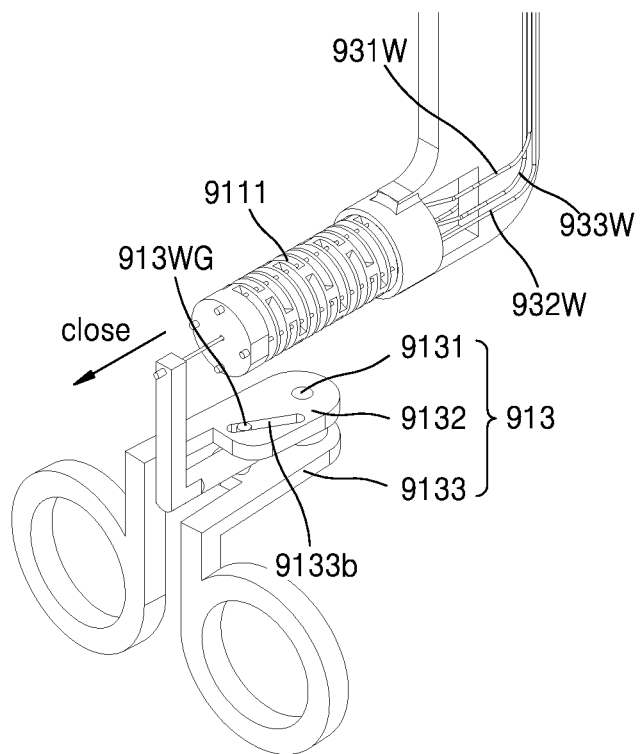

FIGS. 28, 29, and 30 are diagrams of the surgical instrument 900 according to the ninth embodiment of the present invention. Referring to FIGS. 28, 29, and 30, the surgical instrument 900 according to the ninth embodiment of the present invention includes a manipulator 910, an end tool 920, a power transfer unit 930, and a connection unit 940.

The manipulator 910 of the surgical instrument 900 includes the pitch/yaw operator 911 for controlling the pitch movement and the yaw movement of the end tool 920, and an actuation operator 913 for controlling the actuation movement of the end tool 920.

Here, the pitch/yaw operator 911 includes a pitch/yaw rotating joint 9111 and a pitch/yaw operating grip 9112. Here, the pitch/yaw rotating joint 9111 may be configured to rotate about the Y-axis and the Z-axis, and the pitch/yaw operating grip 9112 is connected to the pitch/yaw rotating joint 9111 to rotate with the pitch/yaw rotating joint 9111. Here, the pitch/yaw rotating joint 9111 may be a curved type joint member.

In addition, the actuation operator 913 includes an actuation rotating axis 9131, a first actuation rotating member 9132, a second actuation rotating member 9133, and an actuation guide pin 913WG. The actuation operator 913 has a structure that is substantially identical with that of the actuation operator (see 713 of FIG. 23) according to the seventh embodiment.

That is, when the first actuation rotating member 9132 and the second actuation rotating member 9133 are rotated, the actuation guide pin 913WG connected to the first and second actuation rotating members 9132 and 9133 is moved along a guide hole 9133b, and accordingly, an actuation wire 933W linearly translates to perform the actuation operation. That is, FIG. 29 shows the actuation operator 913 in a state where a first jaw 921 and a second jaw 922 are unfolded, and FIG. 30 shows the actuation operator 913 in a state where the first jaw 921 and the second jaw 922 are folded.

Although the actuation operator 913 of the surgical instrument 900 according to the ninth embodiment includes the first actuation rotating member 9132 and the second actuation rotating member 9133 so that the actuation operation is performed by two fingers in FIGS. 28 to 30, the present embodiment is not limited thereto, and the actuation operator (see 513 of FIG. 19B or 613 of FIG. 21) performing the actuation operation by one finger as illustrated in FIG. 19B or 21 may be also applied to the present embodiment.

In addition, the end tool 920 of the surgical instrument 900 uses the curved type joint member described above with reference to FIGS. 7A to 7D as a joint member 925. That is, the end tool 920 includes the first jaw 921, the second jaw 922, a jaw base 923, and the joint member 925. In addition, the power transfer unit 930 applied in the surgical instrument 900 according to the ninth embodiment includes one or more pitch wires 931W, one or more yaw wires 932W, and an actuation wire 933W.

Here, according to the surgical instrument of the ninth embodiment, a virtual center axis X1 of the pitch/yaw operating grip 9112 in the Z-axis direction and a virtual center axis X2 of the pitch/yaw rotating joint 9111 in the Z-axis direction are formed at the same distance from the end tool. In this case, the rotating center of the joint is placed on a portion where the user grips the pitch/yaw operating grip 9112.

Also, in the surgical instrument according to the ninth embodiment, the pitch/yaw operating grip 9112 is configured to be closer to the end tool 920 than the virtual center axis X2 of the pitch/yaw rotating joint 9111 in the Z-axis direction in at least one operating stage of the pitch/yaw operator 911. That is, in the surgical instrument according to the ninth embodiment of the present invention, the virtual center axis X1 of the pitch/yaw operating grip 9112 and the virtual center axis X2 of the pitch/yaw rotating joint 9111 in the Z-axis direction are formed on the same line, and thus, when the pitch/yaw operator 911 rotates about the pitch/yaw rotating joint 6111 even a little from the state as shown in FIG. 25, the pitch/yaw operating grip 9112 is closer to the end tool 920 than the virtual center axis X2 of the pitch/yaw rotating joint 9111 in the Z-axis direction.

As described above, since the pitch/yaw operating 9112 is closer to the end tool 920 than the virtual center axis X2 of the pitch/yaw rotating joint 9111 in the Z-axis direction in at least one operating stage of the pitch/yaw operator 911, fingers and the hand of the user in front of the wrist joint of the user who is performing the pitch operation may move more than the wrist joint. That is, according to the related art illustrated in FIGS. 1A to 1D, the front part of the hand is fixed and the rear part of the hand, e.g., the wrist and arm, have to move a lot, which is largely different from the operation of the end tool, and thus, it is difficult to intuitively manipulate the surgical instrument. However, according to the present embodiment, intuitiveness in manipulating the manipulator for operating the end tool may be greatly improved due to the above-described characteristics.

Tenth Embodiment of a Surgical Instrument (E1+H23c)

Hereinafter, a surgical instrument 1000 according to the tenth embodiment of the present invention will be described below. Here, the surgical instrument 1000 according to the tenth embodiment is different from the surgical instrument (see 800 of FIG. 25) according to the eighth embodiment of the present invention, in that a virtual center axis X1 of a pitch/yaw operating grip 10112 of the surgical instrument 1000 in the Z-axis direction is formed to be farther from an end tool 1020 than a virtual center axis X2 of a pitch/yaw rotating joint 10111 in the Z-axis direction.

Figure 31:
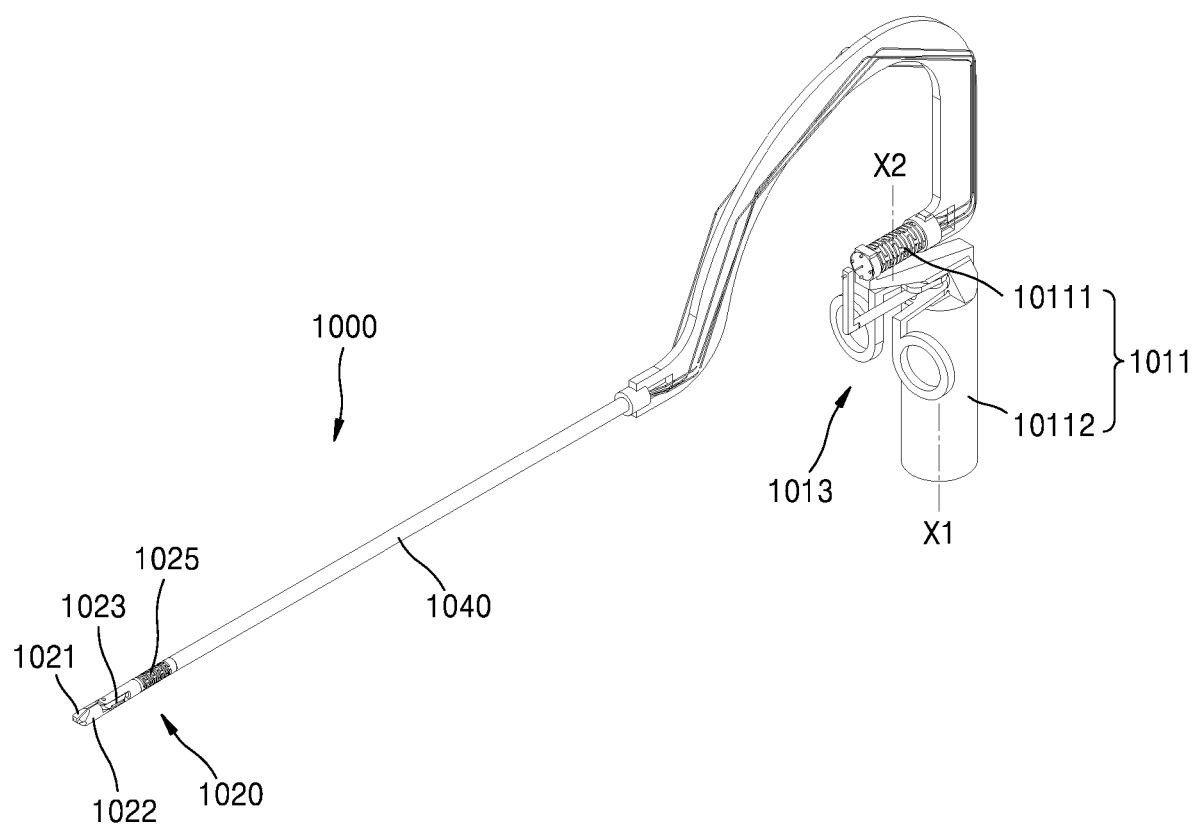
FIGS. 31 and 32 are diagrams of a surgical instrument (1000) according to a tenth embodiment of the present invention.
Figure 32:
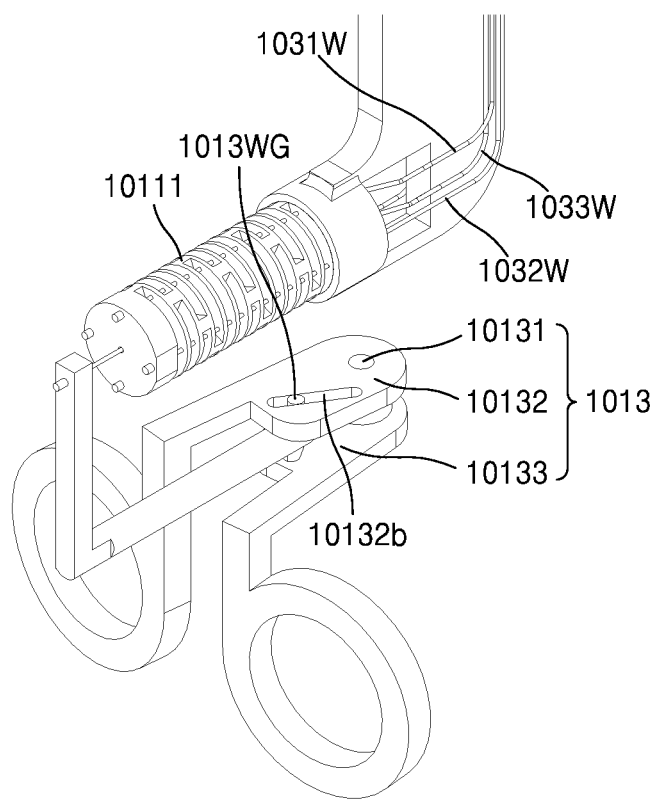

FIGS. 31 and 32 are diagrams of the surgical instrument 1000 according to the tenth embodiment of the present invention. Referring to FIGS. 31 and 32, the surgical instrument 1000 according to the tenth embodiment of the present invention includes a manipulator 1010, an end tool 1020, a power transfer unit 1030, and a connection unit 1040.

The manipulator 1010 of the surgical instrument 1000 includes the pitch/yaw operator 1011 for controlling the pitch movement and the yaw movement of the end tool 1020, and an actuation operator 1013 for controlling the actuation movement of the end tool 1020.

Here, the pitch/yaw operator 1011 includes a pitch/yaw rotating joint 10111 and a pitch/yaw operating grip 10112. Here, the pitch/yaw rotating joint 10111 may be configured to rotate about the Y-axis and the Z-axis, and the pitch/yaw operating grip 10112 is connected to the pitch/yaw rotating joint 10111 to rotate with the pitch/yaw rotating joint 10111. Here, the pitch/yaw rotating joint 10111 may be a curved type joint member.

In addition, the actuation operator 1013 includes an actuation rotating axis 10131, a first actuation rotating member 10132, a second actuation rotating member 10133, and an actuation guide pin 1013WG. The actuation operator 1013 has a structure that is substantially identical with that of the actuation operator (see 713 of FIG. 23) according to the seventh embodiment.

That is, when the first actuation rotating member 10132 and the second actuation rotating member 10133 are rotated, the actuation guide pin 1013WG connected to the first and second actuation rotating members 10132 and 10133 is moved along the guide hole 10133b, and accordingly, the actuation wire 1033W linearly translates to perform the actuation operation. Here, FIG. 32 shows the actuation operator 1013 in a state where a first jaw 1021 and a second jaw 1022 are unfolded.

Although the actuation operator 1013 of the surgical instrument 1000 according to the tenth embodiment includes the first actuation rotating member 10132 and the second actuation rotating member 10133 so that the actuation operation is performed by two fingers in FIGS. 31 and 32, the present embodiment is not limited thereto, and the actuation operator (see 513 of FIG. 19B or 613 of FIG. 21) performing the actuation operation by one finger as illustrated in FIG. 19B or 21 may be also applied to the present embodiment.

In addition, the end tool 1020 of the surgical instrument 1000 uses the curved type joint member described above with reference to FIGS. 7A to 7D as a joint member 1025. That is, the end tool 1020 includes the first jaw 1021, the second jaw 1022, a jaw base 1023, and the joint member 1025. In addition, the power transfer unit 1030 applied in the surgical instrument 1000 according to the tenth embodiment includes one or more pitch wires 1031W, one or more yaw wires 1032W, and an actuation wire 1033W.

Here, according to the surgical instrument of the tenth embodiment, a virtual center axis X1 of the pitch/yaw operating grip 10112 of the surgical instrument 1000 in the Z-axis direction is formed to be farther from the end tool than a virtual center axis X2 of the pitch/yaw rotating joint 10111 in the Z-axis direction. In this case, the front part of the hand of the user is fixed, and based on the front part, the rear part of the arm (elbow, etc.) is moved.

Also, in the surgical instrument according to the tenth embodiment, the pitch/yaw operating grip 10112 is configured to be closer to the end tool 1020 than the virtual center axis X2 of the pitch/yaw rotating joint 10111 in the Z-axis direction in at least one operating stage of the pitch/yaw operator 1011. That is, according to the surgical instrument of the tenth embodiment, the pitch/yaw operating grip 10112 is farther from the end tool 1020 than the virtual center axis X2 of the pitch/yaw rotating joint 10111 in the Z-axis direction. However, if the pitch/yaw operator 1011 is rotated by a predetermined angle or greater about the pitch/yaw rotating joint 10111 in order to perform the pitch or yaw movement, it is configured that a part of the pitch/yaw operating grip 10112 is closer to the end tool 1020 than the virtual center axis X2 of the pitch/yaw rotating joint 10111 in the Z-axis direction.

As described above, since the pitch/yaw operating grip 10112 is closer to the end tool 1020 than the virtual center axis X2 of the pitch/yaw rotating joint 10111 in the Z-axis direction in at least one operating stage of the pitch/yaw operator 1011, fingers and the hand of the user in front of the wrist joint of the user who is performing the pitch operation may move more than the wrist joint. That is, according to the related art illustrated in FIGS. 1A to 1D, the front part of the hand is fixed and the rear part of the hand, e.g., the wrist and arm, have to move a lot, which is largely different from the operation of the end tool, and thus, it is difficult to intuitively manipulate the surgical instrument. However, according to the present embodiment, intuitiveness in manipulating the manipulator for operating the end tool may be greatly improved due to the above-described characteristics.

Modified Examples of the End Tool in the Surgical Instrument

Characteristics of the end tool according to the present invention are as follows. Wires are located at opposite ends of a cross-section of an end tool joint, and thus, when one of the wires is pulled, the end tool is curved towards that side. That is, since pitch wires and yaw wires are located at four directions of the cross-section and an actuation wire penetrates through a center of the cross-section, a pitch operation, a yaw operation, and an actuation operation may be performed and each of the operations is performed independently without affecting the other operations. There are a plurality of structures for implementing the above characteristics, and detailed modified examples are provided below. The modified examples that will be described below are some of various modified examples capable of implementing the above-described characteristics, and although not described herein, various examples capable of implementing the characteristics may be provided, and these examples are appreciated to be included in the scope of the present invention.

Hereinafter, various modified examples of the end tool in the surgical instrument according to the present invention will be described below. A node type joint member, a gear type joint member, etc. in addition to the curved type joint member illustrated in FIG. 2, etc. may be applied as the end tool of the surgical instrument according to the present invention. The above node type joint member or the gear type joint member may be used because the end tool of the surgical instrument according to the present invention is configured to perform the pitch movement or the yaw movement by pushing and pulling the wires. That is, when the pitch wire or the yaw wire is pulled or pushed, a rotation corresponding to the pitch or yaw occurs in the joint member. Hereinafter, this will be described below in more detail.

Figure 33:
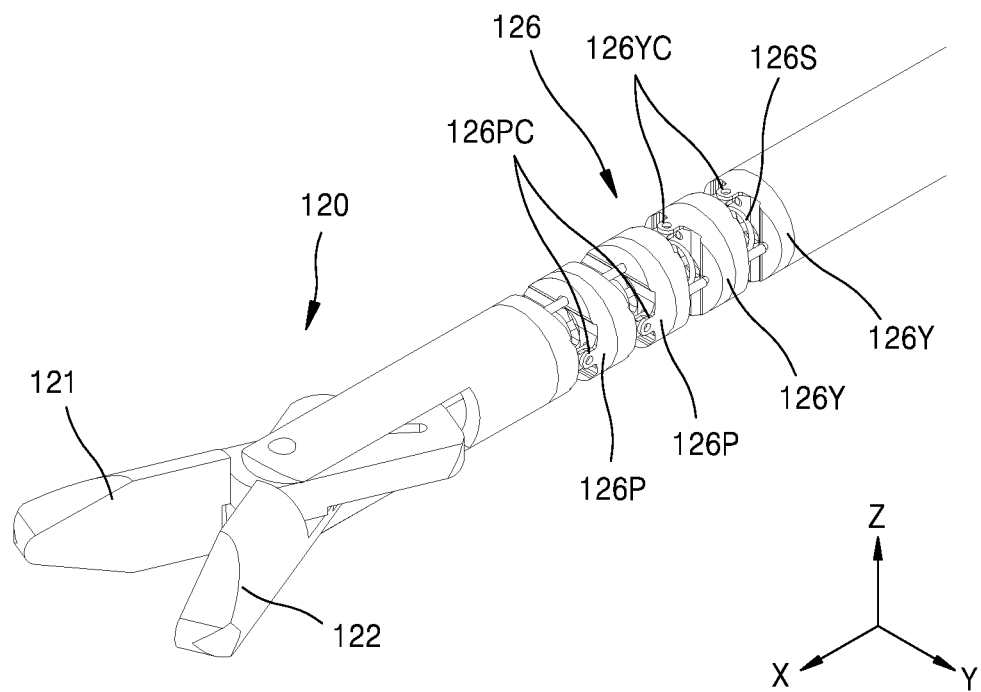
FIG. 33 is a diagram showing a first modified example of an end tool of the surgical instrument of FIG. 2, etc.

FIG. 33 is a diagram showing a first modified example of the end tool of the surgical instrument of FIG. 2, etc. (node type 1).

Referring to FIG. 33, a first modified example of the end tool in the surgical instrument uses a node type joint member as the joint member 126 of the end tool 120. That is, in the end tool (see 120 of FIG. 7) of the surgical instrument illustrated in FIGS. 2 and 7, the joint member (see 125 of FIG. 7) for performing the pitch operation, the yaw operation, and the actuation operation by using the curved type joint member is provided, whereas a joint member 126 for performing the pitch operation and the yaw operation by using the node type joint member is provided.

In detail, the joint member 126 includes one or more pitch nodes 126P performing as a pitch axis, and one or more yaw nodes 126Y performing as a yaw axis. Here, the pitch node 126P includes a pitch connector 126PC that protrudes from a diameter of the pitch node 126P in the Y-axis direction towards the end tool 120 to be connected to neighboring joints, and the yaw node 126Y includes a yaw connector 126YC that protrudes from a diameter of the yaw node 126Y in the Z-axis direction towards the end tool 120 to be connected to neighboring joints.

Therefore, in FIG. 33, the pitch node 126P of the node type joint member 126 is formed to be rotatable about the Y-axis, and may be a rotating center of the pitch movement. In addition, the yaw node 126Y of the node type joint member 126 is formed to be rotatable about the Z-axis, and may be a rotating center of the yaw movement.

In addition, the present modified example may further include an elastic member 126S. That is, the elastic member 126S is accommodated in the pitch node 126P and the yaw node 126Y to provide a predetermined elastic force in a direction in which the node type joint member 126 returns to the original location.

Figure 34:
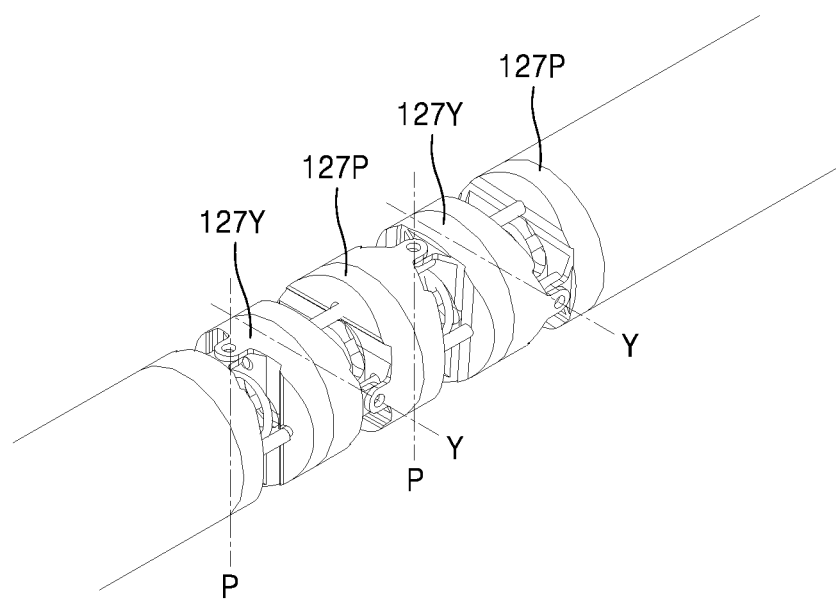
FIGS. 34 and 35 are diagrams showing a second modified example of the end tool of the surgical instrument of FIG. 2, etc.
Figure 35:
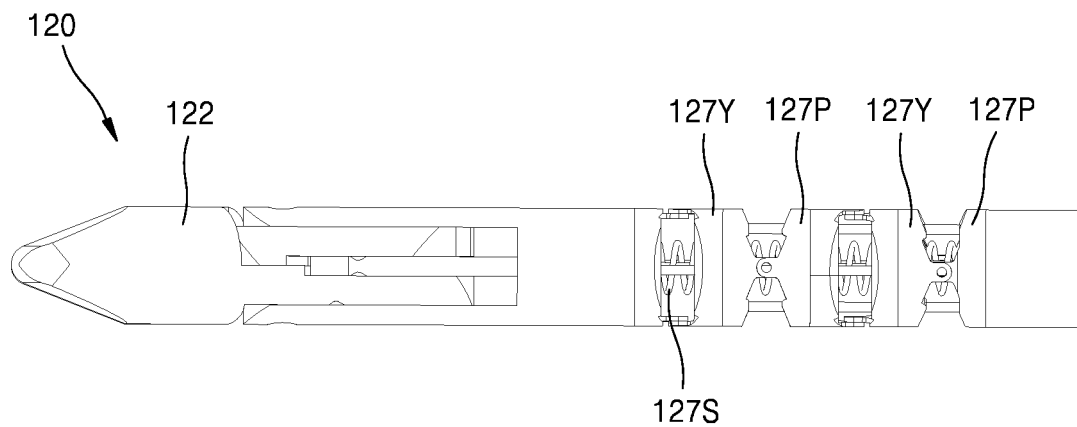

FIGS. 34 and 35 are diagrams showing a second modified example of the end tool of the surgical instrument of FIG. 2, etc. (Node type 2)

Referring to FIGS. 34 and 35, a second modified example of the end tool in the surgical instrument uses a node type joint member as a joint member 127 of the end tool 120. That is, in the end tool (see 120 of FIG. 7) of the surgical instrument illustrated in FIGS. 2 and 7, the joint member (see 125 of FIG. 7) for performing the pitch operation, the yaw operation, and the actuation operation by using the curved type joint member is provided, whereas a joint member 127 for performing the pitch operation and the yaw operation by using the node type joint member is provided.

In detail, the joint member 127 includes one or more pitch nodes 127P performing as a pitch axis, and one or more yaw nodes 127Y performing as a yaw axis. Here, the pitch node 127P includes a pitch connector 127PC that protrudes from a diameter of the pitch node 127P in the Y-axis direction towards the end tool 120 to be connected to neighboring joints, and the yaw node 126Y includes a yaw connector 127YC that protrudes from a diameter of the yaw node 127Y in the Z-axis direction towards the end tool 120 to be connected to neighboring joints.

Therefore, in FIG. 34, the pitch node 127P of the node type joint member 127 is formed to be rotatable in an up-and-down direction about the Y-axis, and may be a rotating center of the pitch movement. In addition, the yaw node 127Y of the node type joint member 127 is formed to be rotatable in a left-and-right direction about the Z-axis, and may be a rotating center of the yaw movement.

Here, the present modified example is characterized in that the pitch nodes 127P and the yaw nodes 127Y are alternately formed with each other. That is, as shown in FIG. 34, the joints may be formed in an order of, that is, the pitch node 127P, the yaw node 127Y, the pitch node 127P, and the yaw node 127Y. In addition, the present modified example may further include an elastic member 127S. That is, the elastic member 127S is accommodated in the pitch node 127P and the yaw node 127Y to provide a predetermined elastic force in a direction in which the node type joint member 127 returns to the original location.

Figure 36:
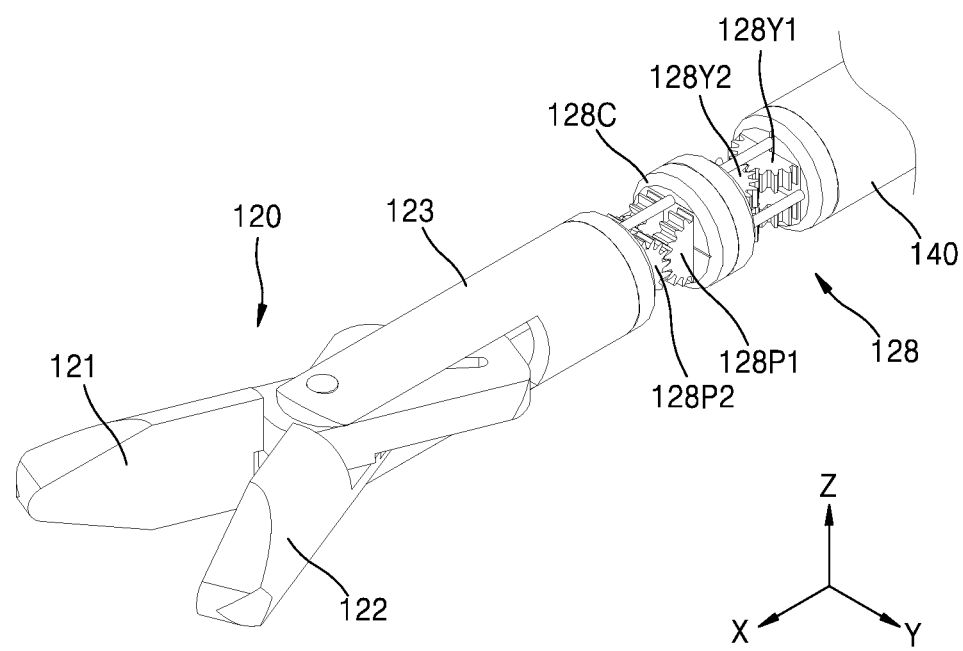
FIGS. 36 to 38 are diagrams showing a third modified example of the end tool of the surgical instrument of FIG. 2, etc.
Figure 37:
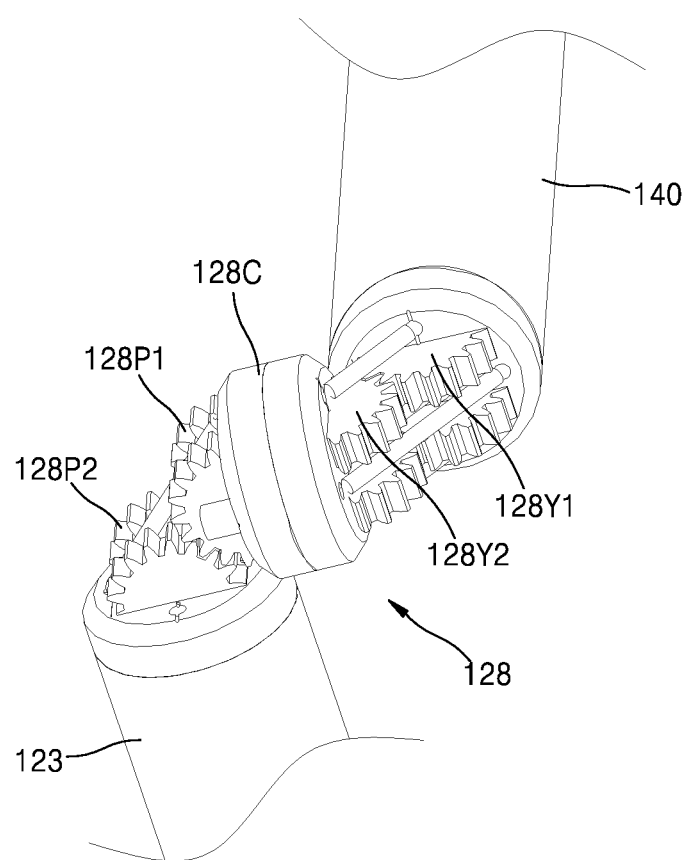
Figure 38:
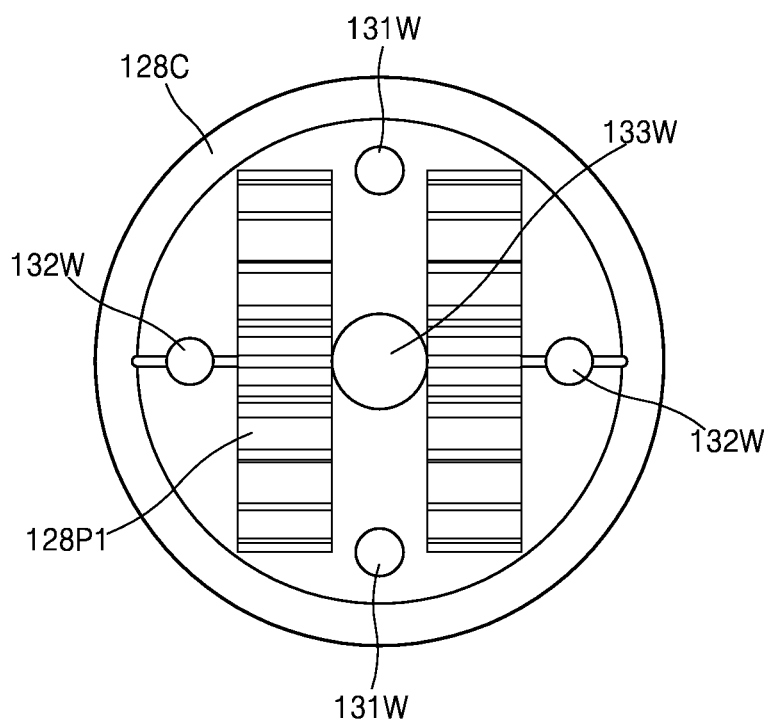

FIGS. 36 to 38 are diagrams showing a third modified example of the end tool of the surgical instrument of FIG. 2, etc. (gear type).

Referring to FIGS. 36 to 38, a third modified example of the end tool in the surgical instrument uses a gear type joint member as a joint member 128 of the end tool 120. That is, in the end tool (see 120 of FIG. 7) of the surgical instrument illustrated in FIGS. 2 and 7, the joint member (see 125 of FIG. 7) for performing the pitch operation, the yaw operation, and the actuation operation by using the curved type joint member is provided, whereas a joint member 128 for performing the pitch operation and the yaw operation by using the gear type joint member is provided.

In detail, the joint member 128 includes first and second pitch gears 128P1 and 128P2 performing the pitch operation, and first and second yaw gears 128Y1 and 128Y2 performing the yaw operation. In addition, the joint member 128 further include an end tool connection member 128C that connects the connection unit 140 to the jaw base 123. Here, the second pitch gear 128P2 is formed to be rotatable about an axis of the first pitch gear 128P1 to perform the pitch operation, and the second yaw gear 128Y2 is formed to be rotatable about an axis of the first yaw gear 128Y1 to perform the yaw operation.

Here, the first yaw gear 128Y1 is fixed at one end portion of the connection unit 140. In addition, the second yaw gear 128Y2 is fixedly formed on the end tool connection member 128C, and the second yaw gear 128Y2 is rotated with respect to the first yaw gear 128Y1 when opposite sides of the yaw wire are pushed and pulled, so as to rotate the jaw base 123, the first jaw 121, and the second jaw 122 connected to the end tool connection member 128C about the axis of the first yaw gear 128Y1.

In addition, the first pitch gear 128P1 is fixedly formed on the end tool connection member 128C. In addition, the second pitch gear 128P2 is fixedly formed on the jaw base 123, and the second pitch gear 128P2 is rotated with respect to the first pitch gear 128P1 when opposite sides of the pitch wire are pulled and pushed so as to rotate the jaw base 123, the first jaw 121, and the second jaw 122 about the axis of the first pitch gear 128P1.

Therefore, the second pitch gear 128P2 of the joint member 128 is formed to be rotatable about the axis of the first pitch gear 128P1, and may be a rotating center of the pitch movement. In addition, the second yaw gear 128Y2 of the joint member 128 is formed to be rotatable about the axis of the first yaw gear 128Y1, and may be a rotating center of the yaw movement.

Modified Examples of a Manipulator Joint in the Surgical Instrument

As shown in FIG. 2, the pitch operating joint according to the present invention is characterized in that the pitch operation is performed through the rotation in the Y-axis direction, the pitch and yaw wires are located at four directions in the cross-section of the joint and the actuation wire is located at the center, and the pitch operation by the pitch operating joint, the yaw operation by the yaw operator, and the actuation operation by the actuation operator may be performed independently without affecting the other operations. There may be a plurality of detailed structures capable of implementing the above characteristics, and modified examples thereof will be described in detail below. The modified examples that will be described below are some of various modified examples capable of implementing the above-described characteristics, and although not described herein, various examples capable of implementing the characteristics may be provided, and these examples are appreciated to be included in the scope of the present invention.

Figure 39:
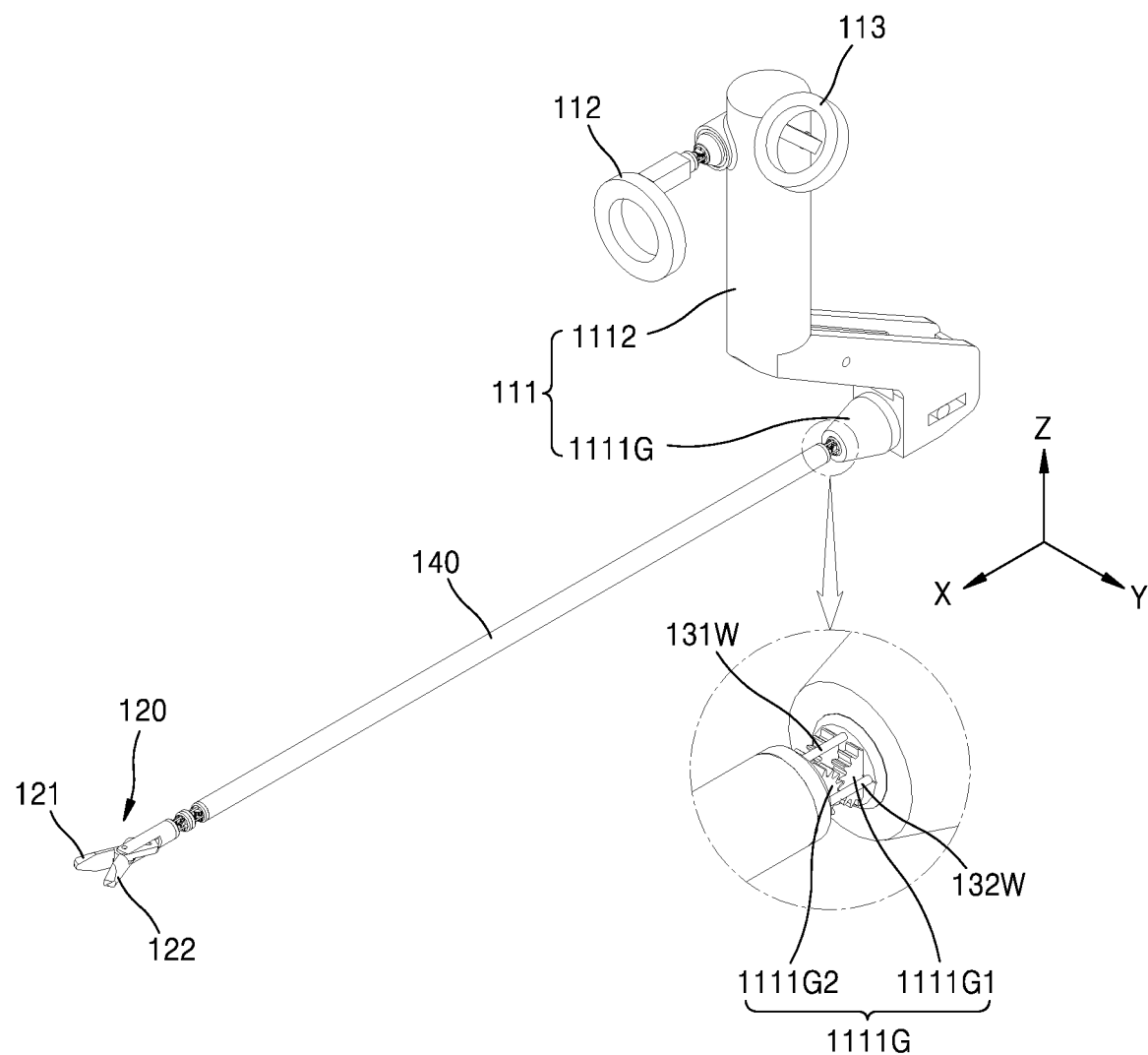
FIG. 39 is a diagram showing a first modified example of a pitch driving joint of the surgical instrument of FIG. 2, etc.

FIG. 39 is a diagram showing a first modified example of a pitch operating joint (see 1111 of FIG. 2) of the surgical instrument of FIG. 2, etc. (gGear type—G).

Referring to FIG. 39, the first modified example of the pitch operating joint in the surgical instrument uses a gear type joint member as a pitch operating joint 1111G of the manipulator 110. That is, in the manipulator (see 110 of FIG. 2) of the surgical instrument illustrated in FIGS. 2 and 3, the pitch operating joint (see 1111 of FIG. 2) for performing the pitch operation of the manipulator is configured by using the curved type joint member, whereas the pitch operating joint 1111G for performing the pitch operation is configured by using a gear type joint member according to the present modified example.

In detail, the pitch operating joint 1111G includes first and second pitch gears 1111G1 and 1111G2 performing as pitch operating joints. Here, the first pitch gear 1111G1 and the second pitch gear 1111G2 are formed to be rotatable about the axes of each other to perform the pitch operation.

Here, the first pitch gear 1111G1 is fixedly formed at an end portion of the pitch operating joint 1111G and the second pitch gear 1111G2 is fixedly formed at an end portion of the connection unit 140, and thus, when the pitch operating grip 1112 is rotated, the first pitch gear 1111G1 and the end tool 120 connected to the first pitch gear 1111G1 are also rotated about the Y-axis direction.

That is, the first pitch gear 1111G1 of the pitch operating joint 1111G is formed to be rotatable about the axis of the second pitch gear 1111G2 along with the second pitch gear 1111G2, and thus, may be a rotating center of the pitch movement.

Here, since the actuation wire (not shown) passes through the centers of the two pitch wires 131W that are in parallel with each other and the centers of the two yaw wires 132W that are in parallel with each other, and is not affected by the pitch movement and the yaw movement.

Figure 40:
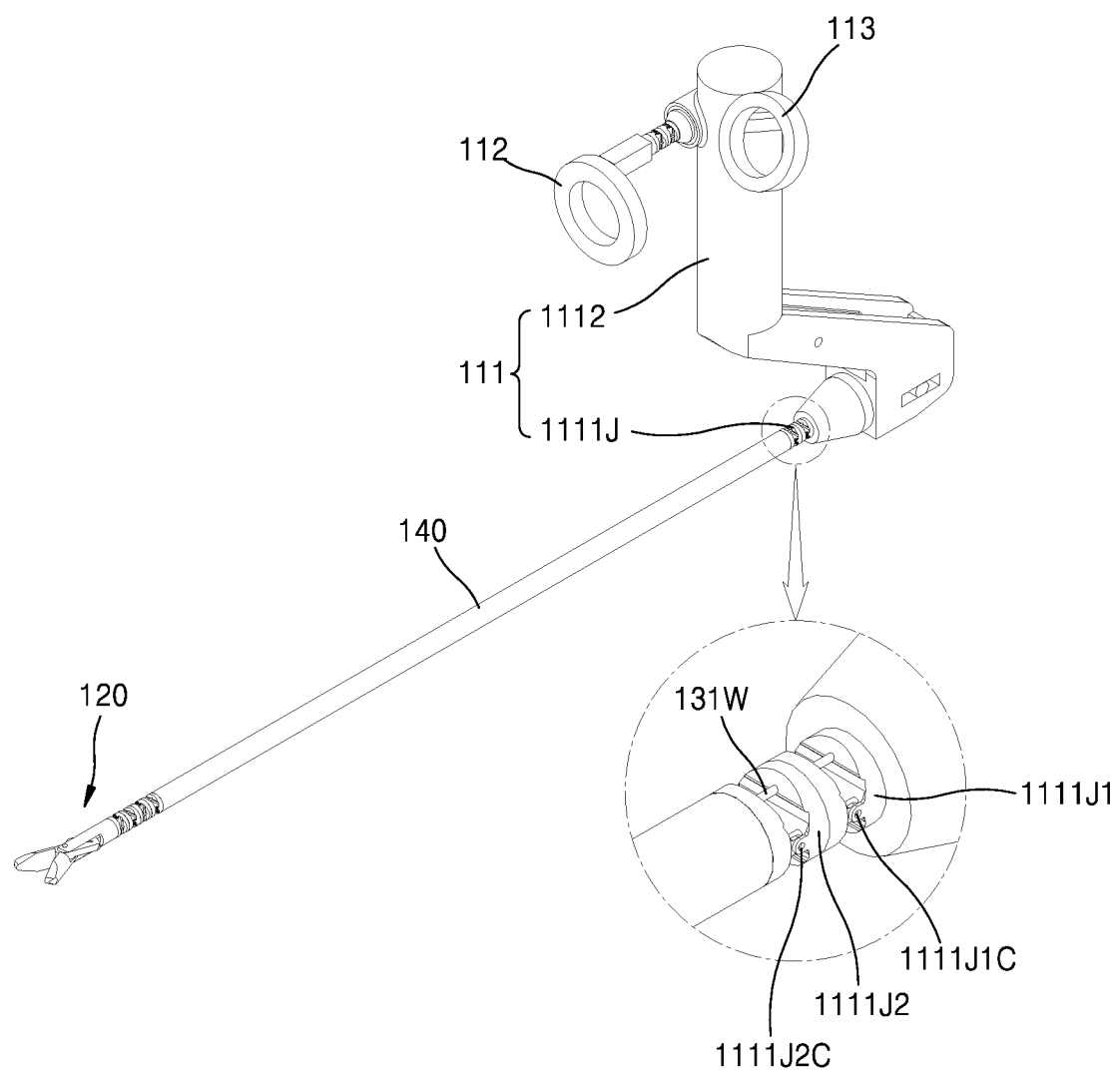
FIG. 40 is a diagram showing a second modified example of a pitch driving joint of the surgical instrument of FIG. 2, etc.

FIG. 40 is a diagram showing a second modified example of a pitch operating joint (see 1111 of FIG. 2) of the surgical instrument of FIG. 2, etc. (node type—J).

Referring to FIG. 40, the second modified example of the pitch operating joint in the surgical instrument uses a node type joint member as a pitch operating joint 1111J of the manipulator 110. That is, in the manipulator (see 110 of FIG. 2) of the surgical instrument illustrated in FIGS. 2 and 3, the pitch operating joint (see 1111 of FIG. 2) for performing the pitch operation of the manipulator is configured by using the curved type joint member, whereas the pitch operating joint 1111J for performing the pitch operation is configured by using a node type joint member according to the present modified example.

In detail, the pitch operating joint 1111J includes first and second pitch nodes 1111J1 and 111112 performing as pitch operating joints. Here, the first pitch node 1111J1 and the second pitch node 111112 are formed to be rotatable about the axes of each other to perform the pitch operation.

Here, the first pitch node 1111J1 includes a pitch connector 1111J1C that protrudes from a diameter of the first pitch node 1111J1 in the Y-axis direction towards the end tool 120 to be connected to neighboring joints, and the second pitch node 111112 includes a pitch connector 1111J2C that protrudes from a diameter of the second pitch node 111112 in the Y-axis direction towards the end tool 120 to be connected to the neighboring joints.

Here, the first and second pitch nodes 1111J1 and 111112 are formed to connect the connection unit 140 to the pitch operating joint 1111J, and thus, when the pitch operating grip 1112 is rotated, the first pitch node 1111J1 and the end tool 120 connected to the first pitch node 1111J1 are rotated about the Y-axis direction. Here, rotation amounts of the first pitch node 1111J1 and the second pitch node 111112 are summed up to a total rotation amount of the pitch operating joint 1111J.

That is, the pitch nodes 1111J1 and 111112 of the pitch operating joint 1111J are formed to be rotatable about the Y-axis, and may be a rotating center of the pitch movement.

Here, since the actuation wire (not shown) passes through the centers of the two pitch wires 131W that are in parallel with each other and the centers of the two yaw wires 132W that are in parallel with each other, and is not affected by the pitch movement and the yaw movement.

Modified Examples of a Yaw Operator in the Surgical Instrument

As shown in FIG. 2, the yaw operator according to the present invention is characterized in view of rotating about the Z-axis to perform operations of pulling or pushing the yaw wires connected to opposite sides thereof. There may be a plurality of detailed structures capable of implementing the above characteristics, and modified examples thereof will be described in detail below. The modified examples that will be described below are some of various modified examples capable of implementing the above-described characteristics, and although not described herein, various examples capable of implementing the characteristics may be provided, and these examples are appreciated to be included in the scope of the present invention.

Figure 41:
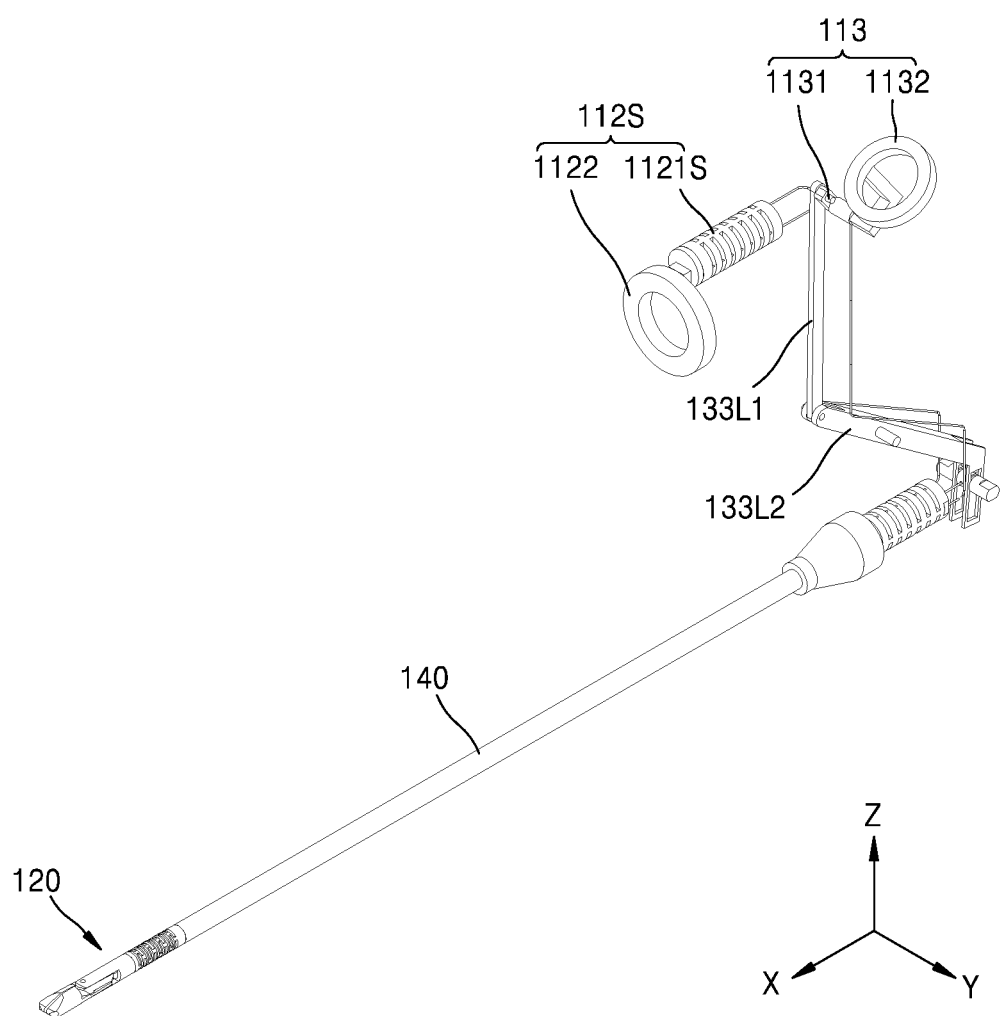
FIG. 41 is a diagram showing a first modified example of a yaw operator of the surgical instrument of FIG. 2, etc.

FIG. 41 is a diagram showing a first modified example of a yaw operator (see 112 of FIG. 2) of the surgical instrument of FIG. 2, etc. (curved type—S).

Referring to FIG. 41, the first modified example of the yaw operator in the surgical instrument uses a curved type joint member as a yaw operator 1121S of the manipulator 110. That is, in the manipulator (see 110 of FIG. 4) of the surgical instrument illustrated in FIGS. 2 and 4, the yaw operator (see 112 of FIG. 4) is configured to perform the yaw operation of the manipulator by using the yaw rotating axis (see 1121 of FIG. 4) and the pulley (see 1121a of FIG. 4), whereas the yaw operator 112S is configured to perform the yaw operation by using the curved type joint member in the present modified example.

In detail, the yaw operator 112S includes a yaw joint member 1121S of a curved type joint member for performing as a yaw rotating joint, and a yaw rotating member 1122 formed at an end portion of the yaw joint member 1121S. Here, the yaw joint member 1121S is formed to be rotatable about the Z-axis to perform the yaw operation, and may be a rotating center of the yaw movement.

Figure 42:
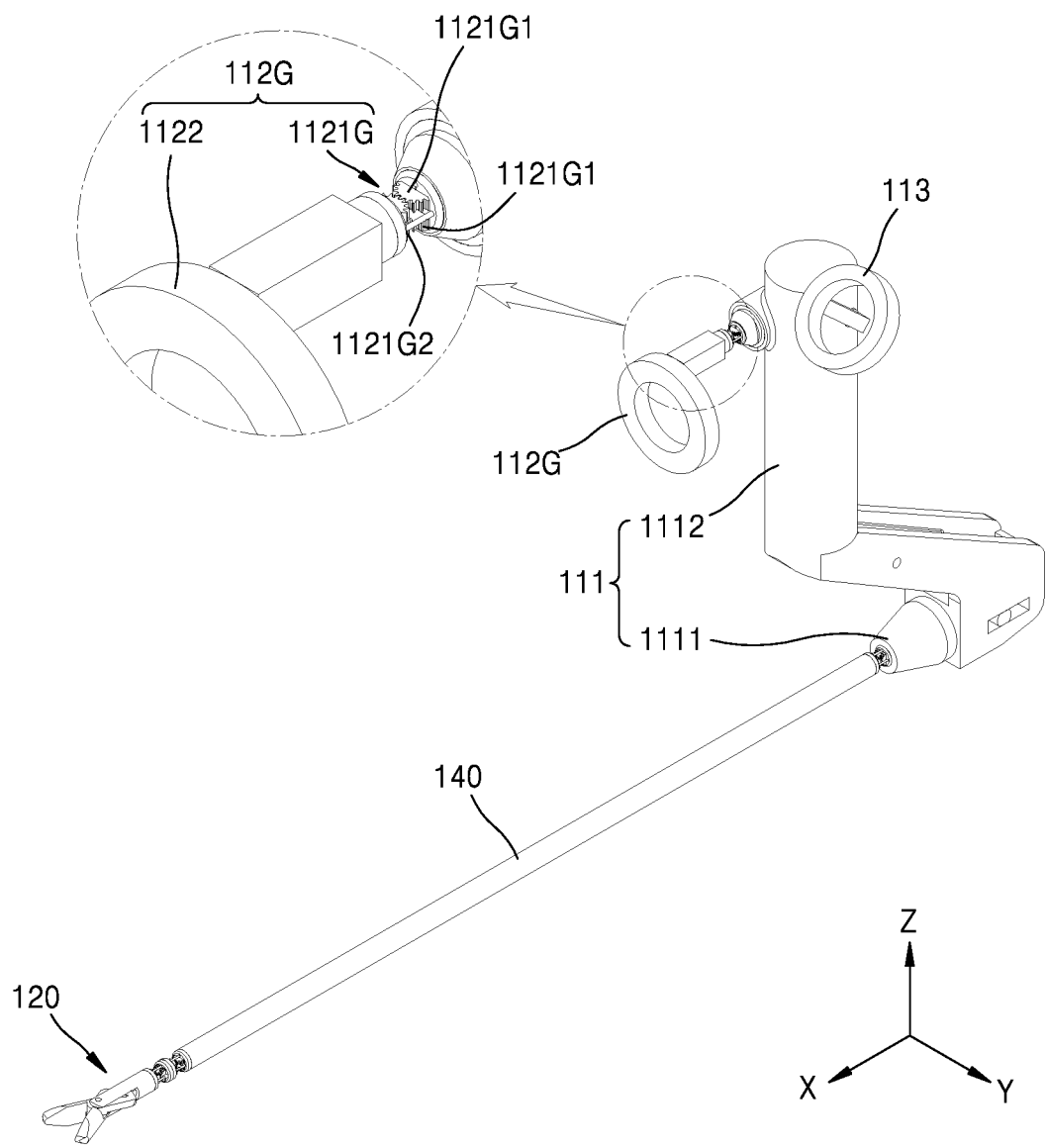
FIG. 42 is a diagram showing a second modified example of a yaw operator of the surgical instrument of FIG. 2, etc.

FIG. 42 is a diagram showing a second modified example of a yaw operator (see 112 of FIG. 2) of the surgical instrument of FIG. 2, etc. (gear type-G).

Referring to FIG. 42, the second modified example of the yaw operator in the surgical instrument uses a gear type joint member as a yaw operator 112G of the manipulator 110. That is, in the manipulator (see 110 of FIG. 4) of the surgical instrument illustrated in FIGS. 2 and 4, the yaw operator (see 112 of FIG. 4) is configured to perform the yaw operation of the manipulator by using the yaw rotating axis (see 1121 of FIG. 4) and the pulley (see 1121a of FIG. 4), whereas the yaw operator 112G is configured to perform the yaw operation by using the gear type joint member in the present modified example.

In detail, the yaw operator 112G includes a yaw joint member 1121G of a gear type joint member for performing as a yaw rotating joint, and a yaw rotating member 1122 formed at an end portion of the yaw joint member 1121G.

In detail, the yaw operator 112G includes first and second yaw gears 1121G1 and 1121G2 for performing as yaw rotating joints. Here, the second yaw gear 1121G2 is formed to be rotatable about the Z-axis to perform the yaw operation.

Here, the first yaw gear 1121G1 is fixedly formed on an end portion of the pitch operating grip 1112 and the second yaw gear 1121G2 is fixedly formed on an end portion of the yaw rotating member 1122, and thus, when the yaw rotating member 1122 is rotated, the second yaw gear 1121G21 is rotated about an axis of the first yaw gear 1121G1 along with the first yaw gear 1121G1. That is, the yaw operator 112G is formed to be rotatable about the Z-axis to perform the yaw movement.

Figure 43:
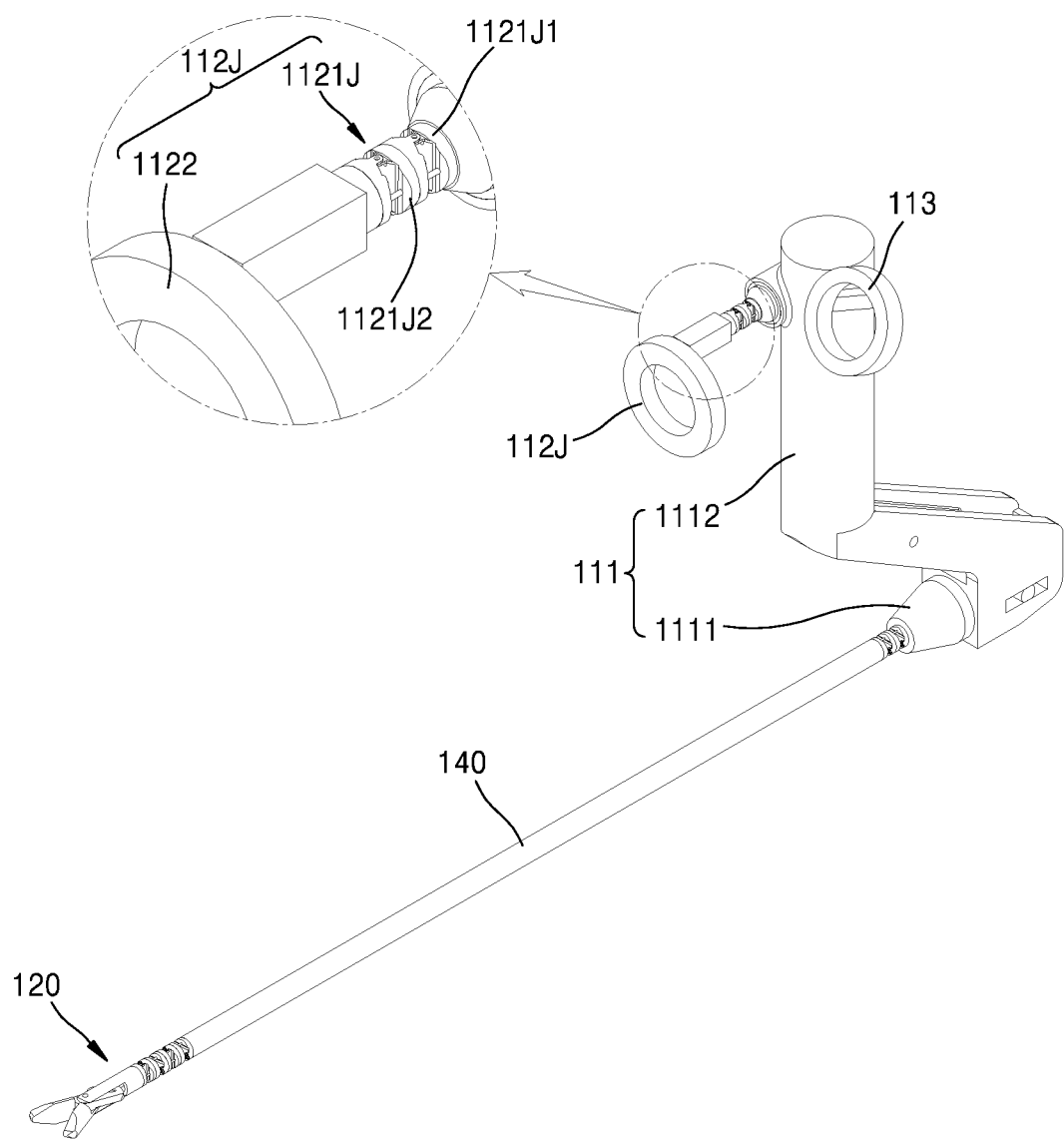
FIG. 43 is a diagram showing a third modified example of a yaw operator of the surgical instrument of FIG. 2, etc.

FIG. 43 is a diagram showing a third modified example of a yaw operator (see 112 of FIG. 2) of the surgical instrument of FIG. 2, etc. (node type—J).

Referring to FIG. 43, the third modified example of the yaw operator in the surgical instrument uses a node type joint member as a yaw operator 112J of the manipulator 110. That is, in the manipulator (see 110 of FIG. 4) of the surgical instrument illustrated in FIGS. 2 and 4, the yaw operator (see 112 of FIG. 4) is configured to perform the yaw operation of the manipulator by using the yaw rotating axis (see 1121 of FIG. 4) and the pulley (see 1121a of FIG. 4), whereas the yaw operator 112J is configured to perform the yaw operation by using the curved type joint member in the present modified example.

In detail, the yaw operator 112J includes a yaw joint member 1121J of a node type joint member for performing as a yaw rotating joint, and a yaw rotating member 1122 formed at an end portion of the yaw joint member 1121J.

In detail, the yaw operator 112J includes first and second yaw nodes 1121J1 and 112112 for performing as yaw rotating joints. Here, the first yaw node 1121J1 and the second yaw node 1121J2 are formed to be rotatable about the Z-axis to perform the yaw operation. Here, rotation amounts of the first yaw node 1121J1 and the second yaw node 112112 are summed up to a total rotation amount of the yaw operating joint 1121J.

Here, the first yaw node 1121J1 is formed on an end portion of the pitch operating grip 1112 and the second yaw node 112112 is formed on an end portion of the yaw rotating member 1122, and thus, when the yaw rotating member 1122 is rotated, the first and second yaw nodes 1121J1 and 112112 are rotated about the Z-axis to push a side of the yaw wires (not shown) and pull the opposite side of the yaw wires. That is, the yaw operator 112J is formed to be rotatable about the Z-axis to perform the yaw movement.

Modified Examples of Pitch/Yaw Nodes in the Surgical Instrument

As shown in FIG. 19A, the pitch/yaw nodes of the present invention are characterized in that the pitch and yaw wires are located at four directions and the actuation wire is centered so that the pitch and yaw operations do not affect the other operations when the pitch/yaw nodes perform the pitch and yaw operations, and the actuation operation by the actuation operator does not affect the other operations. There may be a plurality of detailed structures capable of implementing the above characteristics, and modified examples thereof will be described in detail below. The modified examples that will be described below are some of various modified examples capable of implementing the above-described characteristics, and although not described herein, various examples capable of implementing the characteristics may be provided, and these examples are appreciated to be included in the scope of the present invention.

Figure 44:
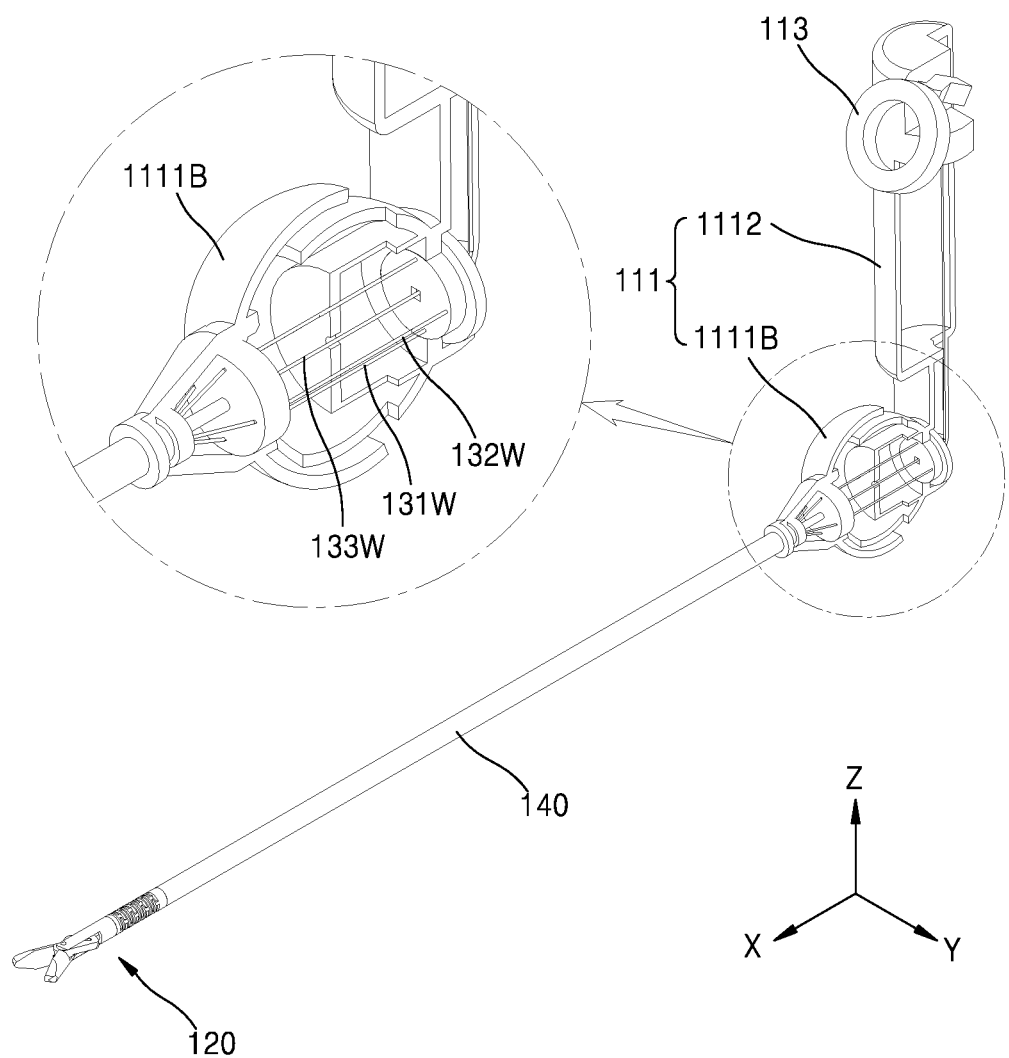
FIG. 44 is a diagram showing a first modified example of a pitch/yaw driving joint of the surgical instrument of FIG. 19A, etc. (ball joint—B)

FIG. 44 is a diagram showing a first modified example of a pitch/yaw rotating joint (see 5111 of FIG. 19A) of the surgical instrument of FIG. 19A, etc. (ball joint—B).

Referring to FIG. 44, the first modified example of the pitch/yaw rotating joint in the surgical instrument uses a ball joint as a pitch/yaw rotating joint 1111B of the manipulator 110. That is, in the manipulator (see 510 of FIG. 19A) of the surgical instrument illustrated in FIG. 19A, the pitch/yaw rotating joint (see 5111 of FIG. 19A) for performing the pitch/yaw operation of the manipulator is configured by using the curved type joint member, whereas the pitch/yaw rotating joint 1111B for performing the pitch and yaw operations is configured by using a ball joint according to the present modified example. Here, the ball joint is well known in the art, and thus, detailed descriptions thereof are omitted in the present specification.

The pitch/yaw rotating joint 1111B is rotated in an up-and-down direction about the Y-axis and may be a rotating center of the pitch movement. In addition, the pitch/yaw rotating joint 1111B is rotated in a left-and-right direction about the Z-axis and may be a rotating center of the yaw movement.

In addition, opposite end portions of the pitch wires 131W and the yaw wires 132W are respectively coupled to an end portion in the pitch/yaw rotating joint 1111B. Therefore, when the pitch/yaw operating grip 1112 is rotated, the pitch/yaw rotating joint 1111B connected to the pitch/yaw operating grip 1112 is rotated, and as the pitch/yaw rotating joint 1111B is rotated, one end portions of the pitch wires 131W or the yaw wires 132W are pushed and the other end portions are pulled so as to perform the pitch movement or the yaw movement of the end tool 120 connected to the pitch wires 131W or the yaw wires 132W.

Figure 45:
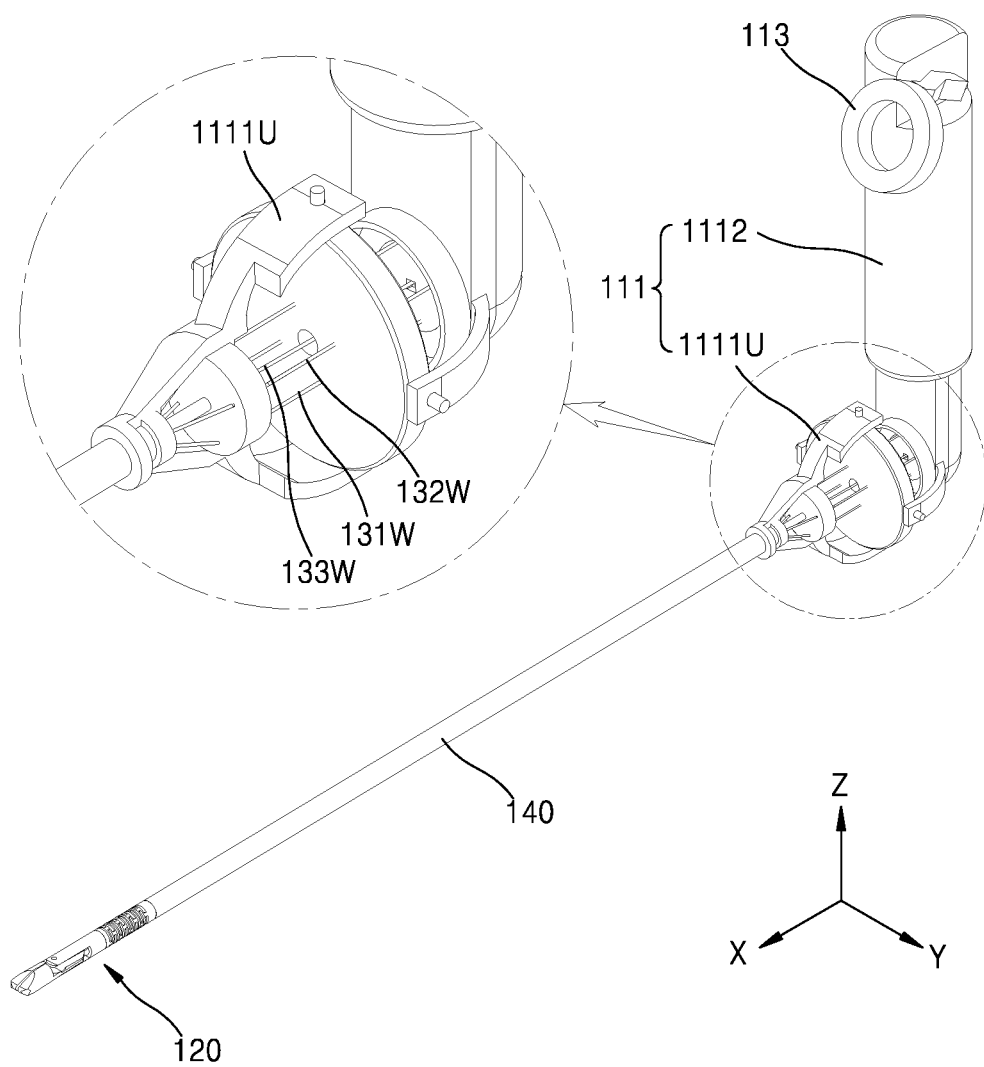
FIG. 45 is a diagram showing a second modified example of a pitch/yaw driving joint of the surgical instrument of FIG. 19A, etc. (universal joint—U)

FIG. 45 is a diagram showing a second modified example of a pitch/yaw rotating joint (see 5111 of FIG. 19A) of the surgical instrument of FIG. 19A, etc. (universal joint—U).

Referring to FIG. 45, the second modified example of the pitch/yaw rotating joint in the surgical instrument uses a universal joint as a pitch/yaw rotating joint 1111U of the manipulator 110. That is, in the manipulator (see 510 of FIG. 19A) of the surgical instrument illustrated in FIG. 19A, the pitch/yaw rotating joint (see 5111 of FIG. 19A) for performing the pitch/yaw operation of the manipulator is configured by using the curved type joint member, whereas the pitch/yaw rotating joint 1111U for performing the pitch and yaw operations is configured by using a universal joint according to the present modified example. Here, the universal joint is well known in the art, and thus, detailed descriptions thereof are omitted in the present specification.

The pitch/yaw rotating joint 1111U is rotated in an up-and-down direction about the Y-axis and may be a rotating center of the pitch movement. In addition, the pitch/yaw rotating joint 1111U is rotated in a left-and-right direction about the Z-axis and may be a rotating center of the yaw movement.

In addition, opposite end portions of the pitch wires 131W and the yaw wires 132W are respectively coupled to an end portion in the pitch/yaw rotating joint 1111U. Therefore, when the pitch/yaw operating grip 1112 is rotated, the pitch/yaw rotating joint 1111U connected to the pitch/yaw operating grip 1112 is rotated, and as the pitch/yaw rotating joint 1111U is rotated, one end portions of the pitch wires 131W or the yaw wires 132W are pushed and the other end portions are pulled so as to perform the pitch movement or the yaw movement of the end tool 120 connected to the pitch wires 131W or the yaw wires 132W.

Figure 46:
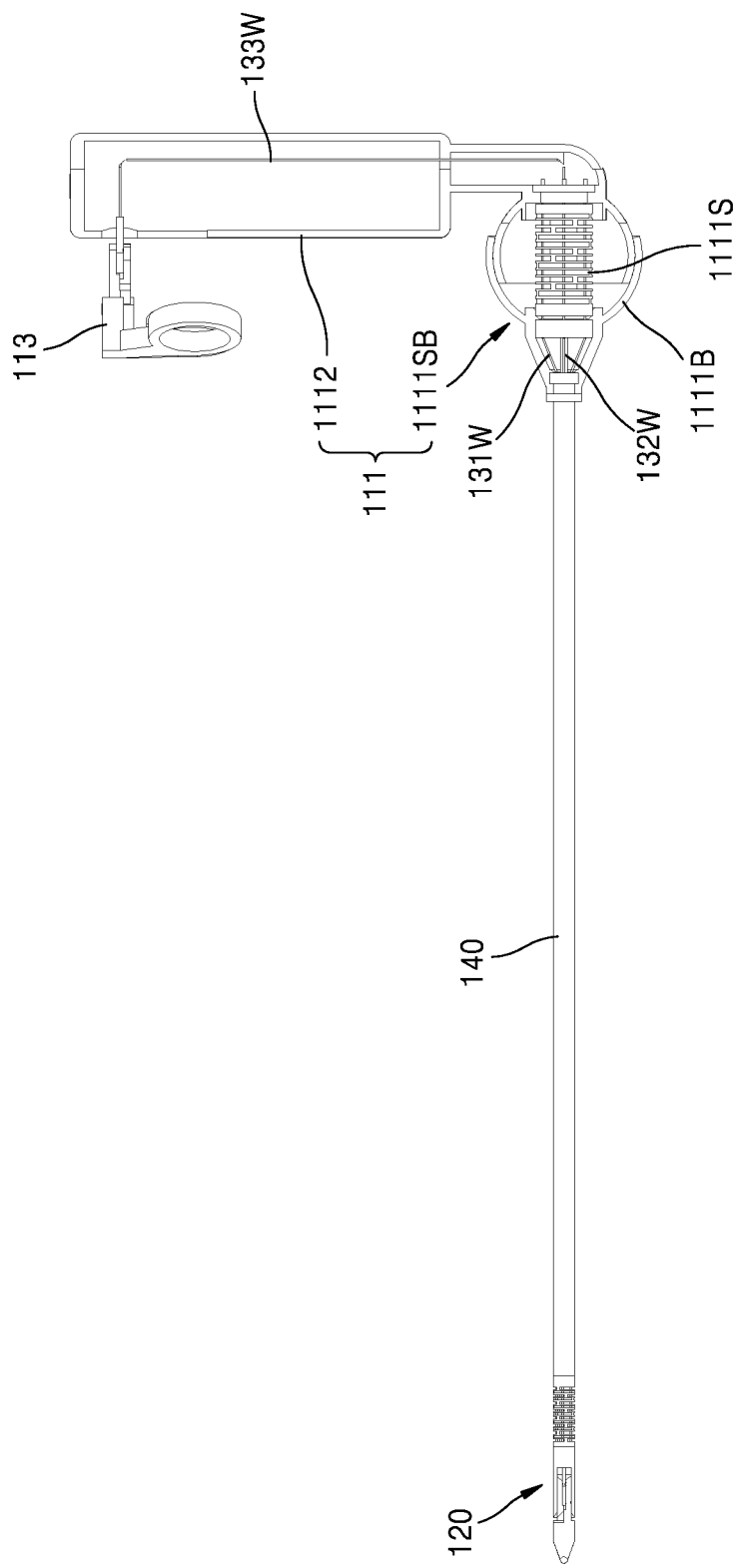
FIG. 46 is a diagram showing a third modified example of a pitch/yaw driving joint of the surgical instrument of FIG. 19A, etc. (SB)

FIG. 46 is a diagram showing a third modified example of a pitch/yaw rotating joint (see 5111 of FIG. 19A) of the surgical instrument of FIG. 19A, etc. (SB).

Referring to FIG. 46, the third modified example of the pitch/yaw rotating joint in the surgical instrument uses a combination type joint of a curved type joint member and a ball joint as a pitch/yaw rotating joint 1111SB of the manipulator 110. That is, in the manipulator (see 510 of FIG. 19A) of the surgical instrument illustrated in FIG. 19A, the pitch/yaw rotating joint (see 5111 of FIG. 19A) for performing the pitch/yaw operation of the manipulator is configured by using the curved type joint member, whereas the pitch/yaw rotating joint 1111SB for performing the pitch and yaw operations is configured by using the curved type joint member 1111S and the ball joint 1111B together according to the present modified example.

The pitch/yaw rotating joint 1111SB is rotated in an up-and-down direction about the Y-axis and may be a rotating center of the pitch movement. In addition, the pitch/yaw rotating joint 1111SB is rotated in a left-and-right direction about the Z-axis and may be a rotating center of the yaw movement.

In addition, opposite end portions of the pitch wires 131W and the yaw wires 132W are respectively coupled to an end portion in the pitch/yaw rotating joint 1111SB. Therefore, when the pitch/yaw operating grip 1112 is rotated, the pitch/yaw rotating joint 1111SB connected to the pitch/yaw operating grip 1112 is rotated, and as the pitch/yaw rotating joint 1111SB is rotated, one end portions of the pitch wires 131W or the yaw wires 132W are pushed and the other end portions are pulled so as to perform the pitch movement or the yaw movement of the end tool 120 connected to the pitch wires 131W or the yaw wires 132W.

Here, since the actuation wire (not shown) passes through the centers of the two pitch wires 131W that are in parallel with each other and the centers of the two yaw wires 132W that are in parallel with each other, and is not affected by the pitch movement and the yaw movement.

Figure 47:
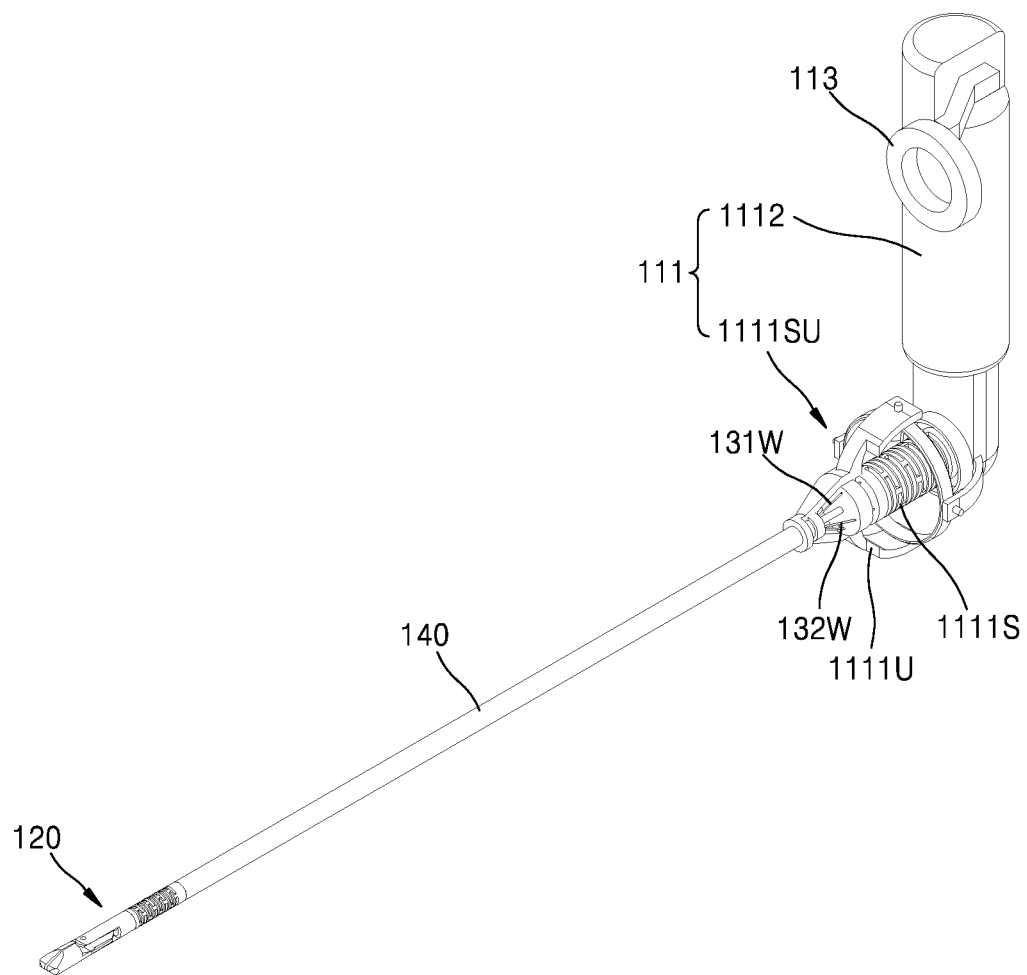
FIG. 47 is a diagram showing a fourth modified example of a pitch/yaw driving joint of the surgical instrument of FIG. 19A, etc. (SU)

FIG. 47 is a diagram showing a fourth modified example of a pitch/yaw rotating joint (see 5111 of FIG. 19A) of the surgical instrument of FIG. 19A, etc. (SU).

Referring to FIG. 47, the fourth modified example of the pitch/yaw rotating joint in the surgical instrument uses a combination type joint of a curved type joint member and a universal joint as a pitch/yaw rotating joint 1111SU of the manipulator 110. That is, in the manipulator (see 510 of FIG. 19A) of the surgical instrument illustrated in FIG. 19A, the pitch/yaw rotating joint (see 5111 of FIG. 19A) for performing the pitch/yaw operation of the manipulator is configured by using the curved type joint member, whereas the pitch/yaw rotating joint 1111SU for performing the pitch and yaw operations is configured by using the curved type joint member 1111S and the universal joint 1111U together according to the present modified example.

The pitch/yaw rotating joint 1111SU is rotated in an up-and-down direction about the Y-axis and may be a rotating center of the pitch movement. In addition, the pitch/yaw rotating joint 1111SU is rotated in a left-and-right direction about the Z-axis and may be a rotating center of the yaw movement.

In addition, opposite end portions of the pitch wires 131W and the yaw wires 132W are respectively coupled to an end portion in the pitch/yaw rotating joint 1111SU. Therefore, when the pitch/yaw operating grip 1112 is rotated, the pitch/yaw rotating joint 1111SU connected to the pitch/yaw operating grip 1112 is rotated, and as the pitch/yaw rotating joint 1111SU is rotated, one end portions of the pitch wires 131W or the yaw wires 132W are pushed and the other end portions are pulled so as to perform the pitch movement or the yaw movement of the end tool 120 connected to the pitch wires 131W or the yaw wires 132W.

Figure 48:
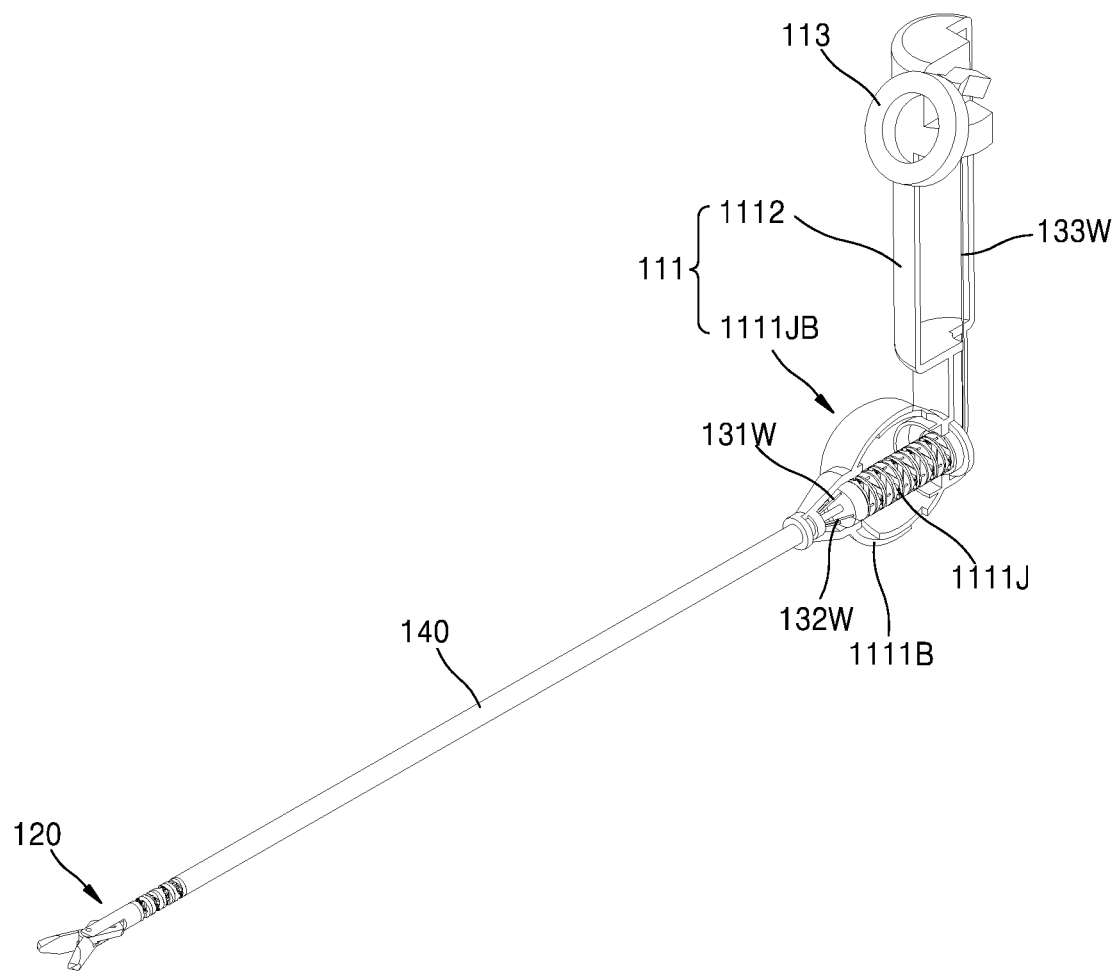
FIG. 48 is a diagram showing a fifth modified example of a pitch/yaw driving joint of the surgical instrument of FIG. 19A, etc. (JB)

FIG. 48 is a diagram showing a fifth modified example of a pitch/yaw rotating joint (see 5111 of FIG. 19A) of the surgical instrument of FIG. 19A, etc. (JB).

Referring to FIG. 48, the fifth modified example of the pitch/yaw rotating joint in the surgical instrument uses a combination type joint of a node type joint member and a ball joint as a pitch/yaw rotating joint 1111JB of the manipulator 110. That is, in the manipulator (see 510 of FIG. 19A) of the surgical instrument illustrated in FIG. 19A, the pitch/yaw rotating joint (see 5111 of FIG. 19A) for performing the pitch/yaw operation of the manipulator is configured by using the curved type joint member, whereas the pitch/yaw rotating joint 1111JB for performing the pitch and yaw operations is configured by using the node type joint member 1111J and the ball joint 1111B together according to the present modified example.

The pitch/yaw rotating joint 1111JB is rotated in an up-and-down direction about the Y-axis and may be a rotating center of the pitch movement. In addition, the pitch/yaw rotating joint 1111JB is rotated in a left-and-right direction about the Z-axis and may be a rotating center of the yaw movement.

In addition, opposite end portions of the pitch wires 131W and the yaw wires 132W are respectively coupled to an end portion in the pitch/yaw rotating joint 1111JB. Therefore, when the pitch/yaw operating grip 1112 is rotated, the pitch/yaw rotating joint 1111JB connected to the pitch/yaw operating grip 1112 is rotated, and as the pitch/yaw rotating joint 1111JB is rotated, one end portions of the pitch wires 131W or the yaw wires 132W are pushed and the other end portions are pulled so as to perform the pitch movement or the yaw movement of the end tool 120 connected to the pitch wires 131W or the yaw wires 132W.

Figure 49:
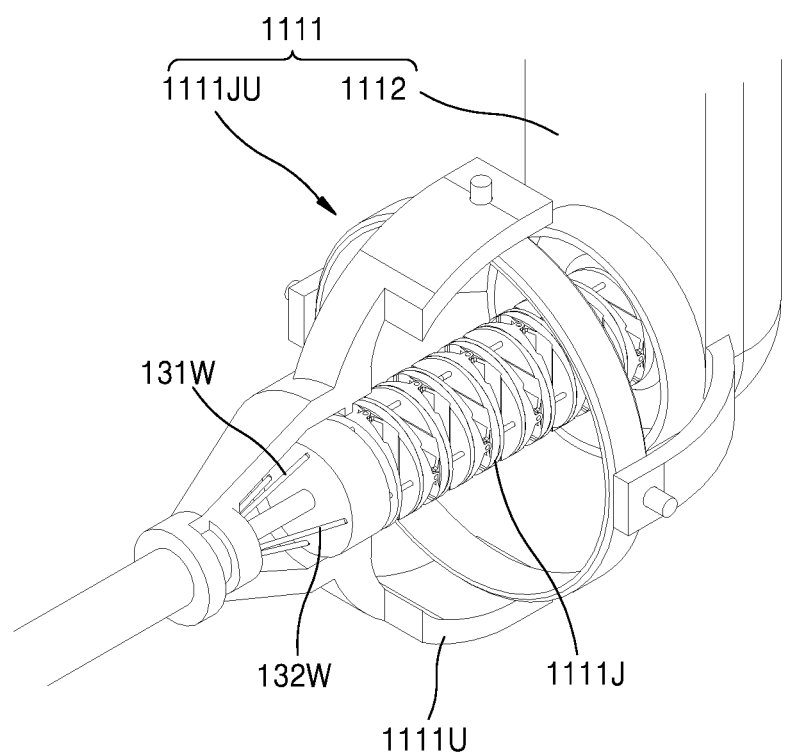
FIG. 49 is a diagram showing a sixth modified example of a pitch/yaw driving joint of the surgical instrument of FIG. 19A, etc. (JU)

FIG. 49 is a diagram showing a sixth modified example of a pitch/yaw rotating joint (see 5111 of FIG. 19A) of the surgical instrument of FIG. 19A, etc. (JU).

Referring to FIG. 49, the sixth modified example of the pitch/yaw rotating joint in the surgical instrument uses a combination type joint of a node type joint member and a universal joint as a pitch/yaw rotating joint 1111JU of the manipulator 110. That is, in the manipulator (see 510 of FIG. 19A) of the surgical instrument illustrated in FIG. 19A, the pitch/yaw rotating joint (see 5111 of FIG. 19A) for performing the pitch/yaw operation of the manipulator is configured by using the curved type joint member, whereas the pitch/yaw rotating joint 1111JU for performing the pitch and yaw operations is configured by using the node type joint member 1111J and the universal joint 1111U together according to the present modified example.

The pitch/yaw rotating joint 1111JU is rotated in an up-and-down direction about the Y-axis and may be a rotating center of the pitch movement. In addition, the pitch/yaw rotating joint 1111JU is rotated in a left-and-right direction about the Z-axis and may be a rotating center of the yaw movement.

In addition, opposite end portions of the pitch wires 131W and the yaw wires 132W are respectively coupled to an end portion in the pitch/yaw rotating joint 1111JU. Therefore, when the pitch/yaw operating grip 1112 is rotated, the pitch/yaw rotating joint 1111JU connected to the pitch/yaw operating grip 1112 is rotated, and as the pitch/yaw rotating joint 1111JU is rotated, one end portions of the pitch wires 131W or the yaw wires 132W are pushed and the other end portions are pulled so as to perform the pitch movement or the yaw movement of the end tool 120 connected to the pitch wires 131W or the yaw wires 132W.

Modified Example of a Roll Operation of the Surgical Instrument

Figure 50:
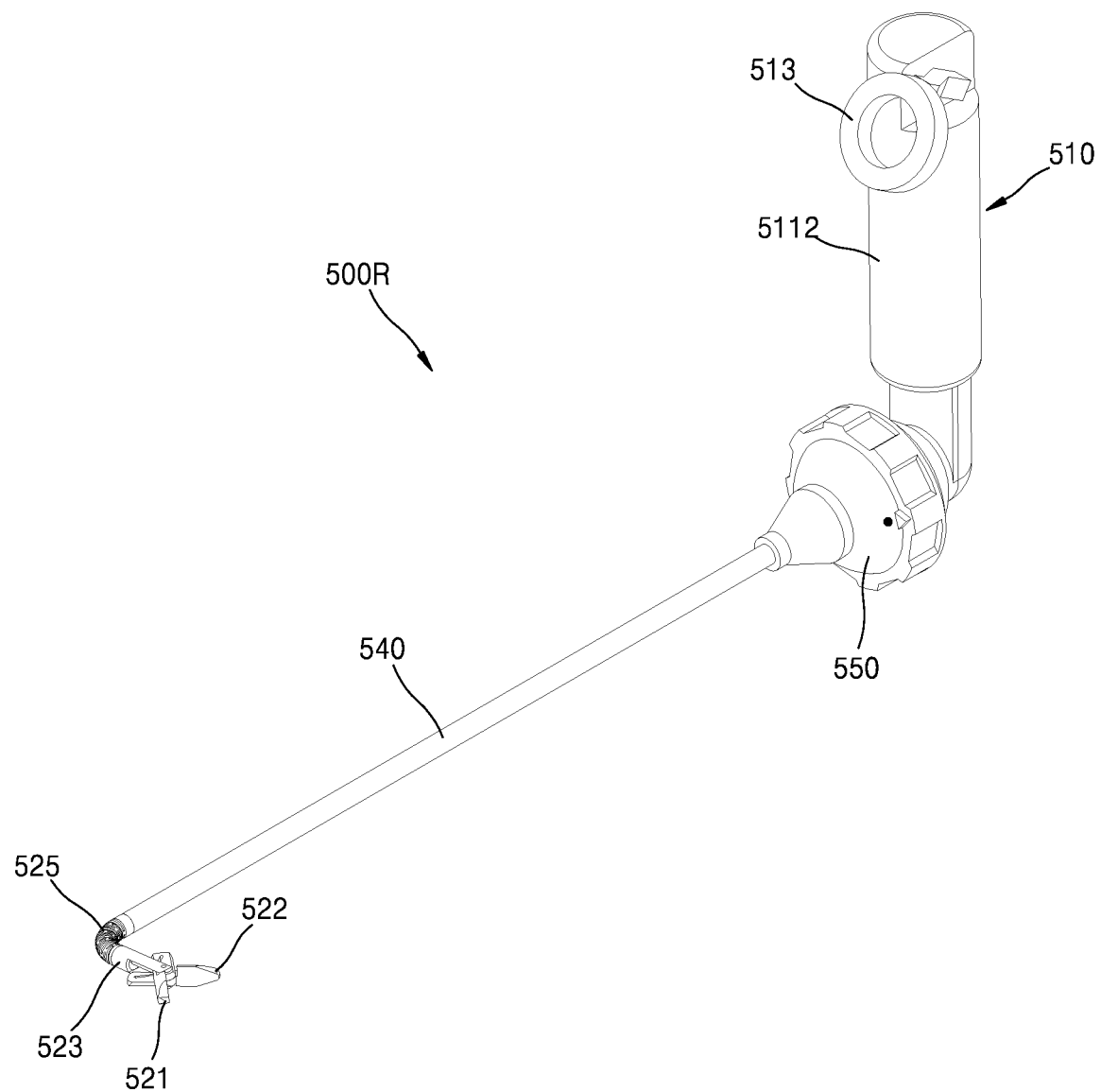
FIG. 50 is a perspective view of a surgical instrument having an additional rolling function to the surgical instrument of FIG. 19A.
Figure 51A:
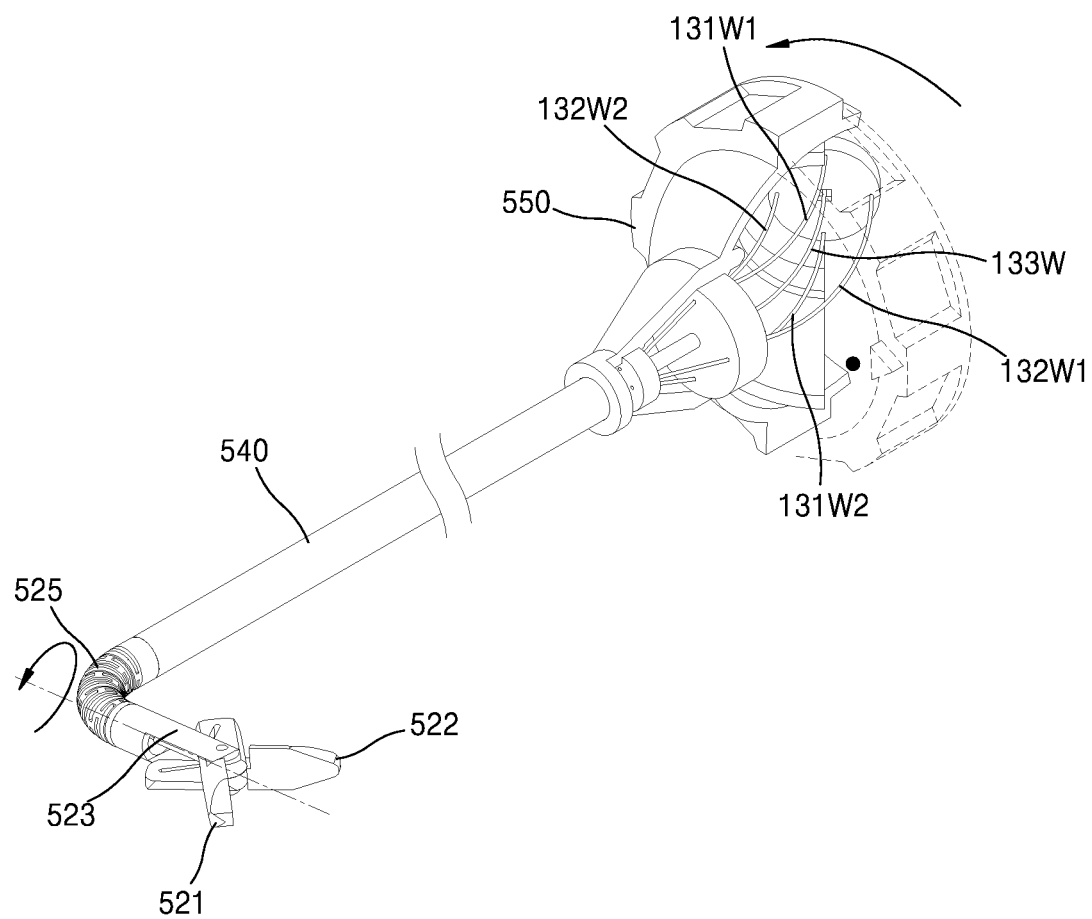
FIGS. 51A to 51E are perspective views showing the surgical instrument of FIG. 50 performing a rolling operation.
Figure 51B:
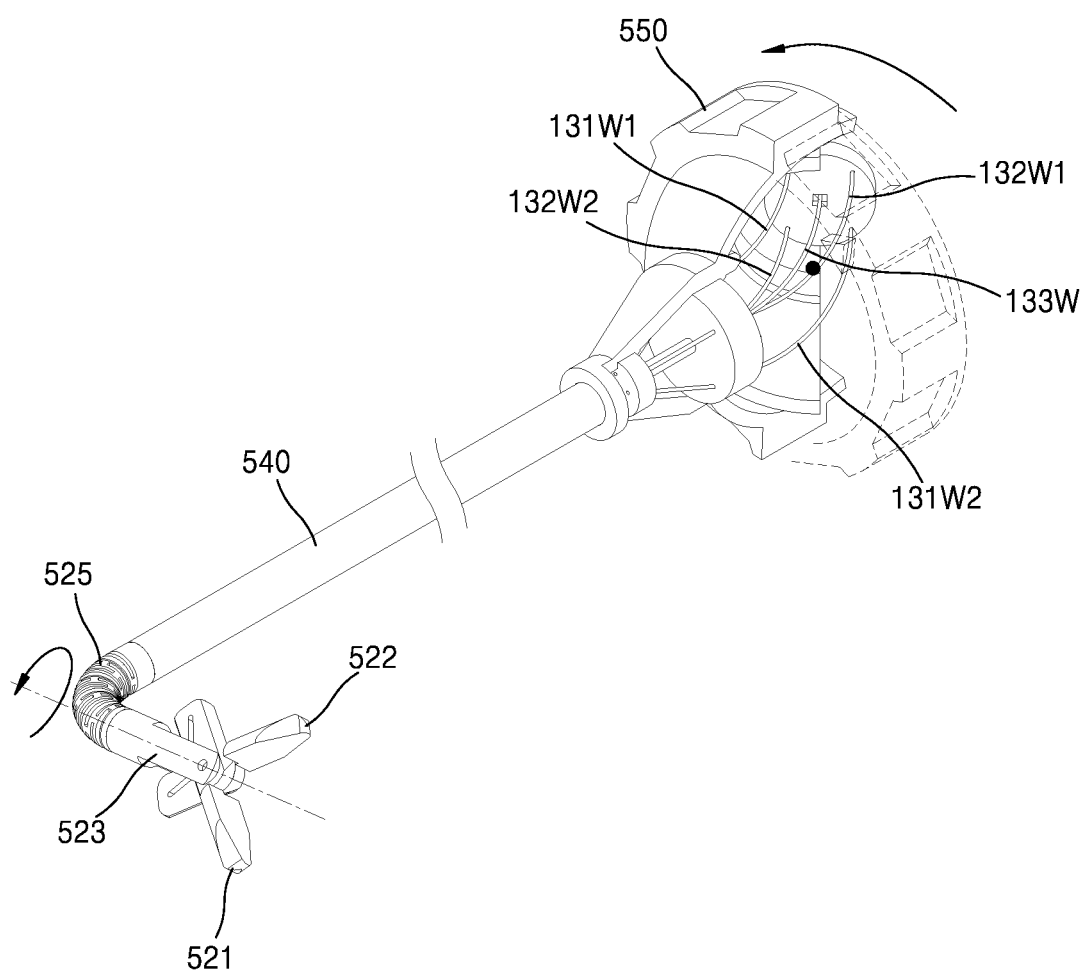
Figure 51C:
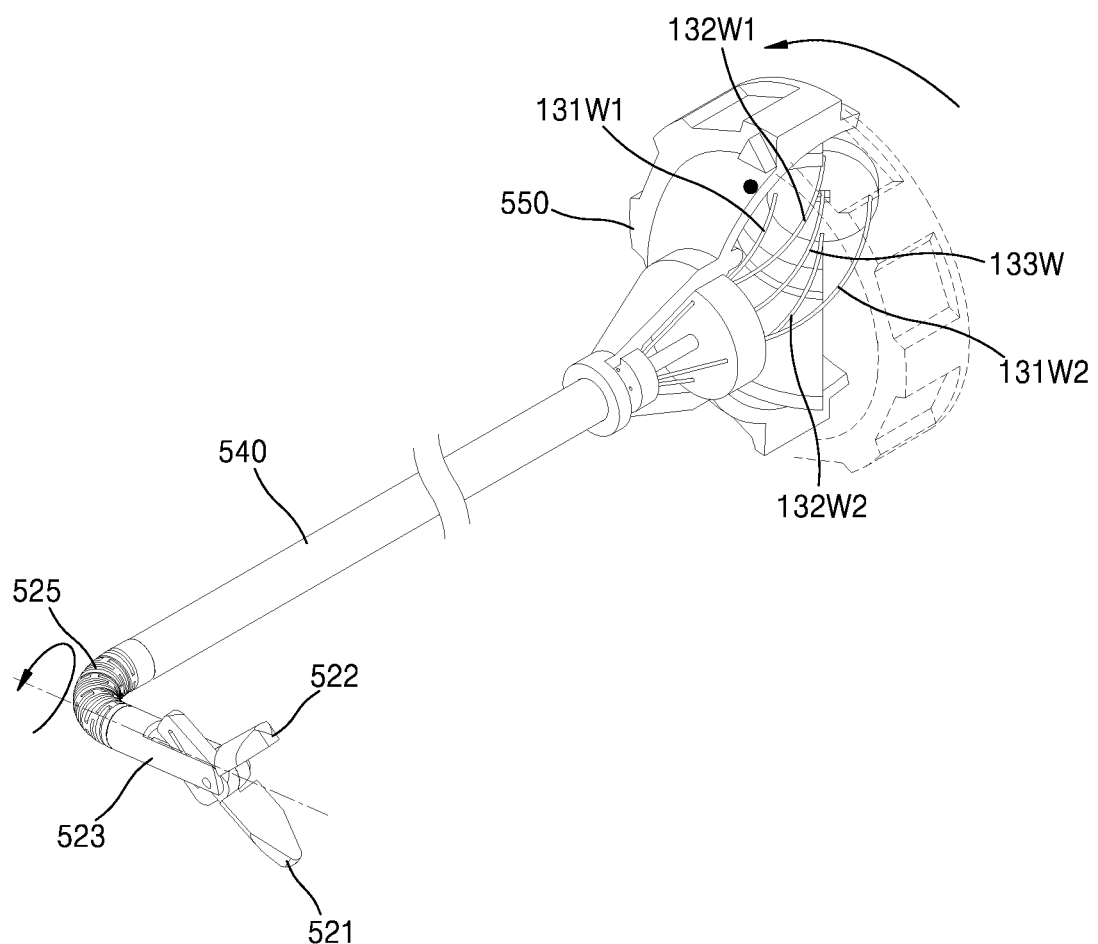
Figure 51D:
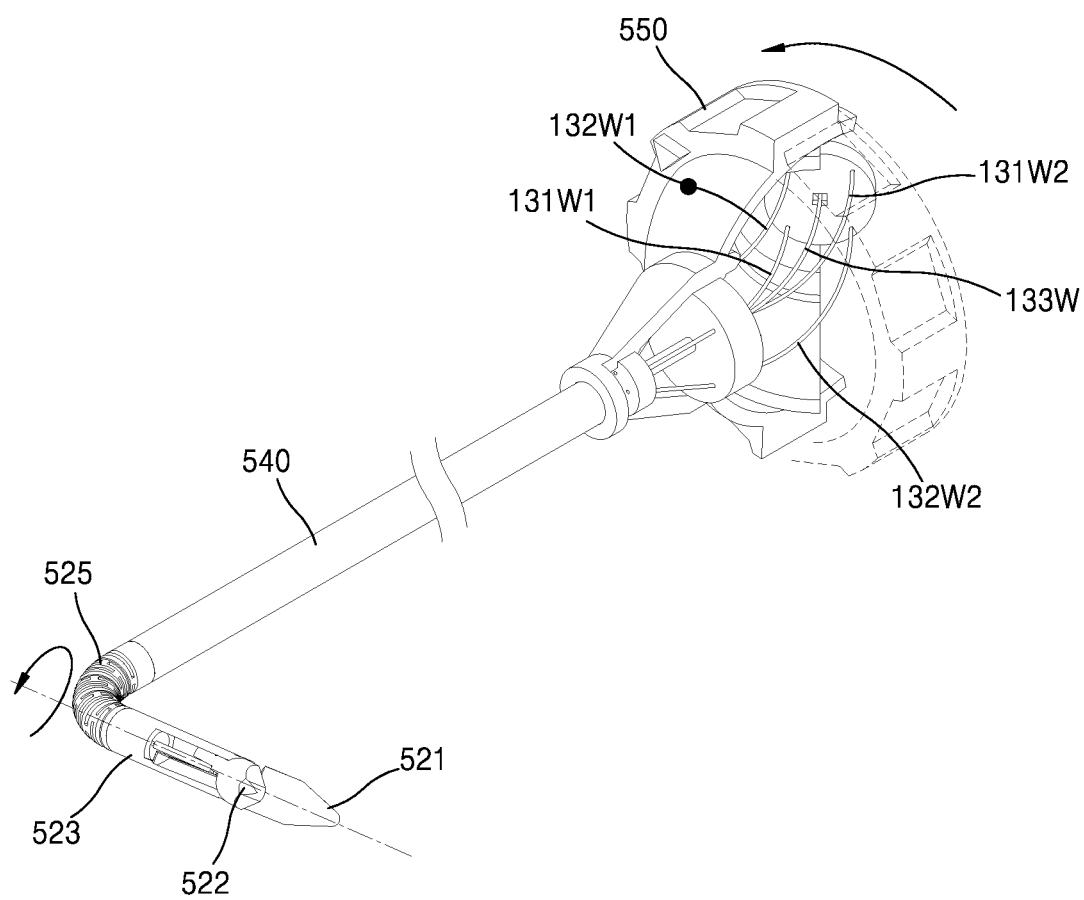
Figure 51E:
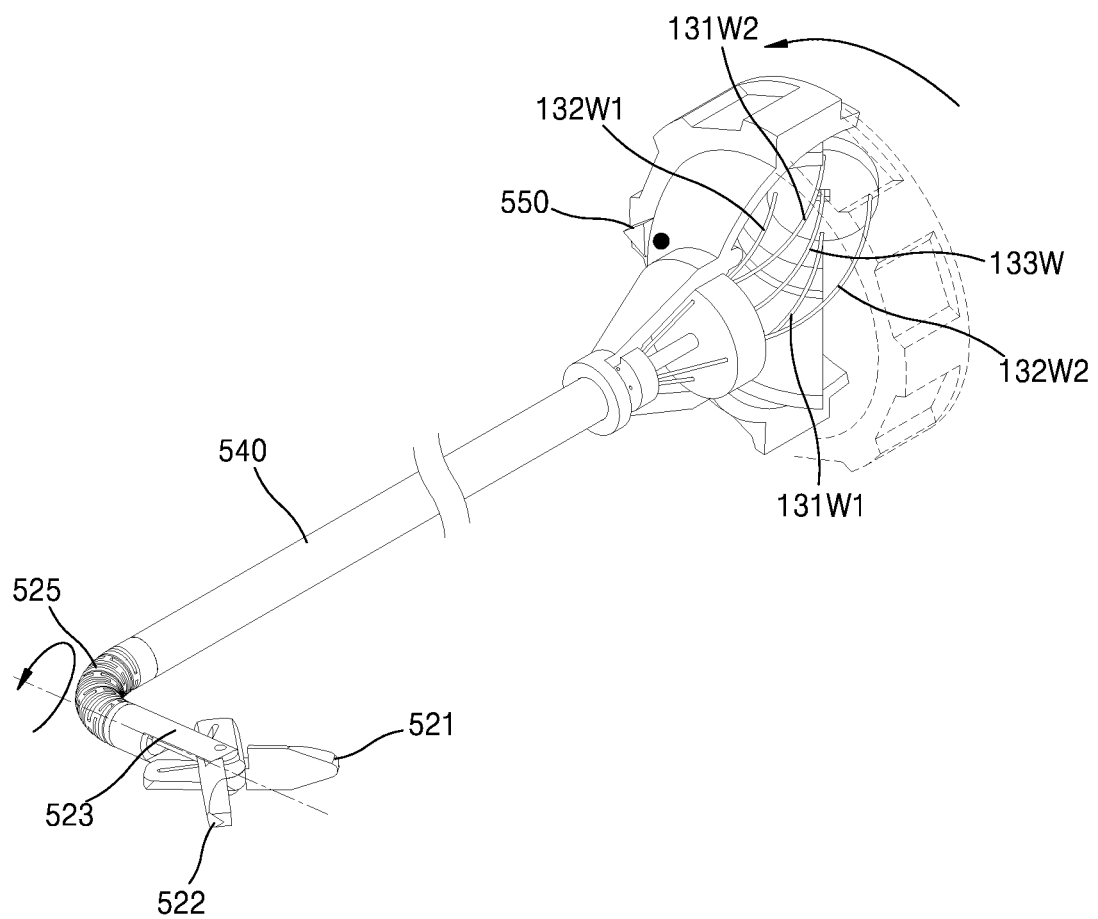

FIG. 50 is a perspective view of a surgical instrument having a rolling function in addition to the surgical instrument illustrated in FIG. 19A, etc., and FIGS. 51A to 51E are perspective views of the surgical instrument of FIG. 50 performing the rolling operation.

Referring to FIG. 50, a surgical instrument 500R according to the present modified example further includes a roll operator 550 for performing a rolling operation. That is, the surgical instrument 500R further includes the roll operator 550 formed as a ball joint surrounding the pitch/yaw rotating joint (see 5111 of FIG. 19A) of the manipulator (see 510 of FIG. 19A) in the surgical instrument illustrated in FIG. 19A, etc., so as to perform the rolling operation. Here, the rolling operation denotes an operation, in which the end tool 520 and the connection unit 540 respectively rotate about a center axis thereof in a state where a relative angle between the center axis of the connection unit and the center axis of the end tool 520 is maintained when the roll operator 550 is rotated.

That is, as shown in FIGS. 51A to 51E, when the roll operator 550 is rotated in a state where the other parts of the manipulator 510 are fixed, a curved angle of the joint member 525 is maintained, and in this state, the first and second jaws 521 and 522 connected to the joint member 525 (and the jaw base 523 connected to the first and second jaws 521 and 522) are rotated together according to the rotation of the roll operator 550. In addition, when the first and second jaws 521 and 522 are rotated, relative locations between the first and second jaws 521 and 522 are constantly maintained. That is, the jaws 521 and 522 of the end tool 520 rotate about the center axis of the jaw base 523 while maintaining an angle therebetween. This will be described below in more detail.

The end tool 520 is rotated in pitch and yaw directions according to rotations of the pitch/yaw nodes of the manipulator. That is, the pitch/yaw rotating joint of the manipulator is rotated according to the rotation of the manipulator in the pitch direction and the yaw direction relative to the connection unit, and accordingly, the end tool 520 is also curved in the pitch direction and the yaw direction relative to the connection unit.

Here, what determines the pitch curvature angle of the end tool 520 is a relative difference between pushing and pulling of two pitch wires located at upper and lower portions on a cross-section of the pitch/yaw rotating joint in the manipulator towards the connection unit. Likewise, what determines the yaw curvature angle of the end tool 520 is a relative difference between pushing and pulling of two yaw wires located at left and right portions on a cross-section of the pitch/yaw rotating joint in the manipulator towards the connection unit.

The pitch/yaw rotating joint of the manipulator performs the curvature in the pitch direction and the yaw direction while connecting the connection unit to a grip of the manipulator, and at this time, the pitch/yaw rotating joint is configured to be rotatable by fixing the pitch/yaw rotating joint to the connection unit and not fixing an end portion of the pitch/yaw rotating joint at the manipulator side to the manipulator on the cross-section thereof, and thus, the rolling function of rotating only two jaws in a state where the end tool 520 is curved.

In more detail, when the manipulator is curved towards the yaw direction relative to the connection unit and the end tool 520 is also curved in the same direction, the pitch/yaw rotating joint of the manipulator is fixed with respect to the connection unit and a cross-sectional end at the manipulator side is not fixed with the grip of the manipulator but is rotatable, and accordingly, when a roll grip and the connection unit connected to the roll grip are rotated based on the center axis of the connection unit, the pitch/yaw rotating joint connected to the roll grip is rotated while maintaining a curved shape that is determined by the relative rotation between the connection unit and the manipulator grip. Here, four pitch and yaw wires that are located at ends of the four directions on the cross-section of the pitch/yaw rotating joint are also rotated together. As such, when the pitch/yaw rotating joint is rotated, the pitch and yaw wires located at the ends of the four directions on the pitch/yaw rotating joint are rotated together to leave original locations for other locations where there are originally the other wires.

That is, in this case, the yaw wires located at the left and right directions on the cross-section of the pitch/yaw rotating joint may be rotated to the locations of the pitch wires that are located at the upper and lower directions, and the pitch wires initially located at the upper and lower directions may be rotated to the locations of the yaw wires at the left and right directions. Therefore, when the pitch/yaw rotating joint is rotatable as described above, there is no meaning in classifying four wires as the pitch wires and the yaw wires. That is, there are four wires in four directions on the cross-section, and any wires located at the left and right directions perform as the yaw wires and any wires located at the upper and lower directions perform as the pitch wires.

Therefore, when the pitch or yaw curve is relatively determined by the connection unit and the manipulator grip even if the pitch/yaw rotating joint is rotated with the connection unit and the roll grip, the relative pitch or yaw curve between the connection unit and the end tool 520 is not affected, but is maintained. Here, two jaws of the end tool 520 are rotated about a center axis that is determined by end portions of the end tool 520 at sides of two forceps of the pitch/yaw rotating joint.

Here, the actuation wire is located to pass through a center on the cross-section of the pitch/yaw rotating joint and is not fixed with the pitch/yaw rotating joint, and thus, the actuation wire is not rotated with the rotation of the pitch/yaw rotating joint and may perform the actuation operation independently.

Here, the roll grip may be located at any position that may allow or may not interfere with the rotation of the connection unit and the pitch/yaw rotating joint of the manipulator while maintaining the relative curvature angle between the connection unit and the manipulator grip. That is, the roll grip may be fixedly located on the connection unit, may be fixedly located on the pitch/yaw rotating joint of the manipulator, or may extend from the pitch/yaw rotating joint towards the manipulator and is fixedly located on the manipulator.

In addition, various snake, joints, ball joints, etc. satisfying the above description may be used as the pitch/yaw rotating joint of the manipulator, and detailed descriptions thereof are omitted.

While the present invention has been described with reference to exemplary embodiments thereof, it will be understood by those of ordinary skill in the art that various changes in form and details may be made therein without departing from the spirit and scope of the invention. Although not described, it would be appreciated that equivalent units may be coupled to the present invention. Therefore, the scope sought to be protected of the present invention shall be defined by the appended claims.

INDUSTRIAL APPLICABILITY

The present invention may be applied to surgical instruments that may be manually operated to perform laparoscopic surgery or various surgical operations.

The invention claimed is:

1. A surgical instrument comprising:
   an end tool configured to be rotatable in at least two directions;
   a manipulator comprising a pitch operator configured to control a pitch movement of the end tool, a yaw operator configured to control a yaw movement of the end tool, and an actuation operator configured to control an actuation movement of the end tool, wherein at least one of the pitch operator and the yaw operator comprises a joint member that is capable of being bent in one or more directions;
   a power transfer assembly configured to transfer an operation of the manipulator to the end tool; and
   a connection assembly configured to extend in a first direction (X-axis), and to connect the manipulator to the end tool when the end tool is coupled to an end portion of the connection assembly and the manipulator is coupled to the other end portion of the connection assembly,
   wherein at least a part of the manipulator extends towards the end tool,
   wherein the pitch operator comprises:
   a pitch operating joint that is the joint member configured to be rotatable about a second direction (Y-axis) that is perpendicular to the first direction; and
   a pitch operating grip configured to be rotatable with the pitch operating joint by being connected to the pitch operating joint,
   wherein, in a third direction (Z-axis) that is respectively perpendicular to the first direction and the second direction,
   at least a part of the pitch operating grip is formed to be closer to the end tool than a virtual center axis of the pitch operating joint in the third direction, in at least one operating stage of the pitch operator,
   wherein the end tool comprises a first jaw and a second jaw, each formed to be rotatable, and an end tool joint member capable of being bent in one or more directions to perform a pitch operation and/or a yaw operation of the first jaw and the second jaw, and
   the manipulator is configured to control operations of the first and second jaws of the end tool,
   wherein the pitch operating joint comprises a bendable type joint member configured to be rotatable about the second direction (Y-axis) and comprising a plurality of recesses formed in an outer circumferential surface thereof along the first direction, wherein one or more ribs for guiding a bending direction of the pitch operating joint are formed in each of the plurality of recesses.

2. The surgical instrument of claim 1, wherein, when the manipulator is rotated in the two or more directions, the end tool is rotated in directions substantially identical with manipulation directions of the manipulator.

3. The surgical instrument of claim 1, wherein a direction in which the end tool is formed at the end portion of the connection assembly and a direction in which the manipulator is formed at the other end portion of the connection assembly are identical directions based on the first direction.

4. The surgical instrument of claim 1, wherein the manipulator extends away from a user who grips the surgical instrument.

5. The surgical instrument of claim 1, wherein an end portion of the manipulator is formed towards the end tool so that an end of a finger of a user gripping the manipulator faces the end tool.

6. The surgical instrument of claim 1, wherein, when the actuation operator rotates about the actuation rotating axis, the first jaw and the second jaw are rotated in opposite directions to each other.

7. The surgical instrument of claim 1, wherein the end tool joint member is a bendable type joint member that connects the end tool to the connection assembly, and comprises a plurality of recesses formed in an outer circumferential surface thereof along the first direction, wherein one or more ribs for guiding a bending direction of the end tool joint member are formed in each of the plurality of recesses.

8. The surgical instrument of claim 1, wherein the end tool joint member is a gear type joint member that connects the end tool to the connection assembly and comprises one or more pitch gears formed to be rotatable about the second direction (Y-axis) and one or more yaw gears formed to be rotatable about the third direction (Z-axis).

9. The surgical instrument of claim 1, wherein, when the pitch operator is rotated about the pitch operating joint, the end tool is rotated in an identical direction with the pitch operator based on the pitch operating joint.

10. The surgical instrument of claim 1, wherein, when the yaw operator is rotated about the yaw rotating axis, the end tool is rotated in an identical direction with the yaw operator based on the yaw rotating axis.

11. The surgical instrument of claim 1, further comprising a roll operator connected to the manipulator,
   wherein, when the roll operator is rotated, the end tool only rotates about a center axis thereof in a state where a relative angle between a center axis of the connection assembly and the center axis of the end tool is maintained.

12. The surgical instrument of claim 1, wherein the power transfer assembly comprises a pitch wire connected to the manipulator to transfer a pitch movement of the manipulator to the end tool, a yaw wire connected to the manipulator to transfer a yaw movement of the manipulator to the end tool, and an actuation wire connected to the manipulator to transfer an actuation movement of the manipulator to the end tool,
   the manipulator comprises the pitch operator configured to control a pitch movement of the end tool, the yaw operator coupled to the pitch operator and configured to control a yaw movement of the end tool, and the actuation operator configured to control the first and second jaws of the end tool to rotate in opposite directions, wherein the yaw operator and the actuation operator are configured to independently rotate from each other,
   when the pitch operator rotates, rotation of the pitch operator is transferred to the end tool joint member and the first and second jaws connected to the end tool joint member via the pitch wire so that the first and second jaws are rotated in an identical direction with a rotation direction of the pitch operator, when the yaw operator rotates, rotation of the yaw operator is transferred to the end tool joint member and the first and second jaws connected to the end tool joint member via the yaw wire so that the first and second jaws are rotated in an identical direction with a rotation direction of the yaw operator, when the actuation operator rotates, rotation of the actuation operator is transferred to the first and second jaws via the actuation wire so that the first and second jaws are rotated in opposite directions to each other, and a center axis of the pitch operating grip in the third direction is formed to be closer to the end tool than a center axis of the pitch operating joint in the third direction.

13. The surgical instrument of claim 1, wherein the power transfer assembly comprises a pitch wire connected to the manipulator to transfer a pitch movement of the manipulator to the end tool, a yaw wire connected to the manipulator to transfer a yaw movement of the manipulator to the end tool, and an actuation wire connected to the manipulator to transfer an actuation movement of the manipulator to the end tool, the manipulator comprises the pitch operator configured to control a pitch movement of the end tool, the yaw operator coupled to the pitch operator and configured to control a yaw movement of the end tool, and an actuation operator configured to control the first and second jaws of the end tool to rotate in opposite directions, wherein the yaw operator and the actuation operator are configured to independently rotate from each other, when the pitch operator rotates, rotation of the pitch operator is transferred to the end tool joint member and the first and second jaws connected to the end tool joint member via the pitch wire so that the first and second jaws are rotated in an identical direction with a rotation direction of the pitch operator, when the yaw operator rotates, rotation of the yaw operator is transferred to the end tool joint member and the first and second jaws connected to the end tool joint member via the yaw wire so that the first and second jaws are rotated in an identical direction with a rotation direction of the yaw operator, when the actuation operator rotates, rotation of the actuation operator is transferred to the first and second jaws via the actuation wire so that the first and second jaws are rotated in opposite directions to each other, and a center axis of the pitch operating grip in the third direction and the center axis of the pitch operating joint in the third direction are provided at substantially identical distances from the end tool.

14. The surgical instrument of claim 1, wherein the power transfer assembly comprises a pitch wire connected to the manipulator to transfer a pitch movement of the manipulator to the end tool, a yaw wire connected to the manipulator to transfer a yaw movement of the manipulator to the end tool, and an actuation wire connected to the manipulator to transfer an actuation movement of the manipulator to the end tool, the manipulator comprises a pitch operator configured to control a pitch movement of the end tool, a yaw operator coupled to the pitch operator and configured to control a yaw movement of the end tool, and an actuation operator configured to control the first and second jaws of the end tool to rotate in opposite directions, wherein the yaw operator and the actuation operator are configured to independently rotate from each other, when the pitch operator rotates, rotation of the pitch operator is transferred to the end tool joint member and the first and second jaws connected to the end tool joint member via the pitch wire so that the first and second jaws are rotated in an identical direction with a rotation direction of the pitch operator, when the yaw operator rotates, rotation of the yaw operator is transferred to the end tool joint member and the first and second jaws connected to the end tool joint member via the yaw wire so that the first and second jaws are rotated in an identical direction with a rotation direction of the yaw operator, when the actuation operator rotates, rotation of the actuation operator is transferred to the first and second jaws via the actuation wire so that the first and second jaws are rotated in opposite directions to each other, and a center axis of the pitch operating grip in the third direction is formed to be farther from the end tool than a center axis of the pitch operating joint in the third direction.

15. The surgical instrument of claim 1, wherein the power transfer assembly comprises:
 a pitch wire configured to transfer a pitch movement of the manipulator to the end tool by being connected to the manipulator;
 a yaw wire configured to transfer a yaw movement of the manipulator to the end tool by being connected to the manipulator; and
 an actuation wire configured to transfer an actuation movement of the manipulator to the end tool by being connected to the manipulator,
 wherein an operation of the pitch wire, an operation of the yaw wire, and an operation of the actuation wire are independently performed.

16. The surgical instrument of claim 15, wherein an actuation movement of the end tool is performed by a reciprocating movement of the actuation wire.

17. The surgical instrument of claim 15, wherein the first jaw and the second jaw connected to the actuation wire are rotated by the linear reciprocating movement of the actuation wire.

18. The surgical instrument of claim 15, wherein two end portions of the pitch wire are respectively coupled to the end tool to extend towards the manipulator, and
 the actuation wire is formed between the two end portions of the pitch wire.

19. The surgical instrument of claim 15, wherein two end portions of the yaw wire are respectively coupled to the end tool to extend towards the manipulator, and
 the actuation wire is formed between the two end portions of the yaw wire.

20. The surgical instrument of claim 15, wherein two end portions of the pitch wire are respectively coupled to the end tool to extend towards the manipulator, and
 two end portions of the yaw wire are respectively coupled to the end tool to extend towards the manipulator, and
 a virtual line connecting the two end portions of the pitch wire and a virtual line connecting the two end portions of the yaw wire are formed to be perpendicular to each other.

21. The surgical instrument of claim 15, wherein a guide hole is formed in one end portion of the first jaw and a guide hole is formed in one end portion of the second jaw, an actuation guide pin is inserted through the guide holes in the first jaw and the second jaw, the actuation wire is coupled to the actuation guide pin, and when the actuation wire translates, the actuation guide pin connected to the actuation wire translates along with the guide holes so that the actuation operation of the first jaw and the second jaw is performed.

22. The surgical instrument of claim 1, wherein the end tool joint member is a node type joint member that connects the end tool to the connection assembly and comprises one or more pitch nodes configured to be rotatable about the second direction (Y-axis) and one or more yaw nodes configured to be rotatable about the third direction (Z-axis).

23. The surgical instrument of claim 22, wherein the one or more pitch nodes and the one or more yaw nodes are alternately arranged.

24. The surgical instrument of claim 22, further comprising an elastic member accommodated in the one or more pitch nodes and/or the one or more yaw nodes and configured to provide a predetermined elastic force to the one or more pitch nodes and/or the one or more yaw nodes.

25. The surgical instrument of claim 1, wherein the yaw operator is coupled to an end portion of the pitch operator.

26. The surgical instrument of claim 25, wherein the yaw operator comprises:

a yaw rotating axis configured to be rotatable about the third direction (Z-axis); and a yaw rotating member connected to the yaw rotating axis and configured to be rotatable with the yaw rotating axis.

27. The surgical instrument of claim 25, wherein the yaw operator comprises a bendable type joint member configured to be rotatable about the third axis (Z-axis), and comprising a plurality of recesses formed in an outer circumferential surface thereof along the first direction, wherein one or more ribs for guiding a bending direction of the yaw operator are formed in each of the plurality of recesses.

28. The surgical instrument of claim 25, wherein the yaw operator comprises a gear type joint member comprising one or more yaw gears configured to be rotatable about the third direction (Z-axis).

29. The surgical instrument of claim 25, wherein the yaw operator comprises a node type joint member comprising one or more yaw nodes configured to be rotatable about the third direction (Z-axis).

30. The surgical instrument of claim 1, wherein a center axis of the pitch operating grip in the third direction is formed to be closer to the end tool than a center axis of the pitch operating joint in the third direction.

31. The surgical instrument of claim 30, wherein the manipulator is provided so that at least a part of the manipulator is closer to the end tool than a virtual center axis of the pitch operating joint in the third direction, in at least one operating stage in which the manipulator is rotated by a predetermined angle about the second direction (Y-axis) for a pitch operation.

32. The surgical instrument of claim 1, wherein a center axis of the pitch operating grip in the third direction and the center axis of the pitch operating joint in the third direction are provided at substantially identical distances from the end tool.

33. The surgical instrument of claim 32, wherein the manipulator is provided so that at least a part of the manipulator is closer to the end tool than a virtual center axis of the pitch operating joint in the third direction, in at least one operating stage in which the manipulator is rotated by a predetermined angle about the second direction (Y-axis) for a pitch operation.

34. The surgical instrument of claim 1, wherein a center axis of the pitch operating grip in the third direction is formed to be farther from the end tool than a center axis of the pitch operating joint in the third direction.

35. The surgical instrument of claim 34, wherein the manipulator is provided so that at least a part of the manipulator is closer to the end tool than a virtual center axis of the pitch operating joint in the third direction, in at least one operating stage in which the manipulator is rotated by a predetermined angle about the second direction (Y-axis) for a pitch operation.

36. A surgical instrument comprising:

an end tool configured to be rotatable in at least two directions;

a manipulator comprising a pitch operator configured to control a pitch movement of the end tool, a yaw operator configured to control a yaw movement of the end tool, and an actuation operator configured to control an actuation movement of the end tool, wherein at least one of the pitch operator and the yaw operator comprises a joint member that is capable of being bent in one or more directions;

a power transfer assembly configured to transfer an operation of the manipulator to the end tool; and a connection assembly configured to extend in a first direction (X-axis), and to connect the manipulator to the end tool when the end tool is coupled to an end portion of the connection assembly and the manipulator is coupled to the other end portion of the connection assembly, wherein at least a part of the manipulator extends towards the end tool, wherein the pitch operator comprises:

a pitch operating joint that is the joint member configured to be rotatable about a second direction (Y-axis) that is perpendicular to the first direction; and a pitch operating grip configured to be rotatable with the pitch operating joint by being connected to the pitch operating joint, wherein, in a third direction (Z-axis) that is respectively perpendicular to the first direction and the second direction, at least a part of the pitch operating grip is formed to be closer to the end tool than a virtual center axis of the pitch operating joint in the third direction, in at least one operating stage of the pitch operator, wherein the end tool comprises a first jaw and a second jaw, each formed to be rotatable, and an end tool joint member capable of being bent in one or more directions to perform a pitch operation and/or a yaw operation of the first jaw and the second jaw, and the manipulator is configured to control operations of the first and second jaws of the end tool, wherein the yaw operator is coupled to an end portion of the pitch operator, wherein the pitch operating joint is a node type joint member comprising one or more pitch nodes configured to be rotatable about the second direction (Y-axis).

* * * * *